United States Patent
Mokkapati et al.

(10) Patent No.: US 10,480,036 B2
(45) Date of Patent: Nov. 19, 2019

(54) METHODS OF DETECTING INFLUENZA

(71) Applicant: CEPHEID, Sunnyvale, CA (US)

(72) Inventors: Anupama Mokkapati, Sunnyvale, CA (US); Bradley Brown, Sunnyvale, CA (US); Robert Jones, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 15/504,901

(22) PCT Filed: Aug. 22, 2014

(86) PCT No.: PCT/US2014/052288
§ 371 (c)(1),
(2) Date: Feb. 17, 2017

(87) PCT Pub. No.: WO2016/028312
PCT Pub. Date: Feb. 25, 2016

(65) Prior Publication Data
US 2017/0275712 A1 Sep. 28, 2017

(51) Int. Cl.
*C12Q 1/70* (2006.01)
*C12Q 1/68* (2018.01)

(52) U.S. Cl.
CPC .................................. *C12Q 1/701* (2013.01)

(58) Field of Classification Search
None
See application file for complete search history.

(56) References Cited

U.S. PATENT DOCUMENTS

| | | | |
|---|---|---|---|
| 2007/0065813 A1 | 3/2007 | Hayden et al. | |
| 2012/0258456 A1* | 10/2012 | Armes | G01N 21/6428 435/6.11 |

FOREIGN PATENT DOCUMENTS

| CN | 103305634 | * | 9/2013 |
|---|---|---|---|
| KR | 1020110009383 | * | 9/2013 |
| WO | WO 2007/017759 | * | 2/2007 |
| WO | 2007047778 A2 | | 4/2007 |
| WO | WO 2007/047778 | * | 4/2007 |
| WO | WO 2008/115851 | * | 9/2008 |
| WO | 2008140513 A1 | | 11/2008 |
| WO | 2010128396 A2 | | 11/2010 |

OTHER PUBLICATIONS

GenBank Accession No. KC471392 (published May 31, 2013) with alignment.*
Deng et al., PLoS ONE, 2011, 6(8):e23400. (Year: 2011).*
Chan et al., "Amplification of the entire genome of influenza A virus H1N1 and H3N2 subtypes by reverse-transcription polymerase chain reaction", Journal of Virological Methods, Elsevier BV, NL, vol. 136, No. 1-2, Sep. 1, 2006 (Sep. 1, 2006), pp. 38-43.
Hoffmann et al., "Universal primer set for the full-length amplification of all influenza A viruses", Archives of Virology, Springer Wien, AT, vol. 146, Jan. 1, 2001 (Jan. 1, 2001), pp. 2275-2289.
Zhao et al., "Genetic characteristics of 2009 pandemic H1N1 influenza a viruses isolated from Mainland China", Virologica Sinica, SP Wuhan Institute of Virology, CAS, Heidelberg, vol. 26, No. 6, Dec. 10, 2011 (Dec. 10, 2011), pp. 418-427.
Fereidouni et al., "Saving resources: Avian influenza surveillance using pooled swab samples and reduced reaction volumes in real-time RT-PCR", Journal of Virological Methods, vol. 186, No. 1-2, Dec. 1, 2012 (Dec. 1, 2012), pp. 119-125.
Nagatani et al., "Semi-real time electrochemical monitoring for influenza virus RNA by reverse transcription loop-mediated isothermal amplification using a USB powered portable potentiostat", The Analyst, vol. 136, No. 24, Jan. 1, 2011 (Jan. 1, 2011), p. 5143.
Yu et al., "Preparation of Armored RNA as a Control for Multiplex Real-Time Reverse Transcription-PCR Detection of Influenza Virus and Severe Acute Respiratory Syndrome Coronavirus", Journal of Clinical Microbiology, vol. 46, No. 3, Dec. 26, 2007 (Dec. 26, 2007), pp. 837-841.
International Search Report and Written Opinion for International Application No. PCT/US2014/052288, dated Jun. 24, 2015 (22 pages).

* cited by examiner

*Primary Examiner* — Nicole Kinsey White
(74) *Attorney, Agent, or Firm* — McNeill Baur PLLC

(57) ABSTRACT

Compositions and methods for detecting influenza are provided.

11 Claims, No Drawings

Specification includes a Sequence Listing.

METHODS OF DETECTING INFLUENZA

1. FIELD OF THE INVENTION

Compositions and methods for detecting influenza are provided. In particular, influenza markers and panels of markers useful in the detection of influenza are provided.

2. BACKGROUND

Influenza, or the flu, is a contagious viral infection of the respiratory tract. Transmission of influenza is primarily airborne (i.e., coughing or sneezing); the peak of transmission usually occurs in the winter months. Symptoms commonly include fever, chills, headache, muscle aches, malaise, cough, and sinus congestion. Gastrointestinal symptoms (i.e., nausea, vomiting, or diarrhea) may also occur, primarily in children, but are less common in adults. Symptoms generally appear within two days of exposure to an infected person. Pneumonia may develop as a complication of influenza infection, causing increased morbidity and mortality in pediatric, elderly, and immunocompromised populations. Influenza viruses are classified into types A, B, and C, the former two of which cause most human infections. Influenza A is the most common type of influenza virus in humans, and is generally responsible for seasonal flu epidemics and occasionally for pandemics. Influenza A viruses can also infect animals such as birds, pigs, and horses. Infections with influenza B virus are generally restricted to humans and are less frequent causes of epidemics. Influenza A viruses are further divided into subtypes on the basis of two surface proteins: hemagglutinin (H) and neuraminidase (N). Seasonal flu is normally caused by subtypes H1, H2, H3, and N1 and N2. In addition to seasonal flu, a novel H1N1 strain was identified in humans in the United States in early 2009.

Respiratory syncytial virus (RSV), a member of the Paramyxoviridae family consisting of two strains (subgroups A and B), is also the cause of a contagious disease that afflicts primarily infants and the elderly who are immune-compromised, e.g., chronic lung or heart disease or undergoing treatment for conditions that reduces the strength of their immune system. The virus can live for hours on countertops and toys and cause both upper respiratory infections, such as colds, and lower respiratory infections manifesting as bronchiolitis and pneumonia.4 By the age of two, most children have already been infected by RSV, but because only weak immunity develops, both children and adults can become reinfected. Symptoms usually appear four to six days after infection. The disease is typically self-limiting, lasting about one to two weeks in infants. In adults, the infection lasts about five days and presents with symptoms consistent with a cold, such as rhinorrhea, fatigue, headache, and fever. The RSV season overlaps with influenza season somewhat as infections begin to rise during the fall and continue through early spring. RSV infections, however, also occur at other times of the year, although rarely.

Active surveillance programs in conjunction with infection control precautions are important components for preventing transmission of influenza and RSV. The use of assays providing rapid results to identify patients infected with these seasonal infections is also an important factor for effective control, proper choice of treatment, and prevention of widespread outbreaks.

The genome of influenza viruses comprises eight RNA segments of 0.9-2.3 kb that together span approximately 13.5 kb and encode 11 proteins. These 8 segments designated PB2, PB1, PA, HA, NP, NA, MP and NS are under constant selective pressure which leads to rapid sequence changes (antigenic drift). In addition to changes on the sequence level Influenza A has the ability to exchange whole segments with other Influenza A viruses (antigenic shift). This process leads to the emergence of pandemic influenza strains (i.e. Influenza A H1N1pdm09, swing origin H3N2).

The two proteins, hemagglutinin (HA) and neuraminidase (NA) determine the subtypes (H and N, respectively) of Influenza A virus. There are 16 H subtypes and 9 N subtypes. The H1N1 and H3N2 subtypes cause the vast majority of influenza infections in humans. Influenza B virus has a similar structure of RNA segments; however the Flu B viruses do not have subtypes.

This constant antigenic drift and antigenic shift makes it difficult to maintain influenza detection assays from season to season. There remains a need for a robust influenza detection assay that will remain accurate even as the influenza genome undergoes genetic drift.

3. SUMMARY

In some embodiments, methods of detecting the presence or absence of influenza in a sample from a subject are provided. In some embodiments, a method comprises detecting the presence or absence of at least one influenza gene selected from polymerase acidic (PA) and polymerase basic 2 (PB2) in the sample.

In some embodiments, methods of determining whether a subject has influenza are provided. In some embodiments, a method comprises detecting the presence or absence of at least one influenza gene selected from a polymerase acidic (PA) gene and a polymerase basic 2 (PB2) gene in a sample from the subject.

In some embodiments, a method comprises detecting the presence of absence of a PA gene. In some embodiments, a method comprises detecting the presence of absence of a PB2 gene. In some embodiments, a method comprises detecting the presence of absence of a PA gene and a PB2 gene. In some embodiments, the PA gene and/or PB2 gene is an influenza A gene. In some embodiments, the sequence of the PA gene is at least 95% identical to the sequence of SEQ ID NO: 2. In some embodiments, the sequence of the PB2 gene is at least 95% identical to the sequence of SEQ ID NO: 1.

In some embodiments, the method further comprises detecting the presence or absence of at least one influenza matrix protein (MP) gene. In some embodiments, the method comprises detecting the presence or absence of an influenza A MP gene. In some embodiments, the method comprises detecting the presence or absence of an influenza B MP gene. In some embodiments, the method comprises detecting the presence or absence of an influenza A MP gene and an influenza B MP gene. In some embodiments, the method comprises detecting the presence or absence of an avian influenza MP gene. In some embodiments, the avian influenza MP gene is a hemagglutinin (H) 5 or H7 subtype. In some embodiments, the sequence of the influenza A MP gene is at least 95% identical to the sequence of SEQ ID NO: 3 or 4. In some embodiments, the sequence of the influenza B MP gene is at least 95% identical to the sequence of SEQ ID NO: 6.

In some embodiments, the method further comprises detecting the presence or absence of at least one influenza nonstructural (NS) gene. In some embodiments, the method comprises detecting the presence or absence of an influenza B NS gene. In some embodiments, the sequence of the influenza B NS gene is at least 95% identical to the sequence of SEQ ID NO: 7.

In some embodiments, the method further comprises detecting the presence or absence of at least one influenza hemagglutinin (HA) gene. In some embodiments, the method comprises detecting the presence or absence of an influenza A HA gene. In some embodiments, the method comprises detecting the presence or absence of an avian influenza HA gene. In some embodiments, the avian influenza is an H7 subtype. In some embodiments, the sequence of the influenza HA gene is at least 95% identical to the sequence of SEQ ID NO: 5.

In some embodiments, the method comprises detecting the presence or absence of an influenza A PA gene, an influenza A PB2 gene, an influenza A MP gene, an avian influenza MP gene, and an avian influenza HA gene. In some embodiments, the sequence of the influenza A PA gene is at least 95% identical to SEQ ID NO: 2, the sequence of the influenza A PB2 gene is at least 95% identical to SEQ ID NO: 1, the sequence of the influenza A MP gene is at least 95% identical to SEQ ID NO: 3, the sequence of the avian influenza MP gene is at least 95% identical to SEQ ID NO: 4, and the sequence of the avian influenza HA gene is at least 95% identical to SEQ ID NO: 5.

In some embodiments, the method comprises detecting the presence or absence of an influenza B MP gene and an influenza B NS gene. In some embodiments, the sequence of the influenza B MP gene is at least 95% identical to SEQ ID NO: 6 and the sequence of the influenza B NS gene is at least 95% identical to SEQ ID NO: 7.

In some embodiments, detection of the presence of any one of the influenza genes indicates the presence of influenza in the sample. In some embodiments, the method distinguishes between influenza A and influenza B. In some embodiments, the method does not distinguish between influenza A and influenza B.

In some embodiments, the method comprises detecting the presence or absence of respiratory syncytial virus (RSV) in a sample from the subject. In some embodiments, the method comprises detecting the presence or absence of RSV A. In some embodiments, the method comprises detecting the presence or absence of RSV B. In some embodiments, the method comprises detecting the presence or absence of RSV A and RSV B.

In some embodiments, wherein the subject has one or more symptoms of influenza. In some embodiments, the subject has one or more symptoms selected from fever, chills, cough, sore throat, runny nose, nasal congestion, muscle ache, headache, fatigue, vomiting, and diarrhea.

In some embodiments, the method comprises detecting an exogenous control. In some embodiments, the exogenous control is a sample processing control. In some embodiments, the exogenous control comprises an RNA sequence that is not expected to be present in the sample. In some embodiments, the exogenous control is an Armored® RNA.

In some embodiments, the method comprises PCR. In some embodiments, the method comprises quantitative PCR. In some embodiments, the PCR reaction takes less than 2 hours from an initial denaturation step through a final extension step.

In some embodiments, the method comprises contacting nucleic acids from the sample with a first primer pair for detecting the influenza PA gene. In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 2, and wherein the second primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 2. In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 20, and wherein the second primer comprises a sequence that is at least 90%, at least 95%, or 100% complementary to at least 15, at least 16, at least 17, at least 18, at least 19, or at least 20 contiguous nucleotides of SEQ ID NO: 21. In some embodiments, the first primer has the sequence of SEQ ID NO: 20 and the second primer has the sequence of SEQ ID NO: 21.

In some embodiments, the method comprises contacting nucleic acids from the sample with a second primer pair for detecting the influenza PB2 gene. In some embodiments, the second primer pair comprises a third primer and a fourth primer, wherein the third primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 1, and wherein the fourth primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 1. In some embodiments, the second primer pair comprises a third primer and a fourth primer, wherein the third primer comprises a sequence that is at least 90%, at least 95%, or 100% identical to at least 15, at least 16, at least 17, at least 18, at least 19, or at least 20 contiguous nucleotides of SEQ ID NO: 17, and wherein the fourth primer comprises a sequence that is at least 90%, at least 95%, or 100% complementary to at least 15, at least 16, at least 17, at least 18, at least 19, or at least 20 contiguous nucleotides of SEQ ID NO: 18. In some embodiments, the third primer has the sequence of SEQ ID NO: 17 and the fourth primer has the sequence of SEQ ID NO: 18.

In some embodiments, the method comprises contacting nucleic acids from the sample with at least one additional primer pair, wherein each of the additional primer pairs is for detecting a different influenza gene selected from an influenza A MP gene, an avian influenza MP gene, and an avian influenza HA gene. In some embodiments, each additional primer pair comprises a fifth primer and a sixth primer independently selected from: (a) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 3, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 3; (b) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 4, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 4; (c) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 5, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 5; (d) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 23, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 24; (e) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 26, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 27; and (f) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 29, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 30.

In some embodiments, the method comprises contacting nucleic acids from the sample with at least one additional primer pair, wherein each of the additional primer pairs is for detecting a different influenza gene selected from an influenza B MP gene and an influenza B NS gene. In some embodiments, each additional primer pair comprises a seventh primer and an eighth primer independently selected from: (a) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 6, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 6; (b) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 7, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 7; (c) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 32, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 33; and (d) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 35, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 36.

In some embodiments, the method comprises contacting nucleic acids from the sample with at least one additional primer pair, wherein each of the additional primer pairs is for detecting RSV A or RSV B. In some embodiments, each additional primer pair comprises a ninth primer and a tenth primer independently selected from: (a) a ninth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 38, and a tenth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 39; and (b) a ninth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 41, and a tenth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 42.

In some embodiments, the method comprises contacting nucleic acids from the sample with primer pairs for detecting an influenza A PA gene, an influenza A PB2 gene, an influenza A MP gene, an avian influenza MP gene, and an avian influenza HA gene. In some embodiments, the method further comprises contacting nucleic acids from the sample with primer pairs for detecting RSV A and RSV B. In some embodiments, the method comprises contacting nucleic acids from the sample with a control primer pair for detecting an exogenous control. In some embodiments, each primer pair produces an amplicon that is 50 to 500 nucleotides long, 50 to 400 nucleotides long, 50 to 300 nucleotides long, 50 to 200 nucleotides long, or 50 to 150 nucleotides long.

In some embodiments, the method comprises forming an amplicon from each primer pair when the target of the primer pair is present. In some embodiments, the method comprises forming at least one amplicon selected from an influenza A PA amplicon, an influenza A PB2 amplicon. In some embodiments, the influenza A PA amplicon has the sequence of SEQ ID NO: 9 and the influenza A PB2 amplicon has the sequence of SEQ ID NO: 8.

In some embodiments, the method comprises forming at least one amplicon selected from an influenza A MP amplicon, an avian influenza MP amplicon, and an avian influenza HA amplicon. In some embodiments, the influenza A MP amplicon has the sequence of SEQ ID NO: 10, the avian influenza MP amplicon has the sequence of SEQ ID NO: 11, and the avian influenza HA amplicon has the sequence of SEQ ID NO: 12.

In some embodiments, the method further comprises forming an influenza B MP amplicon and/or an influenza B NS amplicon. In some embodiments, the influenza B MP amplicon has the sequence of SEQ ID NO: 13 and the influenza B NS amplicon has the sequence of SEQ ID NO: 14. In some embodiments, the method further comprises forming an RSV A amplicon and/or an RSV B amplicon. In some embodiments, the RSV A amplicon has the sequence of SEQ ID NO: 15 and the RSV B amplicon has the sequence of SEQ ID NO: 16.

In some embodiments, the method comprises contacting the amplicons with at least one probe selected from an influenza A PA probe and an influenza A PB2 probe. In some embodiments, the influenza PA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 2, and the influenza PB2 probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 1. In some embodiments, the influenza PA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 19, and the influenza PB2 probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 22.

In some embodiments, the method comprises contacting the amplicons with at least one probe selected from an influenza A MP probe, an avian influenza MP probe, and an avian influenza HA probe. In some embodiments, the influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 3, and the avian influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 4, and the avian influenza HA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 5. In some embodiments, the influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 25, and the avian influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 28, and the avian influenza HA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 31.

In some embodiments, the method comprises contacting the amplicons with at least one probe selected from an influenza B MP probe and an influenza B NS probe. In some embodiments, the influenza B MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 6, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 7. In some embodiments, the influenza B MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 34, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 37.

In some embodiments, the method comprises contacting the amplicons with at least one probe selected from an RSV A probe and an RSV B probe. In some embodiments, the RSV A probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 15, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 16. In some embodiments, the RSV A probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 40, and the RSV B probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 43.

In some embodiments, each probe comprises a detectable label. In some embodiments, the each probe comprises a fluorescent dye and a quencher molecule. In some embodiments, the influenza A probes and the influenza B probes comprise detectable labels that are detectably different. In some embodiments, the influenza A probes and the influenza B probes comprise detectable labels that are not detectably different. In some embodiments, each probe consists of 15 to 30 nucleotides.

In some embodiments, the method comprises forming an exogenous control amplicon. In some embodiments, the method comprises contacting the exogenous control amplicon with a control probe capable of selectively hybridizing with the exogenous control amplicon.

In some embodiments, the method comprises detecting the presence of absence of at least one influenza A subtype and at least one influenza B subtype and an exogenous control in a single multiplex reaction. In some embodiments, the at least one influenza A subtype includes at least one avian influenza. In some embodiments, the method comprises detecting RSV A and/or RSV B in the same multiplex reaction.

In some embodiments, the sample is selected from a nasopharyngeal swab sample, a nasal aspirate sample, and a nasal wash sample.

In some embodiments, compositions are provided. In some embodiments, a composition comprises a first primer pair for detecting an influenza PA gene. In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 2, and wherein the second primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 2. In some embodiments, the first primer pair comprises a first primer and a second primer, wherein the first primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 20, and wherein the second primer comprises a sequence that is at least 90%, at least 95%, or 100% complementary to at least 15, at least 16, at least 17, at least 18, at least 19, or at least 20 contiguous nucleotides of SEQ ID NO: 21. In some embodiments, the first primer has the sequence of SEQ ID NO: 20 and the second primer has the sequence of SEQ ID NO: 21.

In some embodiments, a composition comprising a second primer pair for detecting an influenza PB2 gene is provided. In some embodiments, the second primer pair comprises a third primer and a fourth primer, wherein the third primer comprises a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 1, and wherein the fourth primer comprises a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 1. In some embodiments, the second primer pair comprises a third primer and a fourth primer, wherein the third primer comprises a sequence that is at least 90%, at least 95%, or 100% identical to at least 15, at least 16, at least 17, at least 18, at least 19, or at least 20 contiguous nucleotides of SEQ ID NO: 17, and wherein the fourth primer comprises a sequence that is at least 90%, at least 95%, or 100% complementary to at least 15, at least 16, at least 17, at least 18, at least 19, or at least 20 contiguous nucleotides of SEQ ID NO: 18. In some embodiments, the third primer has the sequence of SEQ ID NO: 17 and the fourth primer has the sequence of SEQ ID NO: 18.

In some embodiments, a composition comprises at least one additional primer pair, wherein each of the additional primer pairs is for detecting a different influenza gene selected from an influenza A MP gene, an avian influenza MP gene, and an avian influenza HA gene. In some embodiments, each additional primer pair comprises a fifth primer and a sixth primer independently selected from: (a) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 3, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 3; (b) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 4, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 4; (c) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 5, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 5; (d) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 23, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 24; (e) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 26, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 27; and (f) a fifth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 29, and a sixth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 30.

In some embodiments, the composition further comprises at least one additional primer pair, wherein each of the additional primer pairs is for detecting a different influenza gene selected from an influenza B MP gene and an influenza B NS gene. In some embodiments, each additional primer pair comprises a seventh primer and an eighth primer independently selected from: (a) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 6, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 6; (b) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 7, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 7; (c) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 32, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 33; and (d) a seventh primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 35, and an eighth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 36.

In some embodiments, a composition further comprises at least one additional primer pair, wherein each of the additional primer pairs is for detecting RSV A or RSV B. In some embodiments, each additional primer pair comprises a ninth primer and a tenth primer independently selected from: (a) a ninth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 38, and a tenth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 39; and (b) a ninth primer comprising a sequence that is at least 90%, at least 95%, or 100% identical to at least 15, at least 16, at least 17, at least 18, at least 19, at least 20, at least 21, at least 22, at least 23, at least 24, or at least 25 contiguous nucleotides of SEQ ID NO: 41, and a tenth primer comprising a sequence that is at least 90%, at least 95%, or 100% complementary to at least 15, at least 16, at least 17, at least 18, at least 19, at least 20, at least 21, at least 22, at least 23, at least 24, or at least 25 contiguous nucleotides of SEQ ID NO: 42.

In some embodiments, a composition comprises primer pairs for detecting an influenza A PA gene, an influenza A PB2 gene, an influenza A MP gene, an avian influenza MP gene, and an avian influenza HA gene. In some embodiments, a composition further comprises primer pairs for detecting RSV A and RSV B. In some embodiments, a composition further comprises a primer pair for detecting an exogenous control. In some embodiments, the exogenous control is a sample processing control.

In some embodiments, a composition comprises at least one probe selected from an influenza A PA probe and an influenza A PB2 probe. In some embodiments, the influenza PA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 2, and the influenza PB2 probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 1. In some embodiments, the influenza PA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 19, and the influenza PB2 probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 22.

In some embodiments, a composition further comprises at least one probe selected from an influenza A MP probe, an avian influenza MP probe, and an avian influenza HA probe. In some embodiments, the influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 3, and the avian influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 4, and the avian influenza HA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 5. In some embodiments, the influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 25, and the avian influenza MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 28, and the avian influenza HA probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 31.

In some embodiments, the composition further comprises at least one probe selected from an influenza B MP probe and an influenza B NS probe. In some embodiments, the influenza B MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 6, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 7. In some embodiments, the influenza B MP probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 34, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 37.

In some embodiments, the composition further comprises at least one probe selected from an RSV A probe and an RSV B probe. In some embodiments, the RSV A probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 15, and the influenza B NS probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 16. In some embodiments, the RSV A probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 40, and the RSV B probe comprises a sequence that is at least 90%, at least 95%, or 100% identical or complementary to at least 15, at least 16, at least 17, at least 18, at least 19, at least 20, at least 21, at least 22, at least 23, at least 24, or at least 25 contiguous nucleotides of SEQ ID NO: 43.

In some embodiments, the composition further comprises a probe for detecting an exogenous control.

In some embodiments, each probe comprises a detectable label. In some embodiments, each probe comprises a fluorescent dye and a quencher molecule. In some embodiments, each probe consists of 15 to 30 nucleotides.

In some embodiments, the composition is a lyophilized composition. In some embodiments, the composition is in solution. In some embodiments, the composition comprises nucleic acids from a sample from a subject being tested for the presence of absence of influenza. In some embodiments, the sample is selected from a nasopharyngeal swab sample, a nasal aspirate sample, and a nasal wash sample.

In some embodiments, kits are provided. In some embodiments, a kit comprises a composition described herein. In some embodiments, the kit further comprises an exogenous control. In some embodiments, the exogenous control is an Armored® RNA. In some embodiments, the kit comprises dNTPs and/or a thermostable polymerase. In some embodiments, the kit comprises a reverse transcriptase.

In some embodiments, an oligonucleotide consisting of a sequence selected from SEQ ID NOs: 17 to 43 is provided. In some embodiments, the oligonucleotide comprises at least one modified nucleotide. In some embodiments, the oligonucleotide comprises a detectable label. In some embodiments, the oligonucleotide comprises a fluorescent dye and a quencher molecule. In some embodiments, the oligonucleotide is a fluorescence resonance energy transfer (FRET) probe.

In some embodiments, a composition comprising a first primer consisting of the sequence of SEQ ID NO: 17 and a second primer consisting of the sequence of SEQ ID NO: 18, wherein the first primer and the second primer each comprises at least one modified nucleotide is provided. In some embodiments, the composition comprises a probe consisting of the sequence of SEQ ID NO: 19, wherein the probe comprises at least one modified nucleotide and/or a detectable label.

In some embodiments, a composition comprising a first primer consisting of the sequence of SEQ ID NO: 20 and a second primer consisting of the sequence of SEQ ID NO: 21, wherein the first primer and the second primer each comprises at least one modified nucleotide is provided. In some embodiments, the composition comprises a probe consisting of the sequence of SEQ ID NO: 22, wherein the probe comprises at least one modified nucleotide and/or a detectable label. In some embodiments, the probe is a fluorescence resonance energy transfer (FRET) probe. In some embodiments, the probe comprises at least one modified nucleotide. In some embodiments, the composition is a lyophilized composition. In some embodiments, the composition is in solution. In some embodiments, the composition comprises nucleic acids of a sample from a subject.

4. DETAILED DESCRIPTION

4.1. Definitions

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "detectably different" refers to a set of labels (such as dyes) that can be detected and distinguished simultaneously.

As used herein, the terms "patient" and "subject" are used interchangeably to refer to a human. In some embodiments, the methods described herein may be used on samples from non-human animals.

As used herein, the terms "oligonucleotide," "polynucleotide," "nucleic acid molecule," and the like, refer to nucleic acid-containing molecules, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "oligonucleotide," refers to a single-stranded polynucleotide having fewer than 500 nucleotides. In some embodiments, an oligonucleotide is 8 to 200, 8 to 100, 12 to 200, 12 to 100, 12 to 75, or 12 to 50 nucleotides long. Oligonucleotides may be referred to by their length, for example, a 24 residue oligonucleotide may be referred to as a "24-mer."

As used herein, the term "complementary" to a target RNA (or target region thereof), and the percentage of "complementarity" of the probe sequence to that of the target RNA sequence is the percentage "identity" to the sequence of target RNA or to the reverse complement of the sequence of the target RNA. In determining the degree of "complementarity" between probes used in the compositions described herein (or regions thereof) and a target RNA, such as those disclosed herein, the degree of "complementarity" is expressed as the percentage identity between the sequence of the probe (or region thereof) and sequence of the target RNA or the reverse complement of the sequence of the target RNA that best aligns therewith. The percentage is calculated by counting the number of aligned bases that are identical as between the 2 sequences, dividing by the total number of contiguous nucleotides in the probe, and multiplying by 100. When the term "complementary" is used, the subject oligonucleotide is at least 90% complementary to the target molecule, unless indicated otherwise. In some embodiments, the subject oligonucleotide is at least 91%, at least 92%, at least 93%, at least 94%, at least 95%, at least 96%, at least 97%, at least 98%, at least 99%, or 100% complementary to the target molecule.

A "primer" or "probe" as used herein, refers to an oligonucleotide that comprises a region that is complementary to a sequence of at least 8 contiguous nucleotides of a target nucleic acid molecule, such as DNA (e.g., a target gene) or an mRNA (or a DNA reverse-transcribed from an mRNA). In some embodiments, a primer or probe comprises a region that is complementary to a sequence of at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of a target molecule. When a primer or probe comprises a region that is "complementary to at least x contiguous nucleotides of a target molecule," the primer or probe is at least 95% complementary to at least x contiguous nucleotides of the target molecule. In some embodiments, the primer or probe is at least 96%, at least 97%, at least 98%, at least 99%, or 100% complementary to the target molecule.

The term "nucleic acid amplification," encompasses any means by which at least a part of at least one target nucleic acid is reproduced, typically in a template-dependent manner, including without limitation, a broad range of techniques for amplifying nucleic acid sequences, either linearly or exponentially. Exemplary means for performing an amplifying step include polymerase chain reaction (PCR), ligase chain reaction (LCR), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), digital amplification, and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

Unless otherwise indicated, the term "hybridize" is used herein refer to "specific hybridization" which is the binding, duplexing, or hybridizing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. A "stringent hybridization" and "stringent hybridization wash conditions" in the context of nucleic acid hybridization (e.g., as in array, Southern, or Northern hybridization) are sequence-dependent and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. ("Tijssen"). Generally, highly stringent hybridization and wash conditions for filter hybridizations are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. Dependency of hybridization stringency on buffer composition, temperature, and probe length are well known to those of skill in the art (see, e.g., Sambrook and Russell (2001) Molecular Cloning: A Laboratory Manual (3rd ed.) Vol. 1-3, Cold Spring Harbor Laboratory, Cold Spring Harbor Press, NY).

A "sample," as used herein, includes various nasal samples, such as nasopharyngeal swab samples, nasal aspirate samples, nasal wash samples, and other types of human samples. In some embodiments, a nasal sample comprises a buffer, such as a preservative. Further nonlimiting exemplary samples include nasal swabs, oropharyngeal swabs, throat swabs, bronchoalveolar lavage samples, bronchial aspirates, bronchial washes, endotracheal aspirates, endotracheal washes, tracheal aspirates, nasal secretion samples, mucus samples, sputum samples, and lung tissue samples. In some embodiments, the sample comprises a buffer, such as a preservative.

An "endogenous control," as used herein refers to a moiety that is naturally present in the sample to be used for detection. In some embodiments, an endogenous control is a "sample adequacy control" (SAC), which may be used to determine whether there was sufficient sample used in the assay, or whether the sample comprised sufficient biological material, such as cells. In some embodiments, an endogenous control is an RNA (such as an mRNA, tRNA, ribosomal RNA, etc.), such as a human RNA. Nonlimiting exemplary endogenous controls include ABL mRNA, GUSB mRNA, GAPDH mRNA, TUBB mRNA, and UPK1a mRNA. In some embodiments, an endogenous control, such as an SAC, is selected that can be detected in the same manner as the target RNA is detected and, in some embodiments, simultaneously with the target RNA.

An "exogenous control," as used herein, refers to a moiety that is added to a sample or to an assay, such as a "sample processing control" (SPC). In some embodiments, an exogenous control is included with the assay reagents. An exogenous control is typically selected that is not expected to be present in the sample to be used for detection, or is present at very low levels in the sample such that the amount of the moiety naturally present in the sample is either undetectable or is detectable at a much lower level than the amount added to the sample as an exogenous control. In some embodiments, an exogenous control comprises a nucleotide sequence that is not expected to be present in the sample type used for detection of the target RNA. In some embodiments, an exogenous control comprises a nucleotide sequence that is not known to be present in the species from whom the sample is taken. In some embodiments, an exogenous control comprises a nucleotide sequence from a different species than the subject from whom the sample was taken. In some embodiments, an exogenous control comprises a nucleotide sequence that is not known to be present in any species. In some embodiments, an exogenous control is selected that can be detected in the same manner as the target RNA is detected and, in some embodiments, simultaneously with the target RNA. In some embodiments, the exogenous control is an RNA. In some such embodiments, the exogenous control is an Armored RNA®, which comprises RNA packaged in a bacteriophage protective coat. See, e.g., WalkerPeach et al., *Clin. Chem.* 45:12: 2079-2085 (1999).

In the sequences herein, "U" and "T" are used interchangeably, such that both letters indicate a uracil or thymine at that position. One skilled in the art will understand from the context and/or intended use whether a uracil or thymine is intended and/or should be used at that position in the sequence. For example, one skilled in the art would understand that native RNA molecules typically include uracil, while native DNA molecules typically include thymine. Thus, where an RNA sequence includes "T", one skilled in the art would understand that that position in the native RNA is likely a uracil.

In the present disclosure, "a sequence selected from" encompasses both "one sequence selected from" and "one or more sequences selected from." Thus, when "a sequence selected from" is used, it is to be understood that one, or more than one, of the listed sequences may be chosen.

In the present disclosure, a method that comprises detecting a "a set of influenza A (fluA) markers consisting of . . . " involves detection of only the fluA markers of the set, and not any further fluA markers. The method may comprise additional components or steps, however, such as for detecting fluB, respiratory syncytial virus (RSV), and/or endogenous and/or exogenous controls. Similarly, a method or composition that comprises "a set of influenza A (fluA) marker primer pairs" and/or "a set of fluA marker probes" can include primer pairs and/or probes for only the fluA markers of the set, and not for any other fluA markers. The method or composition may comprise additional components, however, such as one or more fluB primer pairs, RSV primer pairs, endogenous control primer pairs and/or exogenous control primer pairs.

4.2. Detecting Influenza A

The present inventors have developed a more sensitive assay for detecting Influenza A. In some embodiments, the assay comprises detecting the Flu A polymerase basic 2 (PB2) gene and/or the Flu A polymerase acidic (PA) gene. In some embodiments, the assay comprises detecting PA and/or PB2 in addition to the Flu A matrix protein (MP) gene. The present assay relies on the polymerase chain reaction (PCR), and can be carried out in a substantially automated manner using a commercially available nucleic acid amplification system. Exemplary nonlimiting nucleic acid amplification systems that can be used to carry out the methods of the invention include the GeneXpert® system, a GeneXpert® Infinity system, and a Smartcycler System (Cepheid, Sunnyvale, Calif.). The present assay can be completed in under 3 hours, and in some embodiments, under 2 hours, using an automated system, for example, the GeneXpert® system.

4.2.1. General Methods

Compositions and methods for detecting Flu A are provided. In some embodiments, the method comprises detecting the Flu A PB2 gene and/or PA gene. In some embodiments, the method comprises detecting the Flu A PB2 gene and PA gene. In some embodiments, the method comprises detecting the Flu A PB2 gene and/or PA gene, and also detecting the Flu A MP gene. In some embodiments, the method comprises detecting one or more of avian Flu (such as Flu A 2 and/or Flu A 3), Flu B, RSV A, and RSV B.

In some embodiments, a method of detecting Flu A in a subject comprises detecting the presence of the Flu A PB2 gene and/or PA gene in a sample from the subject. In some embodiments, the method comprises detecting the Flu A PB2 gene and PA gene in a sample from the subject. In some embodiments, the sample is selected from a nasopharyngeal swab sample, a nasal aspirate sample, and a nasal wash sample.

In some embodiments, a method of detecting Flu A further comprises detecting at least one endogenous control, such as a sample adequacy control (SAC). In some embodiments, a method of detecting Flu A further comprises detecting at least one exogenous control, such as a sample processing control (SPC). In some embodiments, the SPC is Armored® RNA.

In some embodiments, a method of detecting Flu A comprises detecting the Flu A PB2 gene and/or PA gene in a sample. In some embodiments, a method of detecting Flu A further comprises detecting a sample processing control (SPC), such as an Armored® RNA.

In the present disclosure, the terms "target RNA" and "target gene" are used interchangeably to refer to the Flu A PB2 gene and Flu A PA gene, and also to other Flu and RSV genes, as well as to exogenous and/or endogenous controls. Thus, it is to be understood that when a discussion is presented in terms of a target gene, that discussion is specifically intended to encompass the Flu A PB2 gene and Flu A PA gene, other Flu and RSV genes, any endogenous control(s) (e.g., SAC), and any exogenous control(s) (e.g., SPC).

In some embodiments, the presence of the Flu A PB2 gene and/or Flu A PA gene is detected in a nasal sample. In some embodiments, the target gene is detected in a nasal aspirate sample or a nasal wash sample. In some embodiments, a target gene is detected in a sample to which a buffer (such as a preservative) has been added. In some embodiments, the presence of the Flu A PB2 gene and/or Flu A PA gene is detected in a nasopharyngeal swab sample. In some embodiments, the target gene is detected in an nasopharyngeal swab sample that has been placed in a buffer (such as a preservative).

In some embodiments, detection of the Flu A PB2 gene and/or Flu A PA gene in a sample from a subject indicates the presence of Flu A in the subject. In some embodiments, detection of the Flu A PB2 gene and/or Flu A PA gene in a sample from a subject indicates the presence of Flu A 1 in the subject. In some embodiments, the detecting is done quantitatively. In other embodiments, the detecting is done qualitatively. In some embodiments, detecting a target gene comprises forming a complex comprising a polynucleotide and a nucleic acid selected from a target gene, a cDNA reverse transcribed from a target gene, a DNA amplicon of a target gene, and a complement of a target gene. In some embodiments, detecting a target gene comprises RT-PCR. In some embodiments, detecting a target gene comprises quantitative RT-PCR or real-time RT-PCR. In some embodiments, a sample adequacy control (SAC) and/or a sample processing control (SPC) is detected in the same assay as the target gene. In some embodiments, if the Flu A PB2 gene or Flu A PA gene is detected, Flu A is considered to be detected even if the SPC is not detected in the assay. In some embodiments, if the Flu A PB2 gene and Flu A PA gene are not detected, Flu A is considered to be not detected only if the SPC is detected in the assay.

In some embodiments, the presence of the Flu A PB2 gene and/or Flu A PA gene can be measured in samples collected at one or more times from a subject to monitor treatment for Flu in the subject. In some embodiments, the present assay may be used as part of routine and/or preventative healthcare for a subject. In some embodiments, the present assay may be used seasonally as part of routine and/or preventative healthcare for a subject. In some embodiments, the present assay may be used as part of routine and/or preventative healthcare for subjects who are at particular risk from influenza, such as immunocompromised and elderly subjects.

In some embodiments, a sample to be tested is a nasal aspirate sample or nasal wash sample, or is derived from a nasal aspirate sample or nasal wash sample. In some embodiments, a buffer (such as a preservative) is added to the nasal aspirate sample or nasal wash sample. In some embodiments, the buffer is added to the nasal aspirate sample or nasal wash sample 5 minutes, within 10 minutes, within 30 minutes, within 1 hour, or within 2 hours of sample collection.

In some embodiments, a sample to be tested is a nasopharyngeal swab sample. In some embodiments, the swab is placed in a buffer. In some embodiments, the swab is immediately placed in the buffer. In some embodiments, the swab is placed in the buffer within 5 minutes, within 10 minutes, within 30 minutes, within 1 hour, or within 2 hours of sample collection.

In some embodiments, less than 5 ml, less than 4 ml, less than 3 ml, less than 2 ml, less than 1 ml, or less than 0.75 ml of sample or buffered sample are used in the present methods. In some embodiments, 0.1 ml to 1 ml of sample or buffered sample is used in the present methods.

In some embodiments, the sample to be tested is another bodily fluid, such as saliva, nasal swabs, oropharyngeal swabs, throat swabs, bronchoalveolar lavage samples, bronchial aspirates, bronchial washes, endotracheal aspirates, endotracheal washes, tracheal aspirates, nasal secretion samples, mucus samples, sputum samples, lung tissue samples, etc.

The clinical sample to be tested is, in some embodiments, fresh (i.e., never frozen). In other embodiments, the sample is a frozen specimen. In some embodiments, the sample is a tissue sample, such as a formalin-fixed paraffin embedded sample. In some embodiments, the sample is a liquid cytology sample.

In some embodiments, the sample to be tested is obtained from an individual who has one or more symptoms of influenza infection. Nonlimiting exemplary symptoms of influenza include fever, chills, cough, sore throat, runny nose, nasal congestion, muscle ache, headache, fatigue, vomiting, diarrhea, and combinations of any of those symptoms. In some embodiments, the sample to be tested is obtained from an individual who has previously been diagnosed with influenza. In some such embodiments, the individual is monitored for recurrence of influenza.

In some embodiments, methods described herein can be used for routine screening of healthy individuals with no risk factors. In some embodiments, methods described herein are used to screen asymptomatic individuals, for example, during routine or preventative care. In some embodiments, methods described herein are used to screen women who are pregnant or who are attempting to become pregnant.

In some embodiments, the methods described herein can be used to assess the effectiveness of a treatment for influenza infection in a patient.

In some embodiments, use of the polymerase acidic (PA) gene and/or polymerase basic 2 (PB2) gene for detecting Flu A is provided. In some embodiments, use of the PA gene and/or PB2 gene for detecting Flu A is provided. In some embodiments, use of the PA gene and/or PB2 gene, and optionally, one or more genes selected from the matrix protein (MP) gene and nonstructural protein (NP) gene for detecting Flu A is provided. In some embodiments, use of the PA gene, PB2 gene, MP gene, and NP gene for detecting Flu A and Flu B is provided.

In any of the embodiments described herein, the polymerase acidic (PA) gene and/or polymerase basic 2 (PB2) gene may be detected in the same assay reaction as a sample processing control (SPC).

In some embodiments, a method of facilitating detection of Flu A infection in a subject is provided. Such methods comprise detecting the presence or absence of the Flu A PB2 gene and/or Flu A PA gene in a sample from the subject. In some embodiments, information concerning the presence or absence of the Flu A PB2 gene and/or Flu A PA gene in the sample from the subject is communicated to a medical practitioner. A "medical practitioner," as used herein, refers to an individual or entity that diagnoses and/or treats patients, such as a hospital, a clinic, a physician's office, a physician, a nurse, or an agent of any of the aforementioned entities and individuals. In some embodiments, detecting the presence or absence of the Flu A PB2 gene and/or Flu A PA gene is carried out at a laboratory that has received the subject's sample from the medical practitioner or agent of the medical practitioner. The laboratory carries out the detection by any method, including those described herein, and then communicates the results to the medical practitioner. A result is "communicated," as used herein, when it is provided by any means to the medical practitioner. In some embodiments, such communication may be oral or written, may be by telephone, in person, by e-mail, by mail or other courier, or may be made by directly depositing the information into, e.g., a database accessible by the medical practitioner, including databases not controlled by the medical practitioner. In some embodiments, the information is maintained in electronic form. In some embodiments, the information can be stored in a memory or other computer readable medium, such as RAM, ROM, EEPROM, flash memory, computer chips, digital video discs (DVD), compact discs (CDs), hard disk drives (HDD), magnetic tape, etc.

In some embodiments, methods of detecting Flu A are provided. In some embodiments, methods of diagnosing Flu A infection are provided. In some embodiments, the method comprises obtaining a sample from a subject and providing the sample to a laboratory for detection of the Flu A PB2 gene and/or Flu A PA gene in the sample. In some embodiments, the method further comprises receiving a communication from the laboratory that indicates the presence or absence of the Flu A PB2 gene and/or Flu A PA gene in the sample. A "laboratory," as used herein, is any facility that detects the target gene in a sample by any method, including the methods described herein, and communicates the result to a medical practitioner. In some embodiments, a laboratory is under the control of a medical practitioner. In some embodiments, a laboratory is not under the control of the medical practitioner.

When a laboratory communicates the result of detecting the presence or absence of the Flu A PB2 gene and/or Flu A PA gene to a medical practitioner, in some embodiments, the laboratory indicates whether or not the Flu A PB2 gene and/or Flu A PA gene was detected in the sample. In some embodiments, the laboratory indicates whether the sample comprises Flu A, by indicating, for example, "Flu positive" or "Flu negative" or "Flu present" or "Flu absent," and the like.

As used herein, when a method relates to detecting Flu A, determining the presence of Flu A, monitoring for Flu A, and/or diagnosing Flu A infection, the method includes activities in which the steps of the method are carried out, but the result is negative for the presence of Flu A. That is, detecting, determining, monitoring, and diagnosing Flu A or Flu A infection include instances of carrying out the methods that result in either positive or negative results.

In some embodiments, at least one endogenous control (e.g., an SAC) and/or at least one exogenous control (e.g., an SPC) are detected simultaneously with the Flu A PB2 gene and/or Flu A PA gene in a single reaction. In some embodiments, at least one exogenous control (e.g., an SPC) is detected simultaneously with the Flu A PB2 gene and/or Flu A PA gene in a single reaction.

In any of the embodiments described herein, the Flu A PB2 gene and/or Flu A PA gene may be detected along with one or more additional Flu genes, including but not limited to, Flu A 1 MP, Flu A 2 MP, Flu A 3 haemagglutinin (HA), and Flu B MP. In any of the embodiments described herein, the Flu A PB2 gene and/or Flu A PA gene may be detected along with one or more additional Flu genes such as those listed above, and RSV, such as RSV A and/or RSV B.

4.2.2. Exemplary Controls

In some embodiments, an assay described herein comprises detecting the Flu A PB2 gene and/or Flu A PA gene and at least one endogenous control. In some embodiments, the endogenous control is a sample adequacy control (SAC). In some such embodiments, if neither the Flu A PB2 gene nor Flu A PA gene is detected in a sample, and the SAC is also not detected in the sample, the assay result is considered "invalid" because the sample may have been insufficient. While not intending to be bound by any particular theory, an insufficient sample may be too dilute, contain too little cellular material, contain an assay inhibitor, etc. In some embodiments, the failure to detect an SAC may indicate that the assay reaction failed. In some embodiments, an endogenous control is an RNA (such as an mRNA, tRNA, ribosomal RNA, etc.). Nonlimiting exemplary endogenous controls include ABL mRNA, GUSB mRNA, GAPDH mRNA, TUBB mRNA, and UPK1a mRNA.

In some embodiments, an assay described herein comprises detecting the Flu A PB2 gene and/or Flu A PA gene and at least one exogenous control. In some embodiments, the exogenous control is a sample processing control (SPC). In some such embodiments, if the PB2 gene and/or the PA gene is not detected in a sample, and the SPC is also not detected in the sample, the assay result is considered "invalid" because there may have been an error in sample processing, including but not limited to, failure of the assay. Nonlimiting exemplary errors in sample processing include, inadequate sample processing, the presence of an assay inhibitor, the presence of a nuclease (such as an RNase), compromised reagents, etc. In some embodiments, an exogenous control (such as an SPC) is added to a sample. In some embodiments, an exogenous control (such as an SPC) is added during performance of an assay, such as with one or more buffers or reagents. In some embodiments, when a GeneXpert® system is to be used, the SPC is included in the GeneXpert® cartridge. In some embodiments, an exogenous control (such as an SPC) is an Armored RNA®, which is protected by a bacteriophage coat.

In some embodiments, an endogenous control and/or an exogenous control is detected contemporaneously, such as in the same assay, as detection of the PA gene and/or PB2 gene. In some embodiments, an assay comprises reagents for detecting the PA gene and/or PB2 gene and an exogenous control simultaneously in the same assay reaction. In some such embodiments, for example, an assay reaction comprises a primer set for amplifying the PA gene and/or a primer set for amplifying the PB2 gene, and, a primer set for amplifying an exogenous control, and labeled probes for detecting the amplification products (such as, for example, TaqMan® probes).

4.2.3. Exemplary Sample Preparation
4.2.3.1. Exemplary Buffers

In some embodiments, a buffer is added to the sample. In some embodiments, the buffer is added within one hour, two hours, three hours, or six hours of the time the sample was collected. In some embodiments, a buffer is added to the sample within one hour, two hours, three hours, or six hours before the sample is analyzed by the methods described herein.

In some embodiments, a swab sample is placed in a buffer. In some embodiments, the swab sample is placed in the buffer within one hour, two hours, three hours, or six hours of the time the swab sample was collected. In some embodiments, the swab sample is placed in a buffer within one hour, two hours, three hours, or six hours before the sample is analyzed by the methods described herein.

Non-limiting exemplary commercial buffers include the viral transport medium provided with the GeneXpert® Nasal Pharyngeal Collection Kit (Cepheid, Sunnyvale, Calif.); universal transport medium (UTM™, Copan, Murrieta, Calif.); universal viral transport medium (UVT, BD, Franklin Lakes, N.J.); M4, M$RT, M5, and M6 (Thermo Scientific). Further nonlimiting exemplary buffers include liquid Amies medium, PBS/0.5% BSA, PBS/0.5% gelatin, Bartel BiraTrans™ medium, EMEM, PBS, EMEM/1% BSA, sucrose phosphate, Trypticase™ soy broth (with or without 0.5% gelatin or 0.5% BSA), modified Stuart's medium, veal infusion broth (with or without 0.5% BSA), and saline.

4.2.3.2. Exemplary RNA Preparation

Target RNA can be prepared by any appropriate method. Total RNA can be isolated by any method, including, but not limited to, the protocols set forth in Wilkinson, M. (1988) Nucl. Acids Res. 16(22):10,933; and Wilkinson, M. (1988) Nucl. Acids Res. 16(22): 10934, or by using commercially-available kits or reagents, such as the TRIzol® reagent (Invitrogen), Total RNA Extraction Kit (iNtRON Biotechnology), Total RNA Purification Kit (Norgen Biotek Corp.), RNAqueous™ (Ambion), MagMAX™ (Ambion), RecoverAll™ (Ambion), RNAeasy (Qiagen), etc.

In some embodiments, RNA levels are measured in a sample in which RNA has not first been purified from the cells. In some such embodiments, the cells are subject to a lysis step to release the RNA. Nonlimiting exemplary lysis methods include sonication (for example, for 2-15 seconds, 8-18 µm at 36 kHz); chemical lysis, for example, using a detergent; and various commercially available lysis reagents (such as RNAeasy lysis buffer, Qiagen). In some embodiments, RNA levels are measured in a sample in which RNA has been isolated.

In some embodiments, RNA is modified before a target RNA is detected. In some embodiments, all of the RNA in the sample is modified. In some embodiments, just the particular target RNAs to be analyzed are modified, e.g., in a sequence-specific manner. In some embodiments, RNA is reverse transcribed. In some such embodiments, RNA is reverse transcribed using MMLV reverse transcriptase. Non-limiting exemplary conditions for reverse transcribing RNA using MMLV reverse transcriptase include incubation from 5 to 20 minutes at 40° C. to 50° C.

When a target RNA is reverse transcribed, a DNA complement of the target RNA is formed. In some embodiments, the complement of a target RNA is detected rather than a target RNA itself (or a DNA copy of the RNA itself). Thus, when the methods discussed herein indicate that a target RNA is detected, or the level of a target RNA is determined, such detection or determination may be carried out on a complement of a target RNA instead of, or in addition to, the target RNA itself. In some embodiments, when the complement of a target RNA is detected rather than the target RNA, a polynucleotide for detection is used that is complementary to the complement of the target RNA. In some such embodiments, a polynucleotide for detection comprises at least a portion that is identical in sequence to the target RNA, although it may contain thymidine in place of uridine, and/or comprise other modified nucleotides.

4.2.4. Exemplary Analytical Methods

As described above, methods are presented for detecting influenza, and optionally, respiratory syncytial virus (RSV). The methods comprise detecting the presence of the Flu A polymerase basic 2 (PB2) gene and/or polymerase acidic (PA) gene in a sample from a subject. In some embodiments, the method further comprises detecting one or more additional target genes selected from Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome, and optionally, at least one exogenous control (such as an SPC). In some embodiments, detection of one or more genes selected from Flu A polymerase basic 2 (PB2) gene, polymerase acidic (PA) gene, Flu A 1 matrix protein (MP) gene, Flu A 2 matrix protein (MP) gene, Flu A 3 haemagglutinin (HA) gene, and Flu B nonstructural protein (NS) gene indicates the presence of influenza, even if the endogenous control and/or exogenous control is not detected in the assay. In some embodiments, detection of RSV A or RSV B indicates the presence of RSV, even if the endogenous control and/or exogenous control is not detected in the assay. In some embodiments, if none of the flu target genes (such as the Flu A polymerase basic 2 (PB2) gene, polymerase acidic (PA) gene, Flu A 1 matrix protein (MP) gene, Flu A 2 matrix protein (MP) gene, Flu A 3 haemagglutinin (HA) gene, and Flu B nonstructural protein (NS) gene) is detected, the result is considered to be negative for influenza only if the control detected.

Any analytical procedure capable of permitting specific detection of a target gene may be used in the methods herein presented. Exemplary nonlimiting analytical procedures include, but are not limited to, nucleic acid amplification methods, PCR methods, isothermal amplification methods, and other analytical detection methods known to those skilled in the art.

In some embodiments, the method of detecting a target gene, such as the Flu A 1 matrix protein (MP) gene or Flu A 2 matrix protein (MP) gene, comprises amplifying the gene and/or a complement thereof. Such amplification can be accomplished by any method. Exemplary methods include, but are not limited to, isothermal amplification, real time RT-PCR, endpoint RT-PCR, and amplification using T7 polymerase from a T7 promoter annealed to a DNA, such as provided by the SenseAmp Plus™ Kit available at Implen, Germany.

When a target gene is amplified, in some embodiments, an amplicon of the target gene is formed. An amplicon may be single stranded or double-stranded. In some embodiments, when an amplicon is single-stranded, the sequence of the amplicon is related to the target gene in either the sense or antisense orientation. In some embodiments, an amplicon of a target gene is detected rather than the target gene itself. Thus, when the methods discussed herein indicate that a target gene is detected, such detection may be carried out on an amplicon of the target gene instead of, or in addition to, the target gene itself. In some embodiments, when the amplicon of the target gene is detected rather than the target gene, a polynucleotide for detection is used that is complementary to the complement of the target gene. In some embodiments, when the amplicon of the target gene is detected rather than the target gene, a polynucleotide for detection is used that is complementary to the target gene. Further, in some embodiments, multiple polynucleotides for detection may be used, and some polynucleotides may be complementary to the target gene and some polynucleotides may be complementary to the complement of the target gene.

In some embodiments, the method of detecting a target gene, such as the Flu A 1 matrix protein (MP) gene or Flu A 2 matrix protein (MP) gene, comprises PCR, as described below. In some embodiments, detecting one or more target genes comprises real-time monitoring of a PCR reaction, which can be accomplished by any method. Such methods include, but are not limited to, the use of TaqMan®, molecular beacons, or Scorpion probes (i.e., energy transfer (ET) probes, such as FRET probes) and the use of intercalating dyes, such as SYBR green, EvaGreen, thiazole orange, YO-PRO, TO-PRO, etc.

Nonlimiting exemplary conditions for amplifying a cDNA that has been reverse transcribed from the target RNA are as follows. An exemplary cycle comprises an initial denaturation at 90° C. to 100° C. for 20 seconds to 5 minutes, followed by cycling that comprises denaturation at 90° C. to 100° C. for 1 to 10 seconds, followed by annealing and amplification at 60° C. to 75° C. for 10 to 40 seconds. A further exemplary cycle comprises 20 seconds at 94° C., followed by up to 3 cycles of 1 second at 95° C., 35 seconds at 62° C., 20 cycles of 1 second at 95° C., 20 seconds at 62° C., and 14 cycles of 1 second at 95° C., 35 seconds at 62° C. In some embodiments, for the first cycle following the initial denaturation step, the cycle denaturation step is omitted. In some embodiments, Taq polymerase is used for amplification. In some embodiments, the cycle is carried out at least 10 times, at least 15 times, at least 20 times, at least 25 times, at least 30 times, at least 35 times, at least 40 times, or at least 45 times. In some embodiments, Taq is used with a hot start function. In some embodiments, the amplification reaction occurs in a GeneXpert® cartridge, and amplification of the target genes and an exogenous control occurs in the same reaction. In some embodiments, detection of the target genes occurs in less than 3 hours, less than 2.5 hours, less than 2 hours, less than 1 hour, or less than 30 minutes from initial denaturation through the last extension.

In some embodiments, detection of a target gene comprises forming a complex comprising a polynucleotide that is complementary to a target gene or to a complement thereof, and a nucleic acid selected from the target gene, a DNA amplicon of the target gene, and a complement of the target gene. Thus, in some embodiments, the polynucleotide forms a complex with a target gene. In some embodiments, the polynucleotide forms a complex with a complement of the target RNA, such as a cDNA that has been reverse transcribed from the target RNA. In some embodiments, the polynucleotide forms a complex with a DNA amplicon of the target gene. When a double-stranded DNA amplicon is part of a complex, as used herein, the complex may comprise one or both strands of the DNA amplicon. Thus, in some embodiments, a complex comprises only one strand of the DNA amplicon. In some embodiments, a complex is a triplex and comprises the polynucleotide and both strands of the DNA amplicon. In some embodiments, the complex is formed by hybridization between the polynucleotide and the target gene, complement of the target gene, or DNA amplicon of the target gene. The polynucleotide, in some embodiments, is a primer or probe.

In some embodiments, a method comprises detecting the complex. In some embodiments, the complex does not have to be associated at the time of detection. That is, in some embodiments, a complex is formed, the complex is then dissociated or destroyed in some manner, and components from the complex are detected. An example of such a system is a TaqMan® assay. In some embodiments, when the polynucleotide is a primer, detection of the complex may comprise amplification of the target gene, a complement of the target gene, or a DNA amplicon of the target gene.

In some embodiments the analytical method used for detecting at least one target gene in the methods set forth herein includes real-time quantitative PCR. In some embodiments, the analytical method used for detecting at least one target gene includes the use of a TaqMan® probe. The assay uses energy transfer ("ET"), such as fluorescence resonance energy transfer ("FRET"), to detect and quantitate the synthesized PCR product. Typically, the TaqMan® probe comprises a fluorescent dye molecule coupled to the 5'-end and a quencher molecule coupled to the 3'-end, such that the dye and the quencher are in close proximity, allowing the quencher to suppress the fluorescence signal of the dye via FRET. When the polymerase replicates the chimeric amplicon template to which the TaqMan® probe is bound, the 5'-nuclease of the polymerase cleaves the probe, decoupling the dye and the quencher so that the dye signal (such as fluorescence) is detected. Signal (such as fluorescence) increases with each PCR cycle proportionally to the amount of probe that is cleaved.

In some embodiments, a target gene is considered to be detected if any signal is generated from the TaqMan probe during the PCR cycling. For example, in some embodiments, if the PCR includes 40 cycles, if a signal is generated at any cycle during the amplification, the target gene is considered to be present and detected. In some embodiments, if no signal is generated by the end of the PCR cycling, the target gene is considered to be absent and not detected.

In some embodiments, quantitation of the results of real-time PCR assays is done by constructing a standard curve from a nucleic acid of known concentration and then extrapolating quantitative information for target genes of unknown concentration. In some embodiments, the nucleic acid used for generating a standard curve is a DNA (for example, an endogenous control, or an exogenous control). In some embodiments, the nucleic acid used for generating a standard curve is a purified double-stranded plasmid DNA or a single-stranded DNA generated in vitro.

In some embodiments, in order for an assay to indicate that Flu is not present in a sample, the Ct values for an endogenous control (such as an SAC) and/or an exogenous control (such as an SPC) must be within a previously-determined valid range. That is, in some embodiments, the absence of Flu cannot be confirmed unless the controls are detected, indicating that the assay was successful. In some embodiments, the assay includes an exogenous control. Ct values are inversely proportional to the amount of nucleic acid target in a sample.

In some embodiments, a threshold Ct (or a "cutoff Ct") value for a target gene (including an endogenous control and/or exogenous control), below which the gene is considered to be detected, has previously been determined. In some embodiments, a threshold Ct is determined using substantially the same assay conditions and system (such as a GeneXpert®) on which the samples will be tested.

In addition to the TaqMan® assays, other real-time PCR chemistries useful for detecting and quantitating PCR products in the methods presented herein include, but are not limited to, Molecular Beacons, Scorpion probes and intercalating dyes, such as SYBR Green, EvaGreen, thiazole orange, YO-PRO, TO-PRO, etc., which are discussed below.

In various embodiments, real-time PCR detection is utilized to detect, in a single multiplex reaction, the Flu target genes, and optionally, one or more RSV target genes, an endogenous control, and an exogenous control. In some multiplex embodiments, a plurality of probes, such as TaqMan® probes, each specific for a different target, is used. In some embodiments, each target gene-specific probe is spectrally distinguishable from the other probes used in the same multiplex reaction. A nonlimiting exemplary seven-color multiplex system is described, e.g., in Lee et al., *BioTechniques*, 27: 342-349.

In some embodiments, quantitation of real-time RT PCR products is accomplished using a dye that binds to double-stranded DNA products, such as SYBR Green, EvaGreen, thiazole orange, YO-PRO, TO-PRO, etc. In some embodiments, the assay is the QuantiTect SYBR Green PCR assay from Qiagen. In this assay, total RNA is first isolated from a sample. Total RNA is subsequently poly-adenylated at the 3'-end and reverse transcribed using a universal primer with poly-dT at the 5'-end. In some embodiments, a single reverse transcription reaction is sufficient to assay multiple target RNAs. Real-time RT-PCR is then accomplished using target RNA-specific primers and an miScript Universal Primer, which comprises a poly-dT sequence at the 5'-end. SYBR Green dye binds non-specifically to double-stranded DNA and upon excitation, emits light. In some embodiments, buffer conditions that promote highly-specific annealing of primers to the PCR template (e.g., available in the QuantiTect SYBR Green PCR Kit from Qiagen) can be used to avoid the formation of non-specific DNA duplexes and primer dimers that will bind SYBR Green and negatively affect quantitation. Thus, as PCR product accumulates, the signal from SYBR Green increases, allowing quantitation of specific products.

Real-time PCR is performed using any PCR instrumentation available in the art. Typically, instrumentation used in real-time PCR data collection and analysis comprises a thermal cycler, optics for fluorescence excitation and emission collection, and optionally a computer and data acquisition and analysis software.

In some embodiments, detection and/or quantitation of real-time PCR products is accomplished using a dye that binds to double-stranded DNA products, such as SYBR Green, EvaGreen, thiazole orange, YO-PRO, TO-PRO, etc. In some embodiments, the analytical method used in the methods described herein is a DASL® (DNA-mediated Annealing, Selection, Extension, and Ligation) Assay. In some embodiments, total RNA is isolated from a sample to be analyzed by any method. Total RNA may then be polyadenylated (>18 A residues are added to the 3'-ends of the RNAs in the reaction mixture). The RNA is reverse transcribed using a biotin-labeled DNA primer that comprises from the 5' to the 3' end, a sequence that includes a PCR primer site and a poly-dT region that binds to the poly-dA tail of the sample RNA. The resulting biotinylated cDNA transcripts are then hybridized to a solid support via a biotin-streptavidin interaction and contacted with one or more target RNA-specific polynucleotides. The target RNA-specific polynucleotides comprise, from the 5'-end to the 3'-end, a region comprising a PCR primer site, region comprising an address sequence, and a target RNA-specific sequence.

In some DASL® embodiments, the target RNA-specific sequence comprises at least 8, at least 9, at least 10, at least 11, at least 12, at least 13, at least 14, at least 15, at least 16, at least 17, at least 18, at least 19 contiguous nucleotides having a sequence that is the same as, or complementary to, at least 8, at least 9, at least 10, at least 11, at least 12, at least 13, at least 14, at least 15, at least 16, at least 17, at least 18, at least 19 contiguous nucleotides of a target RNA, an endogenous control RNA, or an exogenous control RNA.

After hybridization, the target RNA-specific polynucleotide is extended, and the extended products are then eluted from the immobilized cDNA array. A second PCR reaction using a fluorescently-labeled universal primer generates a fluorescently-labeled DNA comprising the target RNA-specific sequence. The labeled PCR products are then hybridized to a microbead array for detection and quantitation.

In some embodiments, the analytical method used for detecting and quantifying the target genes in the methods described herein is a bead-based flow cytometric assay. See Lu J. et al. (2005) Nature 435:834-838, which is incorporated herein by reference in its entirety. An example of a bead-based flow cytometric assay is the xMAP® technology of Luminex, Inc. See www.luminexcorp.com/technology/index.html. In some embodiments, total RNA is isolated from a sample and is then labeled with biotin. The labeled RNA is then hybridized to target RNA-specific capture probes (e.g., FlexmiR™ products sold by Luminex, Inc. at www.luminexcorp.com/products/assays/index.html) that are covalently bound to microbeads, each of which is labeled with 2 dyes having different fluorescence intensities. A streptavidin-bound reporter molecule (e.g., streptavidin-phycoerythrin, also known as "SAPE") is attached to the captured target RNA and the unique signal of each bead is read using flow cytometry. In some embodiments, the RNA sample is first polyadenylated, and is subsequently labeled with a biotinylated 3DNA™ dendrimer (i.e., a multiple-arm DNA with numerous biotin molecules bound thereto), using a bridging polynucleotide that is complementary to the 3'-end of the poly-dA tail of the sample RNA and to the 5'-end of the polynucleotide attached to the biotinylated dendrimer. The streptavidin-bound reporter molecule is then attached to the biotinylated dendrimer before analysis by flow cytometry. In some embodiments, biotin-labeled RNA is first exposed to SAPE, and the RNA/SAPE complex is subsequently exposed to an anti-phycoerythrin antibody attached to a DNA dendrimer, which can be bound to as many as 900 biotin molecules. This allows multiple SAPE molecules to bind to the biotinylated dendrimer through the biotin-streptavidin interaction, thus increasing the signal from the assay.

In some embodiments, the analytical method used for detecting and quantifying the levels of the at least one target gene in the methods described herein is by gel electrophoresis and detection with labeled probes (e.g., probes labeled with a radioactive or chemiluminescent label), such as by northern blotting. In some embodiments, total RNA is isolated from the sample, and then is size-separated by SDS polyacrylamide gel electrophoresis. The separated RNA is then blotted onto a membrane and hybridized to radiolabeled complementary probes. In some embodiments, exemplary probes contain one or more affinity-enhancing nucleotide analogs as discussed below, such as locked nucleic acid ("LNA") analogs, which contain a bicyclic sugar moiety instead of deoxyribose or ribose sugars. See, e.g., Várallyay, E. et al. (2008) Nature Protocols 3(2):190-196, which is incorporated herein by reference in its entirety.

In some embodiments, detection and quantification of one or more target genes is accomplished using microfluidic devices and single-molecule detection. In some embodiments, target RNAs in a sample of isolated total RNA are hybridized to two probes, one which is complementary to nucleic acids at the 5'-end of the target RNA and the second which is complementary to the 3'-end of the target RNA. Each probe comprises, in some embodiments, one or more affinity-enhancing nucleotide analogs, such as LNA nucleotide analogs and each is labeled with a different fluorescent dye having different fluorescence emission spectra (i.e., detectably different dyes). The sample is then flowed through a microfluidic capillary in which multiple lasers excite the fluorescent probes, such that a unique coincident burst of photons identifies a particular target RNA, and the number of particular unique coincident bursts of photons can be counted to quantify the amount of the target RNA in the sample. In some alternative embodiments, a target RNA-specific probe can be labeled with 3 or more distinct labels selected from, e.g., fluorophores, electron spin labels, etc., and then hybridized to an RNA sample.

Optionally, the sample RNA is modified before hybridization. The target RNA/probe duplex is then passed through channels in a microfluidic device and that comprise detectors that record the unique signal of the 3 labels. In this way, individual molecules are detected by their unique signal and counted. See U.S. Pat. Nos. 7,402,422 and 7,351,538 to Fuchs et al., U.S. Genomics, Inc., each of which is incorporated herein by reference in its entirety.

4.2.5. Exemplary Automation and Systems

In some embodiments, gene expression is detected using an automated sample handling and/or analysis platform. In some embodiments, commercially available automated analysis platforms are utilized. For example, in some embodiments, the GeneXpert® system (Cepheid, Sunnyvale, Calif.) is utilized.

The present invention is illustrated for use with the GeneXpert system. Exemplary sample preparation and analysis methods are described below. However, the present invention is not limited to a particular detection method or analysis platform. One of skill in the art recognizes that any number of platforms and methods may be utilized.

The GeneXpert® utilizes a self-contained, single use cartridge. Sample extraction, amplification, and detection may all carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.)

Components of the cartridge include, but are not limited to, processing chambers containing reagents, filters, and capture technologies useful to extract, purify, and amplify target nucleic acids. A valve enables fluid transfer from chamber to chamber and contain nucleic acids lysis and filtration components. An optical window enables real-time optical detection. A reaction tube enables very rapid thermal cycling.

In some embodiments, the GeneXpert® system includes a plurality of modules for scalability. Each module includes a plurality of cartridges, along with sample handling and analysis components.

After the sample is added to the cartridge, the sample is contacted with lysis buffer and released DNA is bound to a DNA-binding substrate such as a silica or glass substrate. The sample supernatant is then removed and the DNA eluted in an elution buffer such as a Tris/EDTA buffer. The eluate may then be processed in the cartridge to detect target genes as described herein. In some embodiments, the eluate is used to reconstitute at least some of the PCR reagents, which are present in the cartridge as lyophilized particles.

In some embodiments, RT-PCR is used to amplify and analyze the presence of the target genes. In some embodiments, the reverse transcription uses MMLV RT enzyme and an incubation of 5 to 20 minutes at 40° C. to 50° C. In some embodiments, the PCR uses Taq polymerase with hot start function, such as AptaTaq (Roche). In some embodiments, the initial denaturation is at 90° C. to 100° C. for 20 seconds to 5 minutes; the cycling denaturation temperature is 90° C. to 100° C. for 1 to 10 seconds; the cycling anneal and amplification temperature is 60° C. to 75° C. for 10 to 40 seconds; and up to 50 cycles are performed.

In some embodiments, a double-denature method is used to amplify low copy number targets. A double-denature method comprises, in some embodiments, a first denaturation step followed by addition of primers and/or probes for detecting target genes. All or a substantial portion of the DNA-containing sample (such as a DNA eluate) is then denatured a second time before, in some instances, a portion of the sample is aliquoted for cycling and detection of the target genes. While not intending to be bound by any particular theory, the double-denature protocol may increase the chances that a low copy number target gene (or its complement) will be present in the aliquot selected for cycling and detection because the second denaturation effectively doubles the number of targets (i.e., it separates the target and its complement into two separate templates) before an aliquot is selected for cycling. In some embodiments, the first denaturation step comprises heating to a temperature of 90° C. to 100° C. for a total time of 30 seconds to 5 minutes. In some embodiments, the second denaturation step comprises heating to a temperature of 90° C. to 100° C. for a total time of 5 seconds to 3 minutes. In some embodiments, the first denaturation step and/or the second denaturation step is carried out by heating aliquots of the sample separately. In some embodiments, each aliquot may be heated for the times listed above. As a non-limiting example, a first denaturation step for a DNA-containing sample (such as a DNA eluate) may comprise heating at least one, at least two, at least three, or at least four aliquots of the sample separately (either sequentially or simultaneously) to a temperature of 90° C. to 100° C. for 60 seconds each. As a non-limiting example, a second denaturation step for a DNA-containing sample (such as a DNA eluate) containing enzyme, primers, and probes may comprise heating at least one, at least two, at least three, or at least four aliquots of the eluate separately (either sequentially or simultaneously) to a temperature of 90° C. to 100° C. for 5 seconds each. In some embodiments, an aliquot is the entire DNA-containing sample (such as a DNA eluate). In some embodiments, an aliquot is less than the entire DNA-containing sample (such as a DNA eluate).

In some embodiments, target genes in a DNA-containing sample, such as a DNA eluate, are detected using the following protocol: One or more aliquots of the DNA-containing sample are heated separately to 95° C. for 60 seconds each. The enzyme and primers and probes are added to the DNA-containing sample and one or more aliquots are heated separately to 95° C. for 5 seconds each. At least one aliquot of the DNA-containing sample containing enzyme, primers, and probes is then heated to 94° C. for 60 seconds. The aliquot is then cycled 45 times with the following 2-step cycle: (1) 94° C. for 5 seconds, (2) 66° C. for 30 seconds.

The present invention is not limited to particular primer and/or probe sequences. Exemplary amplification primers and detection probes are described in the Examples.

In some embodiments, an off-line centrifugation is used, for example, with samples with low cellular content. The sample, with or without a buffer added, is centrifuged and the supernatant removed. The pellet is then resuspended in a smaller volume of either supernatant or the buffer. The resuspended pellet is then analyzed as described herein.

4.2.6. Exemplary Data Analysis

In some embodiments, the presence of Flu is detected if the Ct value for any one of the Flu target genes (such as PA, PB2, MP, or NS) is below a certain threshold. In some embodiments the valid range of Ct values is 12 to 39.9 Ct. In some such embodiments, if no amplification above background is observed from the Flu-specific primers after 40 cycles, the sample is considered to be negative for Flu. In some such embodiments, the sample is considered to be negative for Flu only if amplification of the exogenous control (SPC) is above background.

In some embodiments, a computer-based analysis program is used to translate the raw data generated by the detection assay into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample or sputum sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence of Flu) for the subject, with or without recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

4.2.7. Exemplary Polynucleotides

In some embodiments, polynucleotides are provided. In some embodiments, synthetic polynucleotides are provided. Synthetic polynucleotides, as used herein, refer to polynucleotides that have been synthesized in vitro either chemically or enzymatically. Chemical synthesis of polynucleotides includes, but is not limited to, synthesis using polynucleotide synthesizers, such as OligoPilot (GE Healthcare), ABI 3900 DNA Synthesizer (Applied Biosystems), and the like. Enzymatic synthesis includes, but is not limited to, producing polynucleotides by enzymatic amplification, e.g., PCR. A polynucleotide may comprise one or more nucleotide analogs (i.e., modified nucleotides) discussed herein.

In some embodiments, a polynucleotide is provided that comprises a region that is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A polymerase acidic (PA) gene. In some embodiments, a polynucleotide is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A polymerase acidic (PA) gene. Nonlimiting exemplary polynucleotides are shown in Table A.

In some embodiments, a polynucleotide is provided that comprises a region that is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A polymerase basic 2 (PB2) gene. In some embodiments, a polynucleotide is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A polymerase basic 2 (PB2) gene. Nonlimiting exemplary polynucleotides are shown in Table A.

In some embodiments, a polynucleotide is provided that comprises a region that is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome. In some embodiments, a polynucleotide is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome. Nonlimiting exemplary polynucleotides are shown in Table B.

In various embodiments, a polynucleotide comprises fewer than 500, fewer than 300, fewer than 200, fewer than 150, fewer than 100, fewer than 75, fewer than 50, fewer than 40, or fewer than 30 nucleotides. In various embodiments, a polynucleotide is between 6 and 200, between 8 and 200, between 8 and 150, between 8 and 100, between 8 and 75, between 8 and 50, between 8 and 40, between 8 and 30, between 15 and 100, between 15 and 75, between 15 and 50, between 15 and 40, or between 15 and 30 nucleotides long.

In some embodiments, the polynucleotide is a primer. In some embodiments, the primer is labeled with a detectable moiety. In some embodiments, a primer is not labeled. A primer, as used herein, is a polynucleotide that is capable of selectively hybridizing to a target RNA or to a cDNA reverse transcribed from the target RNA or to an amplicon that has been amplified from a target RNA or a cDNA (collectively referred to as "template"), and, in the presence of the template, a polymerase and suitable buffers and reagents, can be extended to form a primer extension product.

In some embodiments, the polynucleotide is a probe. In some embodiments, the probe is labeled with a detectable moiety. A detectable moiety, as used herein, includes both directly detectable moieties, such as fluorescent dyes, and indirectly detectable moieties, such as members of binding pairs. When the detectable moiety is a member of a binding pair, in some embodiments, the probe can be detectable by incubating the probe with a detectable label bound to the second member of the binding pair. In some embodiments, a probe is not labeled, such as when a probe is a capture probe, e.g., on a microarray or bead. In some embodiments, a probe is not extendable, e.g., by a polymerase. In other embodiments, a probe is extendable.

In some embodiments, the polynucleotide is a FRET probe that in some embodiments is labeled at the 5'-end with a fluorescent dye (donor) and at the 3'-end with a quencher (acceptor), a chemical group that absorbs (i.e., suppresses) fluorescence emission from the dye when the groups are in close proximity (i.e., attached to the same probe). Thus, in some embodiments, the emission spectrum of the dye should overlap considerably with the absorption spectrum of the quencher. In other embodiments, the dye and quencher are not at the ends of the FRET probe.

4.2.7.1. Exemplary Polynucleotide Modifications

In some embodiments, the methods of detecting at least one target gene described herein employ one or more polynucleotides that have been modified, such as polynucleotides comprising one or more affinity-enhancing nucleotide analogs. Modified polynucleotides useful in the methods described herein include primers for reverse transcription, PCR amplification primers, and probes. In some embodiments, the incorporation of affinity-enhancing nucleotides increases the binding affinity and specificity of a polynucleotide for its target nucleic acid as compared to polynucleotides that contain only deoxyribonucleotides, and allows for the use of shorter polynucleotides or for shorter regions of complementarity between the polynucleotide and the target nucleic acid.

In some embodiments, affinity-enhancing nucleotide analogs include nucleotides comprising one or more base modifications, sugar modifications and/or backbone modifications.

In some embodiments, modified bases for use in affinity-enhancing nucleotide analogs include 5-methylcytosine, isocytosine, pseudoisocytosine, 5-bromouracil, 5-propynyluracil, 6-aminopurine, 2-aminopurine, inosine, diaminopurine, 2-chloro-6-aminopurine, xanthine and hypoxanthine.

In some embodiments, affinity-enhancing nucleotide analogs include nucleotides having modified sugars such as 2'-substituted sugars, such as 2'-O-alkyl-ribose sugars, 2'-amino-deoxyribose sugars, 2'-fluoro-deoxyribose sugars, 2'-fluoro-arabinose sugars, and 2'-O-methoxyethyl-ribose (2'MOE) sugars. In some embodiments, modified sugars are arabinose sugars, or d-arabino-hexitol sugars.

In some embodiments, affinity-enhancing nucleotide analogs include backbone modifications such as the use of peptide nucleic acids (PNA; e.g., an oligomer including nucleobases linked together by an amino acid backbone). Other backbone modifications include phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

In some embodiments, a polynucleotide includes at least one affinity-enhancing nucleotide analog that has a modified base, at least nucleotide (which may be the same nucleotide) that has a modified sugar, and/or at least one internucleotide linkage that is non-naturally occurring.

In some embodiments, an affinity-enhancing nucleotide analog contains a locked nucleic acid ("LNA") sugar, which is a bicyclic sugar. In some embodiments, a polynucleotide for use in the methods described herein comprises one or more nucleotides having an LNA sugar. In some embodiments, a polynucleotide contains one or more regions consisting of nucleotides with LNA sugars. In other embodiments, a polynucleotide contains nucleotides with LNA sugars interspersed with deoxyribonucleotides. See, e.g., Frieden, M. et al. (2008) Curr. Pharm. Des. 14(11):1138-1142.

4.2.7.2. Exemplary Primers

In some embodiments, a primer is provided. In some embodiments, a primer is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A polymerase acidic (PA) gene. In some embodiments, a primer is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A polymerase acidic (PA) gene. Nonlimiting exemplary primers are shown in Table A. In some embodiments, a primer may also comprise portions or regions that are not identical or complementary to the target gene. In some embodiments, a region of a primer that is at least 90%, at least 95%, or 100% identical or complementary to a target gene is contiguous, such that any region of a primer that is not identical or complementary to the target gene does not disrupt the identical or complementary region.

In some embodiments, a primer is provided. In some embodiments, a primer is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A polymerase basic 2 (PB2) gene. In some embodiments, a primer is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A polymerase basic 2 (PB2) gene. Nonlimiting exemplary primers are shown in Table A. In some embodiments, a primer may also comprise portions or regions that are not identical or complementary to the target gene. In some embodiments, a region of a primer that is at least 90%, at least 95%, or 100% identical or complementary to a target gene is contiguous, such that any region of a primer that is not identical or complementary to the target gene does not disrupt the identical or complementary region.

In some embodiments, a primer is provided. In some embodiments, a primer is at least 90%, at least 95%, or 100% identical to, or at least 90%, at least 95%, or 100% complementary to, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome. In some embodiments, a primer is provided that comprises a region that is at least 90%, at least 95%, or 100% identical to, or complementary to, a span of 6 to 100, 8 to 100, 8 to 75, 8 to 50, 8 to 40, or 8 to 30 contiguous nucleotides of the Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome. Nonlimiting exemplary primers are shown in Table B. In some embodiments, a primer may also comprise portions or regions that are not identical or complementary to the target gene. In some embodiments, a region of a primer that is at least 90%, at least 95%, or 100% identical or complementary to a target gene is contiguous, such that any region of a primer that is not identical or complementary to the target gene does not disrupt the identical or complementary region.

In some embodiments, a primer comprises a portion that is at least 90%, at least 95%, or 100% identical to a region of a target gene. In some such embodiments, a primer that comprises a region that is at least 90%, at least 95%, or 100% identical to a region of the target gene is capable of selectively hybridizing to a cDNA that has been reverse transcribed from the RNA, or to an amplicon that has been produced by amplification of the target gene. In some embodiments, the primer is complementary to a sufficient portion of the cDNA or amplicon such that it selectively hybridizes to the cDNA or amplicon under the conditions of the particular assay being used.

As used herein, "selectively hybridize" means that a polynucleotide, such as a primer or probe, will hybridize to a particular nucleic acid in a sample with at least 5-fold greater affinity than it will hybridize to another nucleic acid present in the same sample that has a different nucleotide sequence in the hybridizing region. Exemplary hybridization conditions are discussed herein, for example, in the context of a reverse transcription reaction or a PCR amplification reaction. In some embodiments, a polynucleotide will hybridize to a particular nucleic acid in a sample with at least 10-fold greater affinity than it will hybridize to another nucleic acid present in the same sample that has a different nucleotide sequence in the hybridizing region.

In some embodiments, a primer is used to reverse transcribe a target RNA, for example, as discussed herein. In some embodiments, a primer is used to amplify a target RNA or a cDNA reverse transcribed therefrom. Such amplification, in some embodiments, is quantitative PCR, for example, as discussed herein.

In some embodiments, a primer comprises a detectable moiety.

In some embodiments, primer pairs are provided. Such primer pairs are designed to amplify a portion of a target gene, such as the Flu A PA gene, Flu A PB2 gene, Flu A 1 matrix protein (MP) gene, Flu A 2 matrix protein (MP) gene, Flu A 3 haemagglutinin (HA) gene, Flu B nonstructural protein (NS) gene, RSV A genome, or RSV B genome, or an endogenous control such as a sample adequacy control (SAC), or an exogenous control such as a sample processing control (SPC). In some embodiments, a primer pair is designed to produce an amplicon that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, 100 to 300 nucleotides long, 100 to 200 nucleotides long, or 100 to 150 nucleotides long. Nonlimiting exemplary primer pairs are shown in Tables A and B.

4.2.7.3. Exemplary Probes

In various embodiments, methods of detecting the presence of influenza, and optionally, RSV, comprise hybridizing nucleic acids of a sample with a probe. In some embodiments, the probe comprises a portion that is complementary to a target gene, such as the he Flu A PA gene or Flu A PB2 gene, or an endogenous control such as a sample adequacy control (SAC), or an exogenous control such as a sample processing control (SPC). In some embodiments, the probe comprises a portion that is at least 90%, at least 95%, or 100% identical to a region of the target gene. In some such embodiments, a probe that is at least 90%, at least 95%, or 100% complementary to a target gene is complementary to a sufficient portion of the target gene such that it selectively hybridizes to the target gene under the conditions of the particular assay being used. In some embodiments, a probe that is complementary to a target gene comprises a region that is at least 90%, at least 95%, or 100% complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the target gene. Nonlimiting exemplary probes are shown in Tables A and B. A probe that is at least 90%, at least 95%, or 100% complementary to a target gene may also comprise portions or regions that are not complementary to the target gene. In some embodiments, a region of a probe that is at least 90%, at least 95%, or 100% complementary to a target gene is contiguous, such that any region of a probe that is not complementary to the target gene does not disrupt the complementary region.

In some embodiments, the probe comprises a portion that is at least 90%, at least 95%, or 100% identical to a region of the target gene, or an endogenous control such as a sample adequacy control (SAC), or an exogenous control such as a sample processing control (SPC). In some such embodiments, a probe that comprises a region that is at least 90%, at least 95%, or 100% identical to a region of the target gene is capable of selectively hybridizing to a cDNA that has been reverse-transcribed from a target gene or to an amplicon that has been produced by amplification of the target gene. In some embodiments, the probe is at least 90%, at least 95%, or 100% complementary to a sufficient portion of the cDNA or amplicon such that it selectively hybridizes to the cDNA or amplicon under the conditions of the particular assay being used. In some embodiments, a probe that is complementary to a cDNA or amplicon comprises a region that is at least 90%, at least 95%, or 100% complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of the cDNA or amplicon. A probe that is at least 90%, at least 95%, or 100% complementary to a cDNA or amplicon may also comprise portions or regions that are not complementary to the cDNA or amplicon. In some embodiments, a region of a probe that is at least 90%, at least 95%, or 100% complementary to a cDNA or amplicon is contiguous, such that any region of a probe that is not complementary to the cDNA or amplicon does not disrupt the complementary region.

In some embodiments, the method of detecting one or more target genes comprises: (a) reverse transcribing a target RNA to produce a cDNA that is complementary to the target RNA; (b) amplifying the cDNA from (a); and (c) detecting the amount of a target RNA using real time RT-PCR and a detection probe (which may be simultaneous with the amplification step (b)).

As described above, in some embodiments, real time RT-PCR detection may be performed using a FRET probe, which includes, but is not limited to, a TaqMan® probe, a Molecular beacon probe and a Scorpion probe. In some embodiments, the real time RT-PCR detection is performed with a TaqMan® probe, i.e., a linear probe that typically has a fluorescent dye covalently bound at one end of the DNA and a quencher molecule covalently bound elsewhere, such as at the other end of, the DNA. The FRET probe comprises a sequence that is complementary to a region of the cDNA or amplicon such that, when the FRET probe is hybridized to the cDNA or amplicon, the dye fluorescence is quenched, and when the probe is digested during amplification of the cDNA or amplicon, the dye is released from the probe and produces a fluorescence signal. In some embodiments, the amount of target gene in the sample is proportional to the amount of fluorescence measured during amplification.

The TaqMan® probe typically comprises a region of contiguous nucleotides having a sequence that is at least 90%, at least 95%, or 100% identical or complementary to a region of a target gene or its complementary cDNA that is reverse transcribed from the target RNA template (i.e., the sequence of the probe region is complementary to or identically present in the target RNA to be detected) such that the probe is selectively hybridizable to a PCR amplicon of a region of the target gene. In some embodiments, the probe comprises a region of at least 6 contiguous nucleotides having a sequence that is fully complementary to or identically present in a region of a cDNA that has been reverse transcribed from a target gene. In some embodiments, the probe comprises a region that is at least 90%, at least 95%, or 100% identical or complementary to at least 8 contiguous nucleotides, at least 10 contiguous nucleotides, at least 12 contiguous nucleotides, at least 14 contiguous nucleotides, or at least 16 contiguous nucleotides having a sequence that is complementary to or identically present in a region of a cDNA reverse transcribed from a target gene to be detected.

In some embodiments, the region of the amplicon that has a sequence that is at least 90%, at least 95%, or 100% complementary to the TaqMan® probe sequence is at or near the center of the amplicon molecule. In some embodiments, there are independently at least 2 nucleotides, such as at least 3 nucleotides, such as at least 4 nucleotides, such as at least 5 nucleotides of the amplicon at the 5'-end and at the 3'-end of the region of complementarity.

In some embodiments, Molecular Beacons can be used to detect PCR products. Like TaqMan® probes, Molecular Beacons use FRET to detect a PCR product via a probe having a fluorescent dye and a quencher attached at the ends of the probe. Unlike TaqMan® probes, Molecular Beacons remain intact during the PCR cycles. Molecular Beacon probes form a stem-loop structure when free in solution, thereby allowing the dye and quencher to be in close enough proximity to cause fluorescence quenching. When the Molecular Beacon hybridizes to a target, the stem-loop structure is abolished so that the dye and the quencher become separated in space and the dye fluoresces. Molecular Beacons are available, e.g., from Gene Link™ (see www.genelink.com/newsite/products/mbintro.asp).

In some embodiments, Scorpion probes can be used as both sequence-specific primers and for PCR product detection. Like Molecular Beacons, Scorpion probes form a stem-loop structure when not hybridized to a target nucleic acid. However, unlike Molecular Beacons, a Scorpion probe achieves both sequence-specific priming and PCR product detection. A fluorescent dye molecule is attached to the 5'-end of the Scorpion probe, and a quencher is attached elsewhere, such as to the 3'-end. The 3' portion of the probe is complementary to the extension product of the PCR primer, and this complementary portion is linked to the 5'-end of the probe by a non-amplifiable moiety. After the Scorpion primer is extended, the target-specific sequence of the probe binds to its complement within the extended amplicon, thus opening up the stem-loop structure and allowing the dye on the 5'-end to fluoresce and generate a signal. Scorpion probes are available from, e.g., Premier Biosoft International (see www.premierbiosoft.com/tech_notes/Scorpion.html).

In some embodiments, labels that can be used on the FRET probes include colorimetric and fluorescent dyes such as Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Examples of dye/quencher pairs (i.e., donor/acceptor pairs) include, but are not limited to, fluorescein/tetramethylrhodamine; IAEDANS/fluorescein; EDANS/dabcyl; fluorescein/fluorescein; BODIPY FL/BODIPY FL; fluorescein/QSY 7 or QSY 9 dyes. When the donor and acceptor are the same, FRET may be detected, in some embodiments, by fluorescence depolarization. Certain specific examples of dye/quencher pairs (i.e., donor/acceptor pairs) include, but are not limited to, Alexa Fluor 350/Alexa Fluor 488; Alexa Fluor 488/Alexa Fluor 546; Alexa Fluor 488/Alexa Fluor 555; Alexa Fluor 488/Alexa Fluor 568; Alexa Fluor 488/Alexa Fluor 594; Alexa Fluor 488/Alexa Fluor 647; Alexa Fluor 546/Alexa Fluor 568; Alexa Fluor 546/Alexa Fluor 594; Alexa Fluor 546/Alexa Fluor 647; Alexa Fluor 555/Alexa Fluor 594; Alexa Fluor 555/Alexa Fluor 647; Alexa Fluor 568/Alexa Fluor 647; Alexa Fluor 594/Alexa Fluor 647; Alexa Fluor 350/QSY 35; Alexa Fluor 350/dabcyl; Alexa Fluor 488/QSY 35; Alexa Fluor 488/dabcyl; Alexa Fluor 488/QSY 7 or QSY 9; Alexa Fluor 555/QSY 7 or QSY 9; Alexa Fluor 568/QSY 7 or QSY 9; Alexa Fluor 568/QSY 21; Alexa Fluor 594/QSY 21; and Alexa Fluor 647/QSY 21. In some instances, the same quencher may be used for multiple dyes, for example, a broad spectrum quencher, such as an Iowa Black® quencher (Integrated DNA Technologies, Coralville, Iowa) or a Black Hole Quencher™ (BHQ™; Sigma-Aldrich, St. Louis, Mo.).

In some embodiments, for example, in a multiplex reaction in which two or more moieties (such as amplicons) are detected simultaneously, each probe comprises a detectably different dye such that the dyes may be distinguished when detected simultaneously in the same reaction. One skilled in the art can select a set of detectably different dyes for use in a multiplex reaction.

Specific examples of fluorescently labeled ribonucleotides useful in the preparation of PCR probes for use in some embodiments of the methods described herein are available from Molecular Probes (Invitrogen), and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences (GE Healthcare), such as Cy3-UTP and Cy5-UTP.

Examples of fluorescently labeled deoxyribonucleotides useful in the preparation of PCR probes for use in the methods described herein include Dinitrophenyl (DNP)-1'-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. Fluorescently labeled nucleotides are commercially available and can be purchased from, e.g., Invitrogen.

In some embodiments, dyes and other moieties, such as quenchers, are introduced into polynucleotide used in the methods described herein, such as FRET probes, via modified nucleotides. A "modified nucleotide" refers to a nucleotide that has been chemically modified, but still functions as a nucleotide. In some embodiments, the modified nucleotide has a chemical moiety, such as a dye or quencher, covalently attached, and can be introduced into a polynucleotide, for example, by way of solid phase synthesis of the polynucleotide. In other embodiments, the modified nucleotide includes one or more reactive groups that can react with a dye or quencher before, during, or after incorporation of the modified nucleotide into the nucleic acid. In specific embodiments, the modified nucleotide is an amine-modified nucleotide, i.e., a nucleotide that has been modified to have a reactive amine group. In some embodiments, the modified nucleotide comprises a modified base moiety, such as uridine, adenosine, guanosine, and/or cytosine. In specific embodiments, the amine-modified nucleotide is selected from 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-(6-Amino)hexyl-ATP; 8-[(6-Amino)hexyl]-amino-ATP; 5-propargylamino-CTP, 5-propargylamino-UTP. In some embodiments, nucleotides with different nucleobase moieties are similarly modified, for example, 5-(3-aminoallyl)-GTP instead of 5-(3-aminoallyl)-UTP. Many amine modified nucleotides are commercially available from, e.g., Applied Biosystems, Sigma, Jena Bioscience and TriLink.

Exemplary detectable moieties also include, but are not limited to, members of binding pairs. In some such embodiments, a first member of a binding pair is linked to a polynucleotide. The second member of the binding pair is linked to a detectable label, such as a fluorescent label. When the polynucleotide linked to the first member of the binding pair is incubated with the second member of the binding pair linked to the detectable label, the first and second members of the binding pair associate and the polynucleotide can be detected. Exemplary binding pairs include, but are not limited to, biotin and streptavidin, antibodies and antigens, etc.

In some embodiments, multiple target genes are detected in a single multiplex reaction. In some such embodiments, each probe that is targeted to a unique amplicon is spectrally distinguishable when released from the probe, in which case each target gene is detected by a unique fluorescence signal. In some embodiments, two or more target genes are detected using the same fluorescent signal, in which case detection of that signal indicates the presence of either of the target genes or both.

One skilled in the art can select a suitable detection method for a selected assay, e.g., a real-time RT-PCR assay. The selected detection method need not be a method described above, and may be any method.

4.3. Exemplary Compositions and Kits

In another aspect, compositions are provided. In some embodiments, compositions are provided for use in the methods described herein.

In some embodiments, compositions are provided that comprise at least one target gene-specific primer. The terms "target gene-specific primer" and "target RNA-specific primer" are used interchangeably and encompass primers that have a region of contiguous nucleotides having a sequence that is (i) at least 90%, at least 95%, or 100% identical to a region of a target gene, or (ii) at least 90%, at least 95%, or 100% complementary to the sequence of a region of contiguous nucleotides found in a target gene. In some embodiments, a composition is provided that comprises at least one pair of target gene-specific primers. The term "pair of target gene-specific primers" encompasses pairs of primers that are suitable for amplifying a defined region of a target gene. A pair of target gene-specific primers typically comprises a first primer that comprises a sequence that is at least 90%, at least 95%, or 100% identical to the sequence of a region of a target gene and a second primer that comprises a sequence that is at least 90%, at least 95%, or 100% complementary to a region of a target gene. A pair of primers is typically suitable for amplifying a region of a target gene that is 50 to 1500 nucleotides long, 50 to 1000 nucleotides long, 50 to 750 nucleotides long, 50 to 500 nucleotides long, 50 to 400 nucleotides long, 50 to 300 nucleotides long, 50 to 200 nucleotides long, 50 to 150 nucleotides long, 100 to 300 nucleotides long, 100 to 200 nucleotides long, or 100 to 150 nucleotides long. Nonlimiting exemplary primers, and pairs of primers, are shown in Tables A and B.

In some embodiments, a composition comprises at least one pair of target gene-specific primers. In some embodiments, a composition additionally comprises a pair of target gene-specific primers for amplifying an endogenous control (such as an SAC) and/or one pair of target gene-specific primers for amplifying an exogenous control (such as an SPC).

In some embodiments, a composition comprises at least one target gene-specific probe. The terms "target gene-specific probe" and "target RNA-specific probe" are used interchangeably and encompass probes that have a region of contiguous nucleotides having a sequence that is (i) at least 90%, at least 95%, or 100% identical to a region of a target gene, or (ii) at least 90%, at least 95%, or 100% complementary to the sequence of a region of contiguous nucleotides found in a target gene. Nonlimiting exemplary target-specific probes are shown in Tables A and B.

In some embodiments, a composition (including a composition described above that comprises one or more pairs of target gene-specific primers) comprises one or more probes for detecting the target genes. In some embodiments, a composition comprises a probe for detecting an endogenous control (such as an SAC) and/or a probe for detecting an exogenous control (such as an SPC).

In some embodiments, a composition is an aqueous composition. In some embodiments, the aqueous composition comprises a buffering component, such as phosphate, tris, HEPES, etc., and/or additional components, as discussed below. In some embodiments, a composition is dry, for example, lyophilized, and suitable for reconstitution by addition of fluid. A dry composition may include one or more buffering components and/or additional components.

In some embodiments, a composition further comprises one or more additional components. Additional components include, but are not limited to, salts, such as NaCl, KCl, and $MgCl_2$; polymerases, including thermostable polymerases such as Taq; dNTPs; reverse transcriptases, such as MMLV reverse transcriptase; Rnase inhibitors; bovine serum albumin (BSA) and the like; reducing agents, such as β-mercaptoethanol; EDTA and the like; etc. One skilled in the art can select suitable composition components depending on the intended use of the composition.

In some embodiments, compositions are provided that comprise at least one polynucleotide for detecting at least one target gene. In some embodiments, the polynucleotide is used as a primer for a reverse transcriptase reaction. In some embodiments, the polynucleotide is used as a primer for amplification. In some embodiments, the polynucleotide is used as a primer for PCR. In some embodiments, the polynucleotide is used as a probe for detecting at least one target gene. In some embodiments, the polynucleotide is detectably labeled. In some embodiments, the polynucleotide is a FRET probe. In some embodiments, the polynucleotide is a TaqMan® probe, a Molecular Beacon, or a Scorpion probe.

In some embodiments, a composition comprises at least one FRET probe having a sequence that is at least 90%, at least 95%, or 100% identical, or at least 90%, at least 95%, or 100% complementary, to a region of, a target gene, such as the Flu A PA gene or Flu A PB2 gene. In some embodiments, a FRET probe is labeled with a donor/acceptor pair such that when the probe is digested during the PCR reaction, it produces a unique fluorescence emission that is associated with a specific target gene. In some embodiments, when a composition comprises multiple FRET probes, each probe is labeled with a different donor/acceptor pair such that when the probe is digested during the PCR reaction, each one produces a unique fluorescence emission that is associated with a specific probe sequence and/or target gene. In some embodiments, the sequence of the FRET probe is complementary to a target region of a target gene. In other embodiments, the FRET probe has a sequence that comprises one or more base mismatches when compared to the sequence of the best-aligned target region of a target gene.

In some embodiments, a composition comprises a FRET probe consisting of at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides, wherein at least a portion of the sequence is at least 90%, at least 95%, or 100% identical, or at least 90%, at least 95%, or 100% complementary, to a region of, a target gene, such as the Flu A PA gene or Flu A PB2 gene. In some embodiments, at least 8, at least 9, at least 10, at least 11, at least 13, at least 14, at least 15, at least 16, at least 17, at least 18, at least 19, at least 20, at least 21, at least 22, at least 23, at least 24, or at least 25 nucleotides of the FRET probe are identically present in, or complementary to a region of, a target gene, such as the Flu A PA gene or Flu A PB2 gene. In some embodiments, the FRET probe has a sequence with one, two or three base mismatches when compared to the sequence or complement of the target gene.

In some embodiments, a kit comprises a polynucleotide discussed above. In some embodiments, a kit comprises at least one primer and/or probe discussed above. In some embodiments, a kit comprises at least one polymerase, such as a thermostable polymerase. In some embodiments, a kit comprises dNTPs. In some embodiments, kits for use in the real time RT-PCR methods described herein comprise one or more target gene-specific FRET probes and/or one or more primers for reverse transcription of target RNAs and/or one or more primers for amplification of target genes or cDNAs reverse transcribed therefrom.

In some embodiments, one or more of the primers and/or probes is "linear". A "linear" primer refers to a polynucleotide that is a single stranded molecule, and typically does not comprise a short region of, for example, at least 3, 4 or 5 contiguous nucleotides, which are complementary to another region within the same polynucleotide such that the primer forms an internal duplex. In some embodiments, the primers for use in reverse transcription comprise a region of at least 4, such as at least 5, such as at least 6, such as at least 7 or more contiguous nucleotides at the 3'-end that has a sequence that is complementary to region of at least 4, such as at least 5, such as at least 6, such as at least 7 or more contiguous nucleotides at the 5'-end of a target gene.

In some embodiments, a kit comprises one or more pairs of linear primers (a "forward primer" and a "reverse primer") for amplification of a target gene or cDNA reverse transcribed therefrom. Accordingly, in some embodiments, a first primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is at least 90%, at least 95%, or 100% identical to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a first location in the target gene. Furthermore, in some embodiments, a second primer comprises a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides having a sequence that is at least 90%, at least 95%, or 100% complementary to the sequence of a region of at least 8, at least 9, at least 10, at least 11, at least 12, at least 13, at least 14, at least 15, at least 16, at least 17, at least 18, at least 19, at least 20, at least 21, at least 22, at least 23, at least 24, or at least 25 contiguous nucleotides at a second location in the target gene, such that a PCR reaction using the two primers results in an amplicon extending from the first location of the target gene to the second location of the target gene.

In some embodiments, the kit comprises at least two, at least three, or at least four sets of primers, each of which is for amplification of a different target gene or cDNA reverse transcribed therefrom. In some embodiments, the kit further comprises at least one set of primers for amplifying a control RNA, such as an endogenous control and/or an exogenous control.

In some embodiments, probes and/or primers for use in the compositions described herein comprise deoxyribonucleotides. In some embodiments, probes and/or primers for use in the compositions described herein comprise deoxyribonucleotides and one or more nucleotide analogs, such as LNA analogs or other duplex-stabilizing nucleotide analogs described above. In some embodiments, probes and/or primers for use in the compositions described herein comprise all nucleotide analogs. In some embodiments, the probes and/or primers comprise one or more duplex-stabilizing nucleotide analogs, such as LNA analogs, in the region of complementarity.

In some embodiments, the kits for use in real time RT-PCR methods described herein further comprise reagents for use in the reverse transcription and amplification reactions. In some embodiments, the kits comprise enzymes, such as a reverse transcriptase or a heat stable DNA polymerase, such as Taq polymerase. In some embodiments, the kits further comprise deoxyribonucleotide triphosphates (dNTP) for use in reverse transcription and/or in amplification. In further embodiments, the kits comprise buffers optimized for specific hybridization of the probes and primers.

A kit generally includes a package with one or more containers holding the reagents, as one or more separate compositions or, optionally, as an admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits preferably include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In some embodiments, the kit can comprise the reagents described above provided in one or more GeneXpert® cartridge(s). These cartridges permit extraction, amplification, and detection to be carried out within this self-contained "laboratory in a cartridge." (See e.g., U.S. Pat. Nos. 5,958,349, 6,403,037, 6,440,725, 6,783,736, 6,818,185; each of which is herein incorporated by reference in its entirety.) Reagents for measuring genomic copy number level and detecting a pathogen could be provided in separate cartridges within a kit or these reagents (adapted for multiplex detection) could be provide in a single cartridge.

Any of the kits described here can include, in some embodiments, a receptacle for a nasal aspirate/wash sample and/or a swab for collecting a nasopharyngeal swab sample.

The following examples are for illustration purposes only, and are not meant to be limiting in any way.

5. EXAMPLES

5.1. Example 1: Detection of Influenza A (FluA)

Many existing Flu tests rely on detection of the Flu matrix protein (MP) gene. The constant antigenic drift and shift of influenza viruses make it difficult to maintain assay sensitivity from season to season, resulting in a degradation of assay performance over time. In order to design a robust influenza assay that is less likely to lose sensitivity, or loses sensitivity at a slower rate than existing tests, additional Flu A targets that could complement MP were investigated.

Suitable gene fragments for the design of primers and probes were identified by first generating sequence alignments of RNA segments using the European Molecular Biology Laboratory (EMBL)-European Bioinformatics Institute (EBI) sequence alignment software, ClustalW. ClustalW is a general purpose multiple sequence alignment program for nucleic acids or proteins that calculates the best match for the selected sequences and aligns them such that the identities, similarities, and differences can be compared. For each potential target, sequence regions, 100-200 nt in length, were chosen that differentiated the targets. The regions were also selected based on the frequency of polymorphic base substitutions; regions were selected that were highly conserved.

Design of primers and probes for amplification of RNA fragments in the selected regions was performed using DNA Software, Inc.'s Visual OMP (Oligonucleotide Modeling Platform). Visual OMP models, in silico, the folding and hybridization of single-stranded nucleic acids by incorporating all public domain thermodynamic parameters as well as proprietary nearest-neighbor and multi-state thermodynamic parameters for DNA, RNA, PNA, and Inosine. This enables the effective design of primers and probes for complex assays such as microarrays, microfluidics applications and multiplex PCR. In silico experiments simulate secondary structures for targets (optimal and suboptimal), primers (optimal and suboptimal), homodimers, and target and primer heterodimers, given specified conditions. Values for melting temperature (Tm), free energy (ΔG), percent bound, and concentrations for all species are calculated. Additionally, Visual OMP predicts the binding efficiency between primers and probes with target(s) in a single or multiplex reaction.

Using this software tool, predicted interactions between oligonucleotides and the different Flu targets were evaluated thermodynamically and unwanted interactions were minimized.

The selected primers and probes were then subjected to BLAST searching. Oligos were queried singly and in combinations representing the expected full-length amplicon sequences.

Based on this analysis, two new Flu A target genes were identified that could improve the sensitivity of existing influenza assay: the polymerase basic 2 (PB2) gene and the polymerase acidic (PA) gene. Exemplary PB2 and PA gene sequences are shown in SEQ ID NOs: 1 and 2, respectively. Primers and probes for detecting two new Flu A target genes were designed as described above, and are shown in Table A.

TABLE A

Primers and Probes for Detecting Flu A 1 PB2 and PA Genes

| Target | Description | Sequence | SEQ ID NO | Amplicon SEQ ID NO |
|---|---|---|---|---|
| Flu A 1 PB2 | A PB2 forward | AAACGGGACTCTAGCATACT | 17 | 8 |
| | A PB2 reverse | TAATTGATGGCCATCCGAAT | 18 | |
| | A PB2 probe | F1-AGCCAGACAGCGACCAAAAG-Q1 | 19 | |
| Flu A 1 PA | A PA forward | ATCTTGGGGGGCTATATGAAGCAAT | 20 | 9 |
| | A PA reverse | AGGAAGGAGTTGAACCAAGA | 21 | |
| | A PA probe | F1-AATGATCCCTGGGTTTTGCT-Q1 | 22 | |

In addition, primers and probes were designed as described above to detect the Flu A 1 matrix protein (MP) gene, Flu A 2 (avian isolates) MP gene, Flu A 3 (H7N9) haemagglutinin (HA) gene, Flu B MP gene, Flu B NS gene, and respiratory syncytial virus (RSV) A and B. Exemplary Flu A 1 MP, Flu A 2 MP, Flu A 3 HA, Flu B MP, and Flu B NS gene sequences are shown in SEQ ID NOs: 3 to 7, respectively. Those primers and probes are shown in Table B.

TABLE B

Primers and Probes for Detecting Flu A 1 MP, Flu A 2 MP, Flu A 3 HA, Flu B MP, Flu B NS, RSV A, and RSV B

| Target | Description | Sequence | SEQ ID NO | Amplicon SEQ ID NO |
|---|---|---|---|---|
| Flu A 1 MP | A MP forward | TTCTAACCGAGGTCGAAACG | 23 | 10 |
| | A MP reverse | ATTGGTCTTGTCTTTAGCCA | 24 | |
| | A MP probe | F1-TCAGGCCCCCTCAAAGCCGA-Q1 | 25 | |
| Flu A 2 MP | Avian MP forward | CAAGACCAATCCTGTCACCT | 26 | 11 |
| | Avian MP reverse | CGTCTACGCTGCAGTCCTCG | 27 | |
| | Avian MP probe | F2-ACGCTCACCGTGCCCAGTGA-Q1 | 28 | |
| Flu A 3 HA | H7N9 HA forward | GAAATGAAATGGCTCCTGTC | 29 | 12 |
| | H7N9 HA reverse | GGCTTTTTCTTGTATTTTTATATGA | 30 | |
| | H7N9 HA probe | F3-CTGCATTCCCGCAGATGAC-Q2 | 31 | |
| Flu B MP | B MP forward | TTGGAGACACGATTGCCTAC | 32 | 13 |
| | B MP reverse | AGGTCAAATTCTTTCCCACC | 33 | |
| | B MP probe | F4-ATGGAGAAGGCAAAGCAGAA-Q1 | 34 | |
| Flu B NS | B NS forward | GATGGCCATCGGATCCTCAA | 35 | 14 |
| | B NS reverse | GCTCTTGACCAAATTGGGAT | 36 | |
| | B NS probe | F4-AAAGCCAATTCGAGCAGCTG-Q1 | 37 | |

TABLE B-continued Primers and Probes for Detecting Flu A 1 MP, Flu A 2 MP, Flu A 3 HA, Flu B MP, Flu B NS, RSV A, and RSV B

| Target | Description | Sequence | SEQ ID NO | Amplicon SEQ ID NO |
|---|---|---|---|---|
| RSV A | RSV A forward | TACACTCAACAAAGATCAACTTCTGTC | 38 | 15 |
|  | RSV A reverse | CATGCCACATAACTTATTGATGTGT | 39 |  |
|  | RSV A probe | F5-CACCATCCAACGGAGCACAGGAGA-Q1 | 40 |  |
| RSV B | RSV B forward | CATTAAATAAGGATCAGCTGCTGTC | 41 | 16 |
|  | RSV B reverse | GCATACCACATAGTTTGTTTAGGTGTT | 42 |  |
|  | RSV B probe | F5-TAATATTGACACTCCCAATTATGATGTGC-Q1 | 43 |  |

F1, F2, F3, F4, and F5 are detectably different dyes that can be detected and distinguished simultaneously in a multiplex reaction. Each probe also comprises a quencher (e.g., Q1 or Q2, above).

The final primer and probe compositions of the multiplex assay are shown in Table B.

TABLE B

Primer and probe concentrations

| Target | Label | Purpose | Final conc. forw. Primer (μM) | Final conc. Rev. primer (μM) | Final conc. Probe (μM) |
|---|---|---|---|---|---|
| Flu A 1 PB2 | F1 | Flu A 1 | 0.8 | 0.4 | 0.1 |
| Flu A 1 PA | F2 | Flu A 1 | 0.4 | 0.8 | 0.1 |
| Flu A 1 MP | F2 | Flu A 1 | 0.8 | 0.8 | 0.1 |
| Flu A 2 MP | F2 | Avian Flu | 0.8 | 0.4 | 0.2 |
| Flu A 3 HA | F3 | H7N9 | 0.8 | 0.8 | 0.4 |
| Flu B MP | F4 | Flu B | 0.2 | 0.8 | 0.1 |
| Flu B NS | F4 | Flu B | 0.8 | 0.4 | 0.1 |
| RSV A | F5 | RSV | 0.8 | 0.8 | 0.1 |
| RSV B | F5 | RSV | 0.4 | 0.8 | 0.2 |
| Armored® RNA | F6 | SPC | 0.8 | 0.8 | 0.4 |

Each reaction contained 50-90 mM KCl, 3-5 mM MgCl$_2$, 400-825 μM dNTPs, 20 mM Tris, pH 8.5, 0.01% sodium azide, and 1 units/μl of RNase inhibitor. MMLV reverse transcriptase (2 units/μl) and AptaTaq (3 units/μl; Roche) were used for reverse transcription and amplification, respectively.

For NP swabs, the swab sample is placed in a tube containing 3 mL of transport medium. For NA/W samples, 600 μL NA/W sample is added to 3 mL transport medium.

300 μL of buffered nasopharyngeal swab (NP) or nasal aspirate/wash sample (NA/W) sample was loaded into a GeneXpert® cartridge for analysis. The sample was mixed with a lysis reagent to release nucleic acids. After lysis, the released nucleic acid from the sample was captured on a DNA-binding substrate. The nucleic acid was eluted from the substrate and used to reconstitute the reagents used for real-time PCR (described above). The reaction cycle used was: 20 seconds at 94° C., followed by up to 3 cycles of 1 second at 95° C., 35 seconds at 62° C., 20 cycles of 1 second at 95° C., 20 seconds at 62° C., and 14 cycles of 1 second at 95° C., 35 seconds at 62° C. using a GeneXpert® cartridge in a GeneXpert® system.

The valid range of Ct values for the targets was 12-39.9 Ct.

The Xpert Flu/RSV XC Assay has three channels (Flu A 1, Flu A 2, and Flu A 3) to detect most influenza A strains. The primers and probes in the Flu A 1 channel have 100% homology to human influenza A strains. The primers and probes in the Flu A 2 channel have >95% homology to avian influenza A strains and approximately 80% homology to human influenza A strains. The primers and probes in the Flu A 3 channel detect the hemagglutinin gene segment for the avian influenza A H7N9 strains (subtyping capability). All influenza A strains (human and avian) detected by the Xpert Flu/RSV XC Assay are reported as Flu A POSITIVE.

The Flu A result call algorithm in the Xpert Flu/RSV XC Assay requires either the Flu A 1 or Flu A 2 channel to be positive in order for a Flu A POSITIVE test result to be reported. A positive in the Flu A 3 channel without a positive Flu A 1 or Flu A 2 result is reported as INVALID. Table 1 below lists all the possible test results for Flu A.

TABLE 1

Possible Test Results for Flu A for A 1, Flu A 2, and Flu A 3 Channels

| Flu A Test Result | Flu A 1 Channel | Flu A 2 Channel | Flu A 3 Channel |
|---|---|---|---|
| Flu A POSITIVE | POS | POS | POS |
|  | POS | POS | NEG |
|  | POS | NEG | POS |
|  | NEG | POS | POS |
|  | POS | NEG | NEG |
|  | NEG | POS | NEG |
| INVALID | NEG | NEG | POS |
| Flu A NEGATIVE | NEG | NEG | NEG |

All the possible results are shown in Tables 2 and 3.

TABLE 2

All Possible Final Test Results for the Xpert Flu-RSV XC Selected Assay

| Result Text | Flu A 1 | Flu A 2 | Flu A 3 | Flu B | RSV | SPC |
|---|---|---|---|---|---|---|
| Flu A POSITIVE; Flu B NEGATIVE; RSV NEGATIVE | +/− | +/− | +/− | − | − | +/− |
| Flu A NEGATIVE; Flu B POSITIVE; RSV NEGATIVE | − | − | − | + | − | +/− |
| Flu A NEGATIVE; Flu B NEGATIVE; RSV POSITIVE | − | − | − | − | + | +/− |
| Flu A POSITIVE; Flu B POSITIVE; RSV NEGATIVE | +/− | +/− | +/− | + | − | +/− |
| Flu A POSITIVE; Flu B NEGATIVE; RSV POSITIVE | +/− | +/− | +/− | − | + | +/− |

TABLE 2-continued

All Possible Final Test Results for the Xpert Flu-RSV XC Selected Assay

| Result Text | Flu A 1 | Flu A 2 | Flu A 3 | Flu B | RSV | SPC |
|---|---|---|---|---|---|---|
| Flu A NEGATIVE; Flu B POSITIVE; RSV POSITIVE | − | − | − | + | + | +/− |
| Flu A POSITIVE; Flu B POSITIVE; RSV POSITIVE | +/− | +/− | +/− | + | + | +/− |
| Flu A NEGATIVE; Flu B NEGATIVE; RSV NEGATIVE | − | − | − | − | − | + |
| INVALID | − | − | − | − | − | − |

TABLE 3

Xpert Flu-RSV XC Assay Results and Interpretations

| Result | Interpretation |
|---|---|
| Flu A POSITIVE; Flu B NEGATIVE; RSV NEGATIVE | Flu A target RNA is detected; Flu B target RNA is not detected; RSV target RNA is not detected. The Flu A target has a Ct within the valid range and endpoint above the threshold setting. SPC: NA (not applicable); SPC is ignored because the Flu A target amplification may compete with this control. Probe Check: PASS: all probe check results pass. |
| Flu A NEGATIVE; Flu B POSITIVE; RSV NEGATIVE | Flu A target RNA is not detected; Flu B target RNA is detected; RSV target RNA is not detected. The Flu B target has a Ct within the valid range and endpoint above the threshold setting. SPC: NA (not applicable); SPC is ignored because the Flu B target amplification may compete with this control. Probe Check: PASS: all probe check results pass. |
| Flu A NEGATIVE; Flu B NEGATIVE; RSV POSITIVE | Flu A target RNA is not detected; Flu B target RNA is not detected; RSV target RNA is detected. The RSV target has a Ct within the valid range and endpoint above the threshold setting. SPC: NA (not applicable); SPC is ignored because the RSV target amplification may compete with this control. Probe Check: PASS; all probe check results pass. |
| Flu A POSITIVE; Flu B POSITIVE; RSV NEGATIVE | Flu A target RNA is detected; Flu B target RNA is detected; RSV target RNA is not detected. The Flu A target has a Ct within the valid range and endpoint above the threshold setting. The Flu B target has a Ct within the valid range and endpoint above the threshold setting. SPC: NA (not applicable); SPC is ignored because the Flu A and Flu B target amplification may compete with this control. Probe Check: PASS; all probe check results pass. |
| Flu A POSITIVE; Flu B NEGATIVE; RSV POSITIVE | Flu A target RNA is detected; Flu B target RNA is not detected; RSV target RNA is detected. The Flu A target has a Ct within the valid range and endpoint above the threshold setting. The RSV target has a Ct within the valid range and endpoint above the threshold setting. SPC: NA (not applicable); SPC is ignored because the Flu A and RSV target amplification may compete with this control. Probe Check: PASS; all probe check results pass. |
| Flu A NEGATIVE; Flu B POSITIVE; RSV POSITIVE | Flu A target RNAis not detected; Flu B target RNA is detected RSV target RNA is detected. The Flu B target has a Ct within the valid range and endpoint above the threshold setting. The RSV target has a Ct within the valid range and endpoint above the threshold setting. SPC: NA (not applicable); SPC is ignored because the Flu B and RSV target amplification may compete wtth this control. Probe Check: PASS: all probe check results pass. |
| Flu A POSITIVE: Flu B POSITIVE; RSV POSITIVE | Flu A target RNA is detected; Flu B target RNA is detected; RSV target RNA is detected. The Flu A target has a Ct within the valid range and endpoint above the threshold setting. The Flu B target has a Ct within the valid range add endpoint above the threshold setting. The RSV target has a Ct within the valid range and endpoint above the threshold setting. SPC: NA (not applicable) SPC is ignored because the Flu A, Flu B, and RSV target amplification may compete with this control. Probe Check: PASS, all probe check results pass. |
| Flu A NEGATIVE; Flu B NEGATIVE; RSV NEGATIVE | Flu A target RNA is not detected; Flu B target RNA is not detected; RSV target RNA is not detected. Flu A, Flu B, and RSV target RNAs are not detected. SPC: PASS; SPC has a Ct within the valid range and endpoint above the threshold setting. Probe Check: PASS; all probe check results pass. |
| INVALID | SPC does not meet acceptance criteria. Presence or absence of the target RNAs cannot be determined. Repeat test according to the instructions in Section 16.2, Retest Procedure below. Testing specimens that contain high viral titers of influenza A or influenza B in the Xpert RSV only assay mode may lead to invalid results. It is recommended that these specimens should be re-tested in the Xpert Flu-RSV XC assay mode to obtain a valid result. Testing specimens that contain high viral titers of RSV in the Xpert Flu XC only assay mode may lead to invalid results. It is recommended that these specimens should be re-tested in the Xpert Flu-RSV XC assay mode to obtain a valid result. SPC meets acceptance criteria. Flu A1, Flu A2, Flu B, and RSV target RNAs are not detected; Flu A3 target RNA is detected. |

TABLE 3-continued

Xpert Flu-RSV XC Assay Results and Interpretations

| Result | Interpretation |
| --- | --- |
| ERROR | Presence or absence of Flu A, Flu B, and/or RSV target RNA cannot be determined. Repeat test according to the instructions in Section 16.2, Retest Procedure below.<br>Flu A: NO RESULT<br>Flu B: NO RESULT<br>RSV: NO RESULT<br>SPC: NO RESULT<br>Probe Check: FAIL*; all or one of the probe check results fail.<br>If the probe check passed; the error is caused by the maximum pressure limit exceeding the acceptable range or by a system component failure. |
| NO RESULT | Presence or absence of Flu A, Flu B, and/or RSV target RNA cannot be determined. Repeat test according to the instructions in Section 16.2, Retest Procedure below. A NO RESULT indicates that insufficient data were collected. For example, the operator stopped a test that was in progress or a power failure occurred.<br>Flu A: NO RESULT<br>Flu B: NO RESULT<br>RSV: NO RESULT<br>SPC: NO RESULT<br>Probe Check: NA (not applicable) |

5.2. Example 2: Clinical Performance

Performance characteristics of the Xpert Flu/RSV XC Assay were evaluated at six institutions in the U.S. Due to the low prevalence of influenza viruses and the difficulty in obtaining fresh influenza and RSV-positive specimens, the specimen population for this study was supplemented with frozen archived specimens.

Subjects included individuals with signs and symptoms of respiratory infection and whose routine care called for collection of nasal aspirate/wash (NA/W) specimens or nasopharyngeal (NP) swab specimens for influenza and RSV testing. For eligible subjects, aliquots of leftover specimens were obtained for testing with the Xpert Flu/RSV XC Assay and reference testing, and patient management continued at the site per their standard practice.

The Xpert Flu/RSV XC Assay performance was compared to a FDA-cleared comparator assay. Bi-directional sequencing was performed on specimens where the Xpert Flu/RSV XC Assay and the comparator assay were discrepant.

5.2.1. Nasal Aspirate/Wash (NA/W) Samples

A total of 657 NA/W specimens were tested for influenza A, influenza B and RSV by the Xpert Flu/RSV XC Assay and the reference assay. Of the 657 NA/W specimens, 581 were fresh, prospectively collected and 76 were frozen, archived specimens.

Overall, with NA/W specimens the Xpert Flu/RSV XC Assay demonstrated positive percent agreement (PPA), negative percent agreement (NPA), and overall percent agreement (OPA) for detection of influenza A of 98.6%, 100% and 99.8%, respectively relative to the reference assay (Table 4). The Xpert Flu/RSV XC Assay PPA, NPA, and OPA for influenza B were 99.2%, 100%, and 99.8%, respectively (Table 4). The Xpert Flu/RSV XC Assay PPA, NPA, and OPA for RSV were 97.2%, 99.6%, and 99.1%, respectively (Table 4).

On fresh, prospectively collected NA/W specimens, the Xpert Flu/RSV XC Assay demonstrated a PPA, NPA, and OPA for detection of influenza A of 100%, 100%, and 100% respectively, relative to the reference assay (Table 4). The Xpert Flu/RSV XC Assay PPA, NPA, and OPA for influenza B were 99.2%, 100%, and 99.8%, respectively (Table 4). The Xpert Flu/RSV XC Assay PPA, NPA, and OPA for RSV were 98.5%, 99.6%, and 99.3%, respectively (Table 4).

On frozen, archived NA/W specimens, the Xpert Flu/RSV XC Assay demonstrated a PPA, NPA, and OPA for detection of influenza A of 97.1%, 100%, and 98.7%, respectively, relative to the reference assay (Table 4). The Xpert Flu/RSV XC Assay PPA, NPA, and OPA for influenza B were 100%, 100%, and 100%, respectively (Table 4). The Xpert Flu/RSV XC Assay PPA, NPA, and OPA for RSV were 84.6%, 100%, and 97.4%, respectively (Table 4).

TABLE 4

Xpert Flu/RSV XC Assay Performance on NA/W Specimens

| Specimen Type | Target | n | TP | FP | TN | FN | PPA % (95 CI) | NPA % (95 CI) | OPA % (95 CI) |
| --- | --- | --- | --- | --- | --- | --- | --- | --- | --- |
| Fresh | Flu A | 581 | 35 | 0 | 546 | 0 | 100 (90.0-100) | 100 (99.3-100) | 100 (99.4-100) |
|  | Flu B | 581 | 126 | 0 | 454 | $1^a$ | 99.2 (95.7-100) | 100 (99.2-100) | 99.8 (99.0-100) |
|  | RSV | 581 | 128 | $2^b$ | 449 | $2^c$ | 98.5 (94.6-99.8) | 99.6 (98.4-99.9) | 99.3 (98.2-99.8) |
| Frozen | Flu A | 76 | 34 | 0 | 41 | $1^d$ | 97.1 (85.1-99.9) | 100 (91.4-100) | 98.7 (92.9-100) |
|  | Flu B | 76 | 1 | 0 | 75 | 0 | 100 (2.5-100) | 100 (95.2-100) | 100 (95.3-100) |
|  | RSV | 76 | 11 | 0 | 63 | $2^e$ | 84.6 (54.6-98.1) | 100 (94.3-100) | 97.4 (90.8-99.7) |

TABLE 4-continued

Xpert Flu/RSV XC Assay Performance on NA/W Specimens

| Specimen Type | Target | n | TP | FP | TN | FN | PPA % (95 CI) | NPA % (95 CI) | OPA % (95 CI) |
|---|---|---|---|---|---|---|---|---|---|
| All NA/W Specimens | Flu A | 657 | 69 | 0 | 587 | 1[f] | 98.6 (92.3-100) | 100 (99.4-100) | 99.8 (99.2-100) |
| | Flu B | 657 | 127 | 0 | 529 | 1[g] | 99.2 (95.7-100) | 100 (99.3-100) | 99.8 (99.2-100) |
| | RSV | 657 | 139 | 2[h] | 512 | 4[i] | 97.2 (93.0-99.2) | 99.6 (98.6-100) | 99.1 (98.0-99.7) |

[a]Testing results by sequencing: NA; sample not sequenced.
[b]Testing results by sequencing: 2 of 2 were RSV Positive.
[c]Testing results by sequencing: 1 of 2 was RSV Positive; 1 of 2 was RSV Negative.
[d]Testing results by sequencing: 1 of 1 was Flu A Negative.
[e]Testing results by sequencing: 1 of 2 was RSV Positive; 1 of 2 was RSV Negative.
[f]Testing results by sequencing: 1 of 1 was Flu A Negative.
[g]Testing results by sequencing: NA; sample not sequenced.
[h]Testing results by sequencing: 2 of 2 were RSV Positive.
[i]Testing results by sequencing: 2 of 4 were RSV Positive; 2 of 4 were RSV Negative.

5.2.2. Nasal Aspirate/Wash (NA/W) Samples

A total of 593 NP swab specimens were tested for influenza A, influenza B and RSV by the Xpert Flu/RSV XC Assay and the reference assay. Of the 593 NP swab specimens, 190 were fresh, prospectively collected and 403 were frozen, archived specimens.

Overall, with NP swab specimens the Xpert Flu/RSV XC Assay demonstrated a PPA, NPA and OPA for detection of influenza A of 98.1%, 95.1%, and 95.6%, respectively, relative to the reference assay (Table 5). The Xpert Flu/RSV XC Assay PPA, NPA, and OPA for influenza B were 98.9%, 100%, and 99.8%, respectively (Table 5). The Xpert Flu/RSV XC Assay PPA, NPA, and OPA for RSV were 91.9%, 99.4%, and 98.7%, respectively (Table 5).

On fresh, prospectively collected NP swab specimens, the Xpert Flu/RSV XC Assay demonstrated a PPA, NPA, and OPA for detection of influenza A of 85.7%, 98.9%, and 98.4%, respectively, relative to the reference assay (Table 5). The Xpert Flu/RSV XC Assay PPA, NPA, and OPA for influenza B were 100%, 100%, and 100%, respectively (Table 5). The Xpert Flu/RSV XC Assay PPA, NPA, and OPA for RSV were 100%, 100%, and 100%, respectively (Table 5).

On frozen, archived NP swab specimens, the Xpert Flu/RSV XC Assay demonstrated a PPA, NPA, and OPA for detection of influenza A of 99.0%, 92.8%, and 94.3%, respectively, relative to the reference assay (Table 5). The Xpert Flu/RSV XC Assay PPA, NPA, and OPA for influenza B were 98.8%, 100%, and 99.8%, respectively (Table 5). The Xpert Flu/RSV XC Assay PPA, NPA, and OPA for RSV were 90.4%, 99.1%, and 98.0%, respectively (Table 5).

TABLE 5

Xpert Flu/RSV XC Assay Performance on NP Swab Specimens

| Specimen Type | Target | n | TP | FP | TN | FN | PPA % (95 CI) | NPA % (95 CI) | OPA % (95 CI) |
|---|---|---|---|---|---|---|---|---|---|
| Fresh | Flu A | 190 | 6 | 2[a] | 181 | 1[b] | 85.7 (42.1-99.6) | 98.9 (96.1-99.9) | 98.4 (95.5-99.7) |
| | Flu B | 190 | 3 | 0 | 187 | 0 | 100 (29.2-100) | 100 (98.0-100) | 100 (98.1-100) |
| | RSV | 190 | 10 | 0 | 180 | 0 | 100 (69.2-100) | 100 (98.0-100) | 100 (98.1-100) |
| Frozen | Flu A | 403 | 96 | 22[c] | 284 | 1[d] | 99.0 (94.4-100) | 92.8 (89.3-95.4) | 94.3 (91.6-96.3) |
| | Flu B | 403 | 85 | 0 | 317 | 1[e] | 98.8 (93.7-100) | 100 (98.8-100) | 99.8 (98.6-100) |
| | RSV | 403 | 47 | 3[f] | 348 | 5[g] | 90.4 (79.0-96.8) | 99.1 (97.5-99.8) | 98.0 (96.1-99.1) |
| All NP Swabs | Flu A | 593 | 102 | 24[h] | 465 | 2[i] | 98.1 (93.2-99.8) | 95.1 (92.8-96.8) | 95.6 (93.6-97.1) |
| | Flu B | 593 | 88 | 0 | 504 | 1[j] | 98.9 (93.9-100) | 100 (99.3-100) | 99.8 (99.1-100) |
| | RSV | 593 | 57 | 3[k] | 528 | 5[l] | 91.9 (82.2-97.3) | 99.4 (98.4-99.9) | 98.7 (97.4-99.4) |

[a]Testing results by sequencing: 2 of 2 were Flu A Positive.
[b]Testing results by sequencing: 1 of 1 was Flu A Negative.
[c]Testing results by sequencing: 17 of 22 were Flu A Positive; 5 of 22 were Flu A Negative.
[d]Testing results by sequencing: 1 of 1 was Flu A Negative.
[e]Testing results by sequencing: 1 of 1 was Flu B Negative.
[f]Testing results by sequencing: 2 of 3 were RSV Positive; 1 of 3 was RSV Negative.
[g]Testing results by sequencing: 1 of 5 was RSV Positive; 4 of 5 were RSV Negative.
[h]Testing results by sequencing: 19 of 24 were Flu A Positive; 5 of 24 were RSV Negative.
[i]Testing results by sequencing: 2 of 2 were Flu A Negative.
[j]Testing results by sequencing: 1 of 1 was Flu B Negative.
[k]Testing results by sequencing: 2 of 3 were RSV Positive; 1 of 3 was RSV Negative.
[l]Testing results by sequencing: 1 of 5 was RSV Positive; 4 of 5 were RSV Negative.

Of the Xpert Flu/RSV XC Assay runs performed with eligible specimens, 98.6% (1236/1254) of these specimens were successful on the first attempt. The remaining 18 gave indeterminate results on the first attempt (11 ERROR, 3 INVALID and 4 NO RESULT). Seventeen of the 18 specimens were retested, of which 14 yielded valid results after a single retest. There were four NA/W specimens with indeterminate results upon retest which were excluded in the analyses.

5.3. Example 3: Analytical Sensitivity (Limit of Detection)

Studies were performed to determine the analytical limit of detection (LoD) of the Xpert Flu/RSV XC Assay with two lots of reagents across three testing days. The maximum LoD observed per strain and per lot was selected for verification. Verification of the estimated LoD claim was performed on one reagent lot across a minimum of three testing days. LoD was established using two influenza A H3N2 strains, two influenza A 2009 H1N1 strains, two influenza B strains, two respiratory syncytial virus A (RSV A) strains and two respiratory syncytial virus B (RSV B) strains diluted into a negative pooled clinical matrix. The LoD is defined as the lowest concentration (tissue culture infective dose, TCID50/mL) per sample that can be reproducibly distinguished from negative samples with 95% confidence or the lowest concentration at which 19 of 20 replicates were positive. Each strain was tested in replicates of 20 per concentration of virus.

The LoD was determined empirically as the first concentration that had 19/20 or 20/20 positive results. The LoD point values for each strain tested are summarized in Table 6 to Table 11.

TABLE 6

Confirmed LoD (TCID$_{50}$/mL): Influenza A 2009 H1N1

| Strain ID—Influenza A subtype H1N1 | Confirmed LoD (TCID$_{50}$/mL) (at least 19/20 positive) |
| --- | --- |
| Influenza A/California/7/2009 | 0.3 (20/20) |
| Influenza A/Florida/27/2011 | 16 (19/20) |

TABLE 7

Confirmed LoD (TCID$_{50}$/mL): Influenza A H3N2

| Strain ID—Influenza A subtype H3N2 | Confirmed LOD (TCID$_{50}$/mL) (at least 19/20 positive) |
| --- | --- |
| Influenza A/Perth/16/2009 | 0.3 (20/20) |
| Influenza A/Victoria/361/2011 | 0.8 (20/20) |

TABLE 8

Confirmed LoD (TCID$_{50}$/mL): Influenza B

| Strain ID—Influenza A subtype 2009 H1N1 | Confirmed LoD (TCID$_{50}$/mL) (at least 19/20 positive) |
| --- | --- |
| Influenza B/Massachusetts/2/2012 | 0.5 (20/20) |
| Influenza B/Wisconsin/01/2010 | 0.6 (20/20) |

TABLE 9

Confirmed LoD (TCID50/mL): Respiratory Syncytial Virus A

| Strain ID—Influenza B | Confirmed LoD (TCID$_{50}$/mL) (at least 19/20 positive) |
| --- | --- |
| RSV A/2/Australia/61 | 1.2 (20/20) |
| RSV A/Long/MD/56 | 1.0 (19/20) |

TABLE 10

Confirmed LoD (TCID$_{50}$/mL): Respiratory Syncytial Virus B

| Strain ID—Influenza B | Confirmed LoD (TCID$_{50}$/mL) (at least 19/20 positive) |
| --- | --- |
| RSV B/Washington/18537/62 | 1.8 (20/20) |
| RSV B/9320/Massachusetts/77 | 2.0 (19/20) |

TABLE 11

Confirmed LoD (TCID$_{50}$/mL): Influenza A H7N9

| Strain ID | Confirmed LoD (TCID$_{50}$/mL) (at least 19/20 positive) |
| --- | --- |
| Influenza A/Anhui/1/2013 | 21.0 (19/20) |

Although this test has been shown to detect the novel avian influenza A(H7N9) cultured material, the performance characteristics of this device with clinical specimens that are positive for the novel avian influenza A(H7N9) virus have not been established. The Xpert Flu/RSV Assay can distinguish between influenza A and B viruses, but it cannot differentiate influenza subtypes.

5.4. Example 4: Analytical Specificity (Exclusivity)

The analytical specificity of the Xpert Flu/RSV XC Assay was evaluated by testing a panel of 44 cultures consisting of 16 viral, 26 bacterial, and two yeasts strains representing common respiratory pathogens or those potentially encountered in the nasopharynx. Three replicates of all bacterial and yeast strains were tested at concentrations of ≥10$^6$ CFU/mL. Three replicates of all viruses were tested at concentrations of ≥10$^5$ TCID50/mL. The analytical specificity was 100%. Results are shown in Table 12.

TABLE 12

Analytical Specificity of Xpert Flu/RSV XC Assay

| | | Result | | |
| --- | --- | --- | --- | --- |
| Organism | Concentration | Flu A | Flu B | RSV |
| No Template Control | N/A | NEG | NEG | NEG |
| Adenovirus Type 1 | 1.12 × 10$^7$ TCID$_{50}$/mL | NEG | NEG | NEG |
| Adenovirus Type 7 | 1.87 × 10$^5$ TCID$_{50}$/mL | NEG | NEG | NEG |
| Human coronavirus OC43 | 2.85 × 10$^5$ TCID$_{50}$/mL | NEG | NEG | NEG |
| Human coronavirus 229E | 1 × 10$^5$ TCID$_{50}$/mL | NEG | NEG | NEG |
| Cytomegalovirus | 7.24 × 10$^5$ TCID$_{50}$/mL | NEG | NEG | NEG |
| Echovirus | 3.31 × 10$^7$ TCID$_{50}$/mL | NEG | NEG | NEG |
| Enterovirus | 1 × 10$^5$ TCID$_{50}$/mL | NEG | NEG | NEG |
| Epstein Barr Virus | 7.16 × 10$^7$ TCID$_{50}$/mL | NEG | NEG | NEG |
| HSV | 8.9 × 10$^6$ TCID$_{50}$/mL | NEG | NEG | NEG |
| Measles | 6.3 × 10$^5$ TCID$_{50}$/mL | NEG | NEG | NEG |
| Human metapneumovirus | 3.8 × 10$^5$ TCID$_{50}$/mL | NEG | NEG | NEG |
| Mumps virus | 6.31 × 10$^6$ TCID$_{50}$/mL | NEG | NEG | NEG |
| Human parainfluenza Type 1 | 1.15 × 10$^6$ TCID$_{50}$/mL | NEG | NEG | NEG |
| Human parainfluenza Type 2 | 1 × 10$^5$ TCID$_{50}$/mL | NEG | NEG | NEG |
| Human parainfluenza Type 3 | 3.55 × 10$^7$ TCID$_{50}$/mL | NEG | NEG | NEG |
| Rhinovirus Type 1A | 1.26 × 10$^5$ TCID$_{50}$/mL | NEG | NEG | NEG |
| *Acinetobacter baumannii* | >1 × 10$^6$ CFU/mL[a] | NEG[a] | NEG | NEG |
| *Burkholderia cepacia* | >1 × 10$^6$ CFU/mL | NEG | NEG | NEG |
| *Candida albicans* | >1 × 10$^6$ CFU/mL | NEG | NEG | NEG |
| *Candida parapsilosis* | >1 × 10$^6$ CFU/mL | NEG | NEG | NEG |
| *Bordetella pertussis* | 1 × 10$^8$ CFU/mL | NEG | NEG | NEG |
| *Chlamydia pneumoniae* | 3.16 × 10$^5$ CFU/mL | NEG | NEG | NEG |
| *Citrobacter freundii* | >1 × 10$^6$ CFU/mL | NEG | NEG | NEG |

TABLE 12-continued

Analytical Specificity of Xpert Flu/RSV XC Assay

| Organism | Concentration | Flu A | Flu B | RSV |
|---|---|---|---|---|
| Corynebacterium sp. | >1 × 10$^6$ CFU/mL | NEG | NEG | NEG |
| Escherichia coli | >1 × 10$^6$ CFU/mL | NEG | NEG | NEG |
| Enterococcus faecalis | >1 × 10$^6$ CFU/mL | NEG | NEG | NEG |
| Hemophilus influenzae | 1 × 10$^6$ CFU/mL | NEG | NEG | NEG |
| Lactobacillus sp. | 1 × 10$^6$ CFU/mL | NEG | NEG | NEG |
| Legionella spp. | 1 × 10$^8$ CFU/mL | NEG | NEG | NEG |
| Moraxella catarrhalis | >1 × 10$^6$ CFU/mL | NEG | NEG | NEG |
| Mycobacterium tuberculosis (avirulent) | 1.15 × 10$^6$ CFU/mL | NEG | NEG | NEG |
| Mycoplasma pneumoniae | 1 × 10$^7$ CFU/mL | NEG | NEG | NEG |
| Neisseria meningitidis | >1 × 10$^6$ CFU/mL | NEG | NEG | NEG |
| Neisseria mucosa | >1 × 10$^6$ CFU/mL | NEG | NEG | NEG |
| Propionibacterium acnes | >1 × 10$^6$ CFU/mL | NEG | NEG | NEG |
| Pseudomonas aeruginosa | >1 × 10$^6$ CFU/mL | NEG | NEG | NEG |
| Staphylococcus aureus (protein A producer) | >1 × 10$^6$ CFU/mL | NEG | NEG | NEG |
| Staphylococcus epidermidis | >1 × 10$^6$ CFU/mL | NEG | NEG | NEG |
| Staphylococcus haemolyticus | >1 × 10$^6$ CFU/mL | NEG | NEG | NEG |
| Streptococcus agalactiae | >1 × 10$^6$ CFU/mL | NEG | NEG | NEG |
| Streptococcus pneumoniae | >1 × 10$^6$ CFU/mL | NEG | NEG | NEG |
| Streptococcus pyogenes | >1 × 10$^6$ CFU/mL | NEG | NEG | NEG |
| Streptococcus salivarius | >1 × 10$^6$ CFU/mL | NEG | NEG | NEG |
| Streptococcus sanguinis | >1 × 10$^6$ CFU/mL | NEG | NEG | NEG |

[a]For Acinetobacter baumannii upon initial testing 1/3 replicates was positive for Flu A with a Ct of 39.2 (cut-off = 40). An additional 23 replicates were tested at >1 × 10$^6$ CFU/mL; 23/23 replicates were correctly reported as Flu A NEGATIVE; Flu B NEGATIVE; RSV NEGATIVE.

5.5. Example 5: Analytical Reactivity (Inclusivity)

The analytical reactivity of the Xpert Flu/RSV XC Assay was evaluated against multiple strains of influenza A H1N1 (seasonal pre-2009), influenza A H1N1 (pandemic 2009), influenza A H3N2 (seasonal), avian influenza A (H5N1, H5N2, H6N2, H7N2, H7N3, H2N2, and H7N9), and H9N2), influenza B (representing strains from both Victoria and Yamagata lineages), and respiratory syncytial virus A/B (RSV A and RSV B) at levels near the analytical LoD. A total of 64 strains comprising of 54 influenza viruses and 10 RSV viruses were tested in this study with the Xpert Flu/RSV XC Assay.

Three replicates were tested for each strain. Results are shown in Table 13.

TABLE 13

Analytical Reactivity (Inclusivity) of Xpert Flu/RSV XC Assay

| Virus | Strain | Concentration | Flu A | Flu B | RSV |
|---|---|---|---|---|---|
| No Template Control | | N/A | NEG | NEG | NEG |
| Influenza A H1N1 (pre-2009) | A/swine/Iowa/15/30 | 32.0 TCID$_{50}$/mL | POS | NEG | NEG |
| | A/WS/33 | 32.0 TCID$_{50}$/mL | POS | NEG | NEG |
| | A/PR/8/34 | 32.0 TCID$_{50}$/mL | POS | NEG | NEG |
| | A/Mal/302/54 | 32.0 TCID$_{50}$/mL | POS | NEG | NEG |
| | A/Denver/1/57 | 32.0 TCID$_{50}$/mL | POS | NEG | NEG |
| | A/New Jersey/8/76 | 32.0 TCID$_{50}$/mL | POS | NEG | NEG |
| | A/New Caledonia/20/1999 | 32.0 TCID$_{50}$/mL | POS | NEG | NEG |
| | A/New York/55/2004 | 32.0 TCID$_{50}$/mL | POS | NEG | NEG |
| | A/Solomon Island/3/2006 | 32.0 TCID$_{50}$/mL | POS | NEG | NEG |
| | A/Taiwan/42/06 | 32.0 TCID$_{50}$/mL | POS | NEG | NEG |
| | A/Brisbane/59/2007 | 32.0 TCID$_{50}$/mL | POS | NEG | NEG |
| Influenza A H1N1 (pdm2009) | A/California/7/2009 | 32.0 TCID$_{50}$/mL | POS | NEG | NEG |
| | A/swine/NY/02/2009 | 32.0 TCID$_{50}$/mL | POS | NEG | NEG |
| | A/Florida/27/2011 | 32.0 TCID$_{50}$/mL | POS | NEG | NEG |
| | A/Colorado/14/2012 | 32.0 TCID$_{50}$/mL | POS | NEG | NEG |
| | A/Washington/24/2012 | 80.0[a] TCID$_{50}$/mL | POS | NEG | NEG |
| Influenza A H3N2 (Seasonal) | A/Aichi/2/68 | 1.6 TCID$_{50}$/mL | POS | NEG | NEG |
| | A/Hong Kong/8/68 | 1.6 TCID$_{50}$/mL | POS | NEG | NEG |
| | A/Port Chalmers/1/73 | 1.6 TCID$_{50}$/mL | POS | NEG | NEG |
| | A/Hawaii/15/2001 | 1.6 TCID$_{50}$/mL | POS | NEG | NEG |
| | A/Wisconsin/67/05 | 1.6 TCID$_{50}$/mL | POS | NEG | NEG |
| | A/Brisbane/10/2007 | 1.6 TCID$_{50}$/mL | POS | NEG | NEG |
| | A/Perth/16/2009 | 1.6 TCID$_{50}$/mL | POS | NEG | NEG |
| | A/Minnesota/11/2010 (H3N2)v | 1.6 TCID$_{50}$/mL | POS | NEG | NEG |
| | A/Indiana/08/2011 (H3N2)v | 1.6 TCID$_{50}$/mL | POS | NEG | NEG |
| | A/Victoria/361/2011 | 1.6 TCID$_{50}$/mL | POS | NEG | NEG |
| | A/Texas/50/2012 | 1.6 TCID$_{50}$/mL | POS | NEG | NEG |
| Avian influenza A | A/duck/Hunan/795/2002 (H5N1) | ≤1 pg/μL[b] | POS | NEG | NEG |
| | A/chicken/Hubei/327/2004 (H5N1) | ≤1 pg/μL[b] | POS | NEG | NEG |
| | A/Anhui/01/2005 (H5N1) | ≤1 pg/μL[b] | POS | NEG | NEG |
| | A/Japanese white eye/Hong Kong/1038/2006 (H5N1) | ≤1 pg/μL[b] | POS | NEG | NEG |
| | A/mallard/WI/34/75 (H5N2) | ≤1 pg/μL[b] | POS | NEG | NEG |
| | A/chicken/CA431/00 (H6N2) | ≤1 pg/μL[b] | POS | NEG | NEG |
| | A/duck/LTC-10-82743/1943 (H7N2) | ≤1 pg/μL[b] | POS | NEG | NEG |
| | A/chicken/NJ/15086-3/94 (H7N3) | ≤1 pg/μL[b] | POS | NEG | NEG |
| | A/Anhui/1/2013 (H7N9) | N/A[c] | POS | NEG | NEG |
| | A/Shanghai/1/2013 (H7N9) | N/A[c] | POS | NEG | NEG |
| | A/chicken/Korea/38349-p96323/1996 (H9N2) | ≤1 pg/μL[b] | POS | NEG | NEG |
| | A/Mallard/NY/6750/78 (H2N2) | ≤1 pg/μL[b] | POS | NEG | NEG |

TABLE 13-continued

Analytical Reactivity (Inclusivity) of Xpert Flu/RSV XC Assay

| Virus | Strain | Concentration | Result Flu A | Flu B | RSV |
|---|---|---|---|---|---|
| Influenza B | B/Lee/40 | 1.2 TCID$_{50}$/mL | NEG | POS | NEG |
| | B/Allen/45 | 1.2 TCID$_{50}$/mL | NEG | POS | NEG |
| | B/GL/1739/54 | 1.2 TCID$_{50}$/mL | NEG | POS | NEG |
| | B/Maryland/1/59 | 1.2 TCID$_{50}$/mL | NEG | POS | NEG |
| | B/Panama/45/90[d] | 3.0 TCID$_{50}$/mL[e] | NEG | POS | NEG |
| | B/Florida/07/2004[f] | 1.2 TCID$_{50}$/mL | NEG | POS | NEG |
| | B/Florida/02/06[d] | 1.2 TCID$_{50}$/mL | NEG | POS | NEG |
| | B/Florida/04/06[f] | 1.2 TCID$_{50}$/mL | NEG | POS | NEG |
| | B/Wisconsin/01/2011[d] | 1.2 TCID$_{50}$/mL | NEG | POS | NEG |
| | B/Massachusetts/2/2012[f] | 1.2 TCID$_{50}$/mL | NEG | POS | NEG |
| | B/Hong Kong/5/72 | 1.2 TCID$_{50}$/mL | NEG | POS | NEG |
| | B/Wisconsin/01/2010[f] | 1.2 TCID$_{50}$/mL | NEG | POS | NEG |
| | B/Malaysia/2506/04[d] | 1.2 TCID$_{50}$/mL | NEG | POS | NEG |
| | B/Taiwan/2/62 | 1.2 TCID$_{50}$/mL | NEG | POS | NEG |
| | B/Brisbane/60/2008[d] | 1.2 TCID$_{50}$/mL | NEG | POS | NEG |
| RSV A | RSV-A/Long/MD/56 | 2.4 TCID$_{50}$/mL | NEG | NEG | POS |
| | RSV-A/2/Australia/61 | 2.4 TCID$_{50}$/mL | NEG | NEG | POS |
| | RSV-A/NY (Clinical unknown) | 2.4 TCID$_{50}$/mL | NEG | NEG | POS |
| | RSV-A/W1/629-8-2/2007 | 2.4 TCID$_{50}$/mL | NEG | NEG | POS |
| | RSV-A/W1/629-11-1/2008 | 2.4 TCID$_{50}$/mL | NEG | NEG | POS |
| RSV B | RSV-B/Wash/18537/62 | 4.0 TCID$_{50}$/mL | NEG | NEG | POS |
| | RSV-B/9320/MA/77 | 4.0 TCID$_{50}$/mL | NEG | NEG | POS |
| | RSV-B/WV14617/85 | 4.0 TCID$_{50}$/mL | NEG | NEG | POS |
| | RSV-B/CH93(18)-18 | 20.0 TCID$_{50}$/mL[g] | NEG | NEG | POS |
| | RSV-B/WI/629-5B/0607 | 4.0 TCID$_{50}$/mL | NEG | NEG | POS |

[a]Influenza A/Washington/24/2012 was tested at 5 × LoD (80.0 TCID$_{50}$/mL) to obtain 3/3 replicates with Flu A POSITIVE result calls.
[b]Purified viral RNA in simulated background matrix was used for avian influenza A viruses due to biosafety regulations.
[c]Inactivated avian influenza A (H7N9) viruses without viral titer was diluted 100.000 fold in simulated background matrix and tested due to biosafety regulations.
[d]Known Victoria lineage
[e]Influenza B/Panama/45/90 was tested at 5 × LoD (3.0 TCID$_{50}$/mL) to obtain 3/3 replicates with Flu B POSITIVE result calls.
[f]Known Yamagata lineage.
[g]RSV-B/CH93(18)-18 was tested at 10 × LoD (20.0 TCID$_{50}$/mL) to obtain 3/3 replicates with RSV POSITIVE result calls.

5.6. Example 6: Interfering Substances

In a non-clinical study, potentially interfering substances that may be present in the nasopharynx were evaluated directly relative to the performance of the Xpert Flu/RSV XC Assay. Potentially interfering substances in the nasopharynx may include, but are not limited to: blood, nasal secretions or mucus, and nasal and throat medications used to relieve congestion, nasal dryness, irritation, or asthma and allergy symptoms, as well as antibiotics and antivirals. Negative samples (n=8) were tested per each substance to determine the effect on the performance of the sample processing control (SPC). Positive samples (n=8) were tested per substance with six influenza (four influenza A and two influenza B) and four RSV (two RSV A and two RSV B) strains spiked at 2× the analytical LoD determined for each strain. All results were compared to positive and negative Universal Transport Medium (UTM) controls.

These evaluated substances are listed in Table 14 with active ingredients and concentrations tested shown. There was no assay interference in the presence of the substances at the concentrations tested in this study. All positive and negative replicates were correctly identified using the Xpert Flu/RSV XC Assay. FluMist vaccine samples were correctly reported as Flu A POSITIVE; FLU POSITIVE; RSV NEGATIVE as expected. Samples containing FluMist may cause false positive results.

TABLE 14

Potentially Interfering Substances in Xpert Flu/RSV XC Assay

| Substance ID | Substance/ Class | Substance/ Active Ingredient | Source | Concentration Tested |
|---|---|---|---|---|
| C | Control | UTM | Copan | 100% (v/v) |
| Albuterol Sulfate | Beta-adrenergic bronchodilator | Albuterol Sulfate | Custom Care Pharmacy, San Ramon | 0.83 mg/mL (equivalent to 1 dose per day) |
| Blood | Blood | Blood (Human) | Stanford University | 2% (v/v) |
| BD | Transport Media | n/a | BD diagnostics | 100% (v/v) |
| M4 | Transport Media | n/a | Remel | 100% (v/v) |
| M4RT | Transport Media | n/a | Remel | 100% (v/v) |
| M5 | Transport Media | n/a | Remel | 100% (v/v) |
| Menthol | Throat lozenges, oral anesthetic and analgesic | Benzocaine, Menthol | Walgreens | 1.7 mg/mL |

TABLE 14-continued

Potentially Interfering Substances in Xpert Flu/RSV XC Assay

| Substance ID | Substance/Class | Substance/Active Ingredient | Source | Concentration Tested |
|---|---|---|---|---|
| Mucin | Mucin | Purified Mucin protein (Bovine or porcine submaxillary gland) | Sigma | 2.5% (w/v) |
| Mupirocin | Antibiotic, nasal ointment | Mupirocin | Custom Care Pharmacy, San Ramon | 10 mg/mL |
| Saline | Saline Nasal Spray | Sodium Chloride (0.65%) | Walgreens | 15% (v/v) |
| Anefrin | Nasal Spray | Oxymetazolin, 0.05% | Walgreens | 15% (v/v) |
| PHNY | Nasal Drops | Phenylephrine, 0.5% | Walgreens | 15% (v/v) |
| Tamiflu | Anti-viral drugs | Zanamivir | Custom Care Pharmacy, San Ramon | 7.5 mg/mL |
| Tobramycin | Antibacterial systemic | Tobramycin | Custom Care Pharmacy, San Ramon | 4 µg/mL |
| Zicam | Nasal Gel | Luffa opperculata, Galphimia glauca, Histaminum hydrochloricum Sulfur | Walgreens | 15% (w/v) |
| Flu Mist | FluMist® | Live intranasal influenza virus vaccine | Custom Care Pharmacy, San Ramon | 6.7% (v/v) |
| Fluticasone Propionate Nasal Spray | Nasal corticosteroid | Fluticasone Propionate | Custom Care Pharmacy, San Ramon | 5 µg/mL |

5.7. Example 7: Carry-Over Contamination Study

A study was conducted to demonstrate that single-use, self-contained GeneXpert cartridges prevent carry-over contamination in negative samples run following very high positive samples in the same GeneXpert module. The study consisted of a negative sample processed in the same GeneXpert module immediately following a very high influenza A sample (approximately $10^6$ TCID50/test). This testing scheme was repeated 20 times on four GeneXpert modules for a total of 41 runs resulting in 20 positive and 21 negative specimens. All 20 positive samples were correctly reported as Flu A POSITIVE; Flu B NEGATIVE; RSV NEGATIVE. All 21 negative samples were correctly reported as Flu A NEGATIVE; Flu B NEGATIVE; RSV NEGATIVE.

5.8. Example 8: Fresh Versus Frozen Sample Equivalency Study

Fresh and frozen ($\geq-70°$ C.) specimen equivalency in the Xpert Flu/RSV XC Assay was evaluated by testing individual influenza and RSV strains at three different concentrations representing low positives (2×LoD), moderate positives (5×LoD), and high positives (10×LoD) in simulated background matrix. Negative samples consisted of simulated background matrix only. Fresh and frozen specimen equivalency was determined using one seasonal Flu A H3N2 strain (A/Victoria/361/2011), one Flu B strain (B/Wisconsin/01/11), one RSV A strain (RSV A/Long/MD/56), and one RSV B strain (RSV B/9320/MA/77). Replicates of 20 were tested for each specimen type and concentration. All positive and negative specimens were tested fresh, after one freeze-thaw cycle, and after two freeze-thaw cycles.

There were no differences in the performance of the Xpert Flu/RSV Assay between fresh virus dilutions and two sequential freeze thaw cycles for positive and negative samples. All positive and negative replicates were correctly identified using the Xpert Flu/RSV XC Assay.

5.9. Example 9: Reproducibility

A panel of 10 specimens with varying concentrations of influenza A, influenza B, and RSV was tested on ten different days by two different operators, at each of three sites (10 specimens×1 time/day×10 days×2 operators×3 sites). One lot of Xpert Flu/RSV XC Assay cartridges was used at each of the 3 testing sites. The Xpert Flu/RSV XC Assay was performed according to the Xpert Flu/RSV XC Assay procedure. Results are summarized in Table 15.

The reproducibility of the Xpert Flu/RSV XC Assay was also evaluated in terms of the fluorescence signal expressed in Ct values for each target detected. The mean, standard deviation (SD), and coefficient of variation (CV) between-sites, between-days, between-operators, and within-assay for each panel member are presented in Table 16.

TABLE 15

Summary of Reproducibility Results

| | Site 1/GX Dx | | | Site 2/Infinity-80 | | | Site 3/Infinity-48 | | | % Total Agreement |
|---|---|---|---|---|---|---|---|---|---|---|
| Sample ID | Op 1 | Op 2 | Site | Op 1 | Op 2 | Site | Op 1 | Op 2 | Site | by Sample |
| Negative | 100% (10/10) | 100% (10/10) | 100% (20/20) | 100% (10/10) | 100% (10/10) | 100% (20/20) | 100% (10/10) | 100% (10/10) | 100% (20/20) | 100% (60/60) |
| Flu A - High Neg | 70.0% (7/10) | 60.0% (6/10) | 65.0% (13/20) | 80.0% (8/10) | 80.0% (8/10) | 80.0% (16/20) | 60.0% (6/10) | 70.0% (7/10) | 65.0% (13/20) | 70.0% (42/60) |
| Flu A - Low Pos | 100% (10/10) | 90.0% (9/10) | 95.0% (19/20) | 100% (10/10) | 100% (10/10) | 100% (20/20) | 100% (10/10) | 90.0% (9/10) | 95.0% (19/20) | 96.7% (58/60) |
| Flu A - Mod Pos | 100% (10/10) | 90.0% (9/10) | 95.0% (19/20) | 100% (10/10) | 100% (10/10) | 100% (20/20) | 100% (10/10) | 100% (10/10) | 100% (20/20) | 98.3% (59/60) |
| Flu B - High Neg | 90.0% (9/10) | 70.0% (7/10) | 80.0% (16/20) | 100% (10/10) | 70.0% (7/10) | 85.0% (17/20) | 50.0% (5/10) | 80.0% (8/10) | 65.0% (13/20) | 76.7% (46/60) |

TABLE 15-continued

Summary of Reproducibility Results

| | Site 1/GX Dx | | | Site 2/Infinity-80 | | | Site 3/Infinity-48 | | | % Total Agreement |
|---|---|---|---|---|---|---|---|---|---|---|
| Sample ID | Op 1 | Op 2 | Site | Op 1 | Op 2 | Site | Op 1 | Op 2 | Site | by Sample |
| Flu B - Low Pos | 100% (10/10) | 90.0% (9/10) | 95.0% (19/20) | 90.0% (9/10) | 70.0% (7/10) | 80.0% (16/20) | 100% (10/10) | 90.0% (9/10) | 95.0% (19/20) | 90.0% (54/60) |
| Flu B - Mod Pos | 100% (10/10) | 100% (10/10) | 100% (20/20) | 100% (10/10) | 100% (10/10) | 100% (20/20) | 100% (10/10) | 100% (10/10) | 100% (20/20) | 100% (60/60) |
| RSV - High Neg | 60.0% (6/10) | 50.0% (5/10) | 55.0% (11/20) | 90.0% (9/10) | 60.0% (6/10) | 75.0% (15/20) | 70.0% (7/10) | 70.0% (7/10) | 70.0% (14/20) | 66.7% (40/60) |
| RSV - Low Pos | 77.8%[a] (7/9) | 100% (10/10) | 89.5% (17/19) | 80.0% (8/10) | 80.0% (8/10) | 80.0% (16/20) | 90.0% (9/10) | 90.0% (9/10) | 90.0% (18/20) | 86.4% (51/59) |
| RSV - Mod Pos | 100%[b] (9/9) | 100% (10/10) | 100% (19/19) | 100% (10/10) | 100% (10/10) | 100% (20/20) | 100% (10/10) | 100% (10/10) | 100% (20/20) | 100% (59/59) |

[a]One sample indeterminate on initial testing; retest not done.
[b]One sample 2x indeterminate.

TABLE 16

Summary of Reproducibility Data

| Sample | Assay Channel (Analyte) | N[a] | Mean Ct | Between-Site | | Between-Day | | Between-Operator + Within Assay | | Total | |
|---|---|---|---|---|---|---|---|---|---|---|---|
| | | | | SD | CV (%) | SD | CV (%) | SD | CV (%) | SD | CV (%) |
| Negative | SPC | 60 | 30.8 | 0.06 | 0.2 | 0 | 0 | 0.29 | 0.9 | 0.29 | 0.9 |
| Flu A - High Neg | FluA1 | 18 | 38.0 | 0 | 0 | 1.55 | 4.1 | 0.85 | 2.2 | 1.77 | 4.6 |
| | FluA2 | 0 | NA | NA | NA | NA | NA | NA | NA | NA | NA |
| | FluA3 | 0 | NA | NA | NA | NA | NA | NA | NA | NA | NA |
| Flu A - Low Pos | FluA1 | 58 | 34.9 | 0.38 | 1.1 | 0.10 | 0.3 | 1.28 | 3.7 | 1.34 | 3.8 |
| | FluA2 | 0 | NA | NA | NA | NA | NA | NA | NA | NA | NA |
| | FluA3 | 0 | NA | NA | NA | NA | NA | NA | NA | NA | NA |
| Flu A - Mod Pos | FluA1 | 59 | 33.5 | 0.49 | 1.5 | 0 | 0 | 1.29 | 3.9 | 1.38 | 4.1 |
| | FluA2 | 10 | 36.3 | NA | NA | NA | NA | NA | NA | NA | NA |
| | FluA3 | 0 | NA | NA | NA | NA | NA | NA | NA | NA | NA |
| Flu B - High Neg | FluB | 14 | 36.6 | 0.80 | 1.4 | 0 | 0 | 2.83 | 7.7 | 2.94 | 8.0 |
| Flu B - Low Pos | FluB | 54 | 33.4 | 0 | 0 | 1.07 | 3.2 | 1.76 | 5.3 | 2.06 | 6.2 |
| Flu B - Mod Pos | FluB | 60 | 32.1 | 0 | 0 | 0.38 | 1.2 | 1.47 | 4.6 | 1.51 | 4.7 |
| RSV - High Neg | RSV | 20 | 37.4 | 0 | 0 | 0.14 | 0.4 | 1.68 | 4.5 | 1.68 | 4.5 |
| RSV - Low Pos | RSV | 51 | 36.2 | 0.22 | 0.6 | 0 | 0 | 1.75 | 4.8 | 1.76 | 4.9 |
| RSV - Mod Pos | RSV | 60 | 35.1 | 0 | 0 | 0.24 | 0.9 | 1.20 | 3.4 | 1.24 | 3.5 |

[a]Results with non-zero Ct values out of 60.

5.10. Example 10: Expected Assay Coverage

To determine the expected influenza strain coverage using Xpert Flu/RSV assay, influenza isolates from Jan. 1, 2009, through May 21, 2014, were analyzed by sequence to identify mismatches with the primer and probe sequences in Table A. Strains with mismatches to any one of the primers and probes were assumed to impact the sensitivity of the assay, although there is a higher chance of being detected because of the increased redundancy with multiple primer and probes sequences for each influenza type. The impact of the mismatches on the sensitivity of the assay is dependent on the identity and position of the mismatch. Table 17 shows the results of the analysis.

TABLE 17

Expected Assay Coverage for Flu A

| Influenza virus | Gene Segment | Flu/RSV Primer & Probe | Total isolates | Survey period | # mismatch | # perfect match | % absolute Coverage | Estimated Overall Coverage | % Expected Assay coverage |
|---|---|---|---|---|---|---|---|---|---|
| Flu A H1N1pdm09 | MP | Fwd | 3570 | Jan. 1, 2009-May 21, 2014 | 63 | 3507 | 98.2% | 98.2% | 100.0% |
| | | Rev | 3570 | Jan. 1, 2009-May 21, 2014 | 25 | 3545 | 99.3% | | |
| | | Probe | 3570 | Jan. 1, 2009-May 21, 2014 | 13 | 3557 | 99.6% | | |
| | PA | Fwd | 3570 | Jan. 1, 2009-May 21, 2014 | 91 | 3479 | 97.5% | 96.1% | |
| | | Rev | 3570 | Jan. 1, 2009-May 21, 2014 | 138 | 3432 | 96.1% | | |
| | | Probe | 3570 | Jan. 1, 2009-May 21, 2014 | 31 | 3539 | 99.1% | | |
| | PB2 | Fwd | 3570 | Jan. 1, 2009-May 21, 2014 | 85 | 3485 | 97.6% | 97.6% | |
| | | Rev | 3570 | Jan. 1, 2009-May 21, 2014 | 30 | 3540 | 99.2% | | |
| | | Probe | 3570 | Jan. 1, 2009-May 21, 2014 | 10 | 3560 | 99.7% | | |

TABLE 17-continued

Expected Assay Coverage for Flu A

| Influenza virus | Gene Segment | Flu/RSV Primer & Probe | Total isolates | Survey period | # mismatch | # perfect match | % absolute Coverage | Estimated Overall Coverage | % Expected Assay coverage |
|---|---|---|---|---|---|---|---|---|---|
| Flu A H1N1 seasonal | MP | Fwd | 85 | Jan. 1, 2009-May 21, 2014 | 0 | 85 | 100.0% | 98.8% | 100.0% |
| | | Rev | 85 | Jan. 1, 2009-May 21, 2014 | 1 | 84 | 98.8% | | |
| | | Probe | 85 | Jan. 1, 2009-May 21, 2014 | 0 | 85 | 100.0% | | |
| | PA | Fwd | 85 | Jan. 1, 2009-May 21, 2014 | 5 | 80 | 94.1% | 94.1% | |
| | | Rev | 85 | Jan. 1, 2009-May 21, 2014 | 1 | 84 | 98.8% | | |
| | | Probe | 85 | Jan. 1, 2009-May 21, 2014 | 0 | 85 | 100.0% | | |
| | PB2 | Fwd | 85 | Jan. 1, 2009-May 21, 2014 | 1 | 84 | 98.8% | 98.8% | |
| | | Rev | 85 | Jan. 1, 2009-May 21, 2014 | 0 | 85 | 100.0% | | |
| | | Probe | 85 | Jan. 1, 2009-May 21, 2014 | 1 | 84 | 98.8% | | |
| Flu A H3N2 | MP | Fwd | 1671 | Jan. 1, 2009-May 21, 2014 | 6 | 1665 | 99.6% | 99.4% | 100.0% |
| | | Rev | 1671 | Jan. 1, 2009-May 21, 2014 | 2 | 1669 | 99.9% | | |
| | | Probe | 1671 | Jan. 1, 2009-May 21, 2014 | 10 | 1661 | 99.4% | | |
| | PA | Fwd | 1671 | Jan. 1, 2009-May 21, 2014 | 31 | 1640 | 98.1% | 96.9% | |
| | | Rev | 1671 | Jan. 1, 2009-May 21, 2014 | 52 | 1619 | 96.9% | | |
| | | Probe | 1671 | Jan. 1, 2009-May 21, 2014 | 17 | 1654 | 99.0% | | |
| | PB2 | Fwd | 1671 | Jan. 1, 2009-May 21, 2014 | 208 | 1463 | 87.6% | 87.6% | |
| | | Rev | 1671 | Jan. 1, 2009-May 21, 2014 | 12 | 1659 | 99.3% | | |
| | | Probe | 1671 | Jan. 1, 2009-May 21, 2014 | 2 | 1669 | 99.9% | | |
| Flu B | MP | Fwd | 683 | Jan. 1, 2009-May 20, 2014 | 30 | 653 | 95.6% | 95.6% | 98.5% |
| | | Rev | 683 | Jan. 1, 2009-May 20, 2014 | 30 | 653 | 95.6% | | |
| | | Probe | 683 | Jan. 1, 2009-May 20, 2014 | 26 | 657 | 96.2% | | |
| | NS | Fwd | 683 | Jan. 1, 2009-May 20, 2014 | 10 | 673 | 98.5% | 98.5% | |
| | | Rev | 683 | Jan. 1, 2009-May 20, 2014 | 3 | 680 | 99.6% | | |
| | | Probe | 683 | Jan. 1, 2009-May 20, 2014 | 10 | 673 | 98.5% | | |
| Avian Flu | H5-MP | Fwd | 78 | Jan. 1, 2009-May 20, 2014 | 0 | 78 | 100.0% | 96.2% | 96.2% |
| | | Rev | 78 | Jan. 1, 2009-May 20, 2014 | 3 | 75 | 96.2% | | |
| | | Probe | 78 | Jan. 1, 2009-May 20, 2014 | 1 | 77 | 98.7% | | |
| | H7-MP | Fwd | 107 | til May 20, 2014 | 0 | 107 | 100.0% | 100.0% | 100.0% |
| | | Rev | 107 | til May 20, 2014 | 0 | 107 | 100.0% | | |
| | | Probe | 107 | til May 20, 2014 | 0 | 107 | 100.0% | | |

The data As shown in Table 17, detecting only MP results in a failure to detect 1.8% of Flu A H1N1pdm09 isolates, 1.2% of Flu A H1N1seasonal isolates, and 0.6% of Flu A H3N2 isolates. Addition of PA and PB2 to the assay results in detection of 100% of the Flu A isolates analyzed, suggesting that the Flu isolates with mismatches relative to the MP primer and probe sequences do not have mismatches in at least one of the PA or PB2 primer and probe sequences. In addition, the Xpert Flu/RSV assay detects 98.5% of Flu B isolates, 96.2% of Avian Flu H5 isolates, and 100% of Avian Flu H7 isolates (or 98.4% of Avian Flu H5 +H7 isolates).

The data are summarized in Table 18 below:

TABLE 18

Summary of Expected Assay Coverage

| Virus | Flu/RSV Primer/ Probe | Mis-match | Perfect match | Total | % coverage | Assay coverage |
|---|---|---|---|---|---|---|
| Influenza A (H1N1) | MP | 64 | 3591 | 3655 | 98.2% | 100% |
| | PA | 143 | 3512 | 3655 | 96.1% | |
| | PB2 | 86 | 3569 | 3655 | 97.6% | |

TABLE 18-continued

Summary of Expected Assay Coverage

| Virus | Flu/RSV Primer/ Probe | Mis-match | Perfect match | Total | % coverage | Assay coverage |
|---|---|---|---|---|---|---|
| Influenza A (H3N2) | MP | 10 | 1661 | 1671 | 99.4% | 100% |
| | PA | 52 | 1619 | 1671 | 96.9% | |
| | PB2 | 208 | 1463 | 1671 | 87.6% | |
| Avian H5 + H7 | MP | 3 | 182 | 185 | 98.4% | 98.4% |
| Influenza B | MP | 26 | 657 | 683 | 96.2% | 98.5% |
| | NS | 10 | 673 | 683 | 98.5% | |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that changes can be made without departing from the spirit and scope of the invention(s).

| TABLE OF CERTAIN SEQUENCES | | |
|---|---|---|
| SEQ ID NO | Description | Sequence |
| 1 | Flu A 1 polymerase basic 2 (PB2) gene (KC471406.1 for | ATGGAGAGAATAAAAGAACTAAGAGATCTAATGTCGCAGTCTCGCACTCGCGAGATACT CACTAAGACCACTGTGGACCATATGGCCATAATCAAAAAGTACACGTCAGGAAGGCAGG AGAAGAACCCCGCACTCAGAATGAAATGGATGATGGCAATGAAATACCCAATTACAGCA GACAGGAGAATAATGGACATGATTCCAGAGAGGAATGAACAAGGACAAACCCTCTGGAG |

-continued

TABLE OF CERTAIN SEQUENCES

| SEQ ID NO | Description | Sequence |
|---|---|---|
| | Influenza A virus A/Swine/Korea/ CY02-09/2012 (H3N2) segment 1) | CAAAACAACCGATGCTGGATCGGACCGTGTGATGGTATCACCCCTGGCCGTAACATGGT GGAATAGGAATGGCCCAACAACAAGCACAGTTCACTACCCTAAGGTATACAAAACTTAT TTCGAAAAAGTCGAAAGGTTAAAACATGGTACCTTTGGCCCTGTCCACTTCAGAAATCA AGTTAAAATAAGAAGGAGGGTTGACACAAACCCCGGTCATGCAGATCTCAGTGCCAAGG AGGCACAGGATGTGATCATGGAAGTTGTTTTCCCAAACGAAGTGGGGGCAAGAATACTG ACATCAGAGTCACAGCTGACAATAACAAAAGAAAAGAAAGAAGAGCTCCAGGATTGTAA AATTGCTCCCTTGATGGTGGCATACATGCTAGAAAGAGAATTGGTTCGTAAGACGAGGT TTCTTCCGGTGGCTGGTGGAACAAGCAGTGTTTATATTGAAGTGCTGCACTTAACTCAG GGAACATGTTGGGAACAAATGTACACTCCAGGAGGAGAAGTGAGAAATGATGATGTTGA CCAAAGTTTGATTATCGCCGCTAGAAACATAGTAAGAAGAGCAGCAGTGTCAGCAGACC CATTAGCATCTCTCTTGGAAATGTGCCACAGCACACAAATTGGAGATGGAGAGAATAAA AGAACTAAGAGATCTAATGTCGCAGTCTCGCACTCGCGAGATACTCACTAAGACCACTG TGGACCATATGGCCATAATCAAAAAGTACACGTCAGGAAGGCAGGAGAAGAACCCCGCA CTCAGAATGAAATGGATGATGGCAATGAAATACCCAATTACAGCAGACAGGAGAATAAT GGACATGATTCCAGAGAGGAATGAACAAGGACAAACCCTCTGGAGCAAAACAACCGATG CTGGATCGGACCGTGTGATGGTATCACCCCTGGCCGTAACATGGTGGAATAGGAATGGC CCAACAACAAGCACAGTTCACTACCCTAAGGTATACAAAACTTATTTCGAAAAAGTCGA AAGGTTAAAACATGGTACCTTTGGCCCTGTCCACTTCAGAAATCAAGTTAAAATAAGAA GGAGGGTTGACACAAACCCCGGTCATGCAGATCTCAGTGCCAAGGAGGCACAGGATGTG ATCATGGAAGTTGTTTTCCCAAACGAAGTGGGGGCAAGAATACTGACATCAGAGTCACA GCTGACAATAACAAAAGAAAAGAAAGAAGAGCTCCAGGATTGTAAAATTGCTCCCTTGA TGGTGGCATACATGCTAGAAAGAGAATTGGTTCGTAAGACGAGGTTTCTTCCGGTGGCT GGTGGAACAAGCAGTGTTTATATTGAAGTGCTGCACTTAACTCAGGGAACATGTTGGGA ACAAATGTACACTCCAGGAGGAGAAGTGAGAAATGATGATGTTGACCAAAGTTTGATTA TCGCCGCTAGAAACATAGTAAGAAGAGCAGTGTCAGCAGACCCATTAGCATCTCTC TTGGAAATGTGCCACAGCACACAAATTGGAGGAATAAGGATGATGGACATCCTTAGACA GAACCCAACGGAGGAACAAGCCGTAGACATATGCAAGGCAGCAATGGGGCTGAGGATTA GCTCCTCTTTCAGCTTTGGTGGGTTCACCTTCAAAAGGACAAGCGGATCATCTGTTAAG AAAGAAGAAGAAGTGCTCACGGGCAACCTCCAAACACTGAAAATAAGAGTACATGAAGG ATATGAGGAATTCACAATGGTCGGGAGAAGAGCAACAGCTATTCTCAGAAAAGCAACCA GGAGATTGATCCAGTTAATAGTAAGTGGAAGAGACGATCAATCAATTGCTGAGGCAATA ATTGTGGCCATGGTATTTTCACAAGAGGATTGCATGATCAAAGCAGTTAGGGGCGATCT GAACTTTGTCAATAGGGCAAACCAGCGACTGAATCCCATGCACCAACTCTTGAGGCATT TCCAAAAGGATGCAAAAGTGCTTTTCCAGAACTGGGGGATTGAACCCATCGACAGTGTA ATGGGAATGATCGGAATATTGCCTGATATGACCCCAAGCACGGAAATGTCACTGAGAGG TATAAGAGTCAGCAAAATGGGAGTAGATGAATATTCCAGTACGGAGAGAGTGGTAGTGA GCATTGACCGATTTTTGAGAGTTCGGGATCAACGAGGGAACGTACTATTGTCCCCCGAA GAGGTCAGCGAGACACAGGGAACTGAGAAATTGACCATAACTTATTCGTCATCAATGAT GTGGGAGATCAATGGTCCTGAGTCAGTGCTGGTCAACACTTATCAATGGATCATAAGGA ACTGGGAAAGCTTGAAAATTCAATGGTCACAGGATCCCACGATGTTATACAACAAATG GAATTTGAACCATTCCAGTCTCTTGTCCCTAAGGCAACCAGAAGTCGTTACAGTGGATT CGTGAGGACACTGTTCCAGCAAATGCGGGATGTGCTTGGAACATTTGATACTGTCCAAA TAATAAAGCTTCTCCCCTTTGCTGCAGCTCCACCGGAACAGAGTAGGATGCAGTTCTCC TCGCTGACTGTGAATGTAAGAGGATCAGGGCTGAGGATACTGGTAAGAGGCAATTCTCC AGTGTTCAATTACAATAAAGCAACCAAAAGGCTTACAATTCTTGGAAAAGATGCAGGTG CATTGACTGAAGATCCAGATGAAGGCACAGCTGGAGTGGAGTCTGCTGTCCTGAGGGGA TTCCTCATTTTGGGTAAAGAAGACAAGAGATATGGCCCAGCATTAAGCATCAATGAACT GAGCAATCTTGCAAAAGGAGAGAAGGCTAATGTGCTAATTGGGCAAGGAGACGTGGTGT TGGTAATGAAACGGAAACGGGACTCTAGCATACTTACTGACAGCCAGACAGCGACCAAA AGGATTCGGATGGCCATCAATTAG |
| 2 | Flu A 1 polymerase acidic (PA) gene (consensus sequence, KC471368.1 Influenza A virus A/

-continued

TABLE OF CERTAIN SEQUENCES

| SEQ ID NO | Description | Sequence |
|---|---|---|
| | | ATCAAATGCATGAAGACATTCTTTGGCTGGAAAGAGCCTAACATAGTCAAACCACATAA<br>GAAAGGCATAAATCCCAATTACCTTATGGCTTGGAAGCAGGTGCTAACAGAGCTACAGG<br>ACATTGAAAATGAAGAGAAGATCCCAAGGACAAAGAACATGAAGAGAACAAGCCAATTG<br>AAGTGGGCACTCGGTGAAAATATGGCACCAGAAAAAGTAGACTTTGATGACTGCAAAGA<br>TGTTGGAGACCTTAAACAGTATGACAGTGATGAGCCAGAGCCCAGATCTCTAGCAAGCT<br>GGGTCCAAAATGAATTCAATAAGGCATGTGAATTGACTGATTCAAGCTGGATAGAACTT<br>GATGAAATAGGAGAAGATGTTGCCCCGATTGAACATATCGCAAGCATGAGGAGGAACTA<br>TTTTACAGCAGAAGTGTCCCACTGCAGGGCTACTGAATACATAATGAAGGGAGTGTACA<br>TAAATACGGCCTTGCTCAATGCATCCTGTGCAGCCATGGATGACTTTCAGCTGATCCCA<br>ATGATAAGCAAATGTAGGACCAAAGAAGGAAGACGGAAAACAAACCTGTATGGGTTCAT<br>TATAAAAGGAAGGTCTCATTTGAGAAATGATACTGATGTGGTGAACTTTGTAAGTATGG<br>AGTTCTCACTCACTGACCCGAGACTGGAGCCACACAAATGGGAAAAATACTGTGTTCTT<br>GAAATAGGAGACATGCTCTTGAGGACTGCGATAGGCCAAGTGTCGAGGCCCATGTTCCT<br>ATATGTGAGAACCAATGGAACCTCCAAGATCAAGATGAAATGGGGCATGGAAATGAGGC<br>GCTGCCTTCTTCAGTCCCTTCAGCAGATTGAGAGCATGATTGAGGCCGAGTCTTCTGTC<br>AAAGAGAAAGACATGACCAAGGAATTCTTTGAAAACAAATCAGAAACATGGCCAATCGG<br>AGAGTCACCCAGAGGAGTGGAGGAAGGCTCTATTGGGAAAGTGTGCAGGACCTTACTGG<br>CAAAATCTGTGTTCAACAGTCTATATGCGTCTCCACAACTTGAGGGGTTTTCGGCTGAA<br>TCGAGAAAATTGCTTCTCATTGTTCAGGCACTTAGGGACAACCTGGAACCTGGAACCTT<br>CGATCTTGGGGGCTATATGAAGCAATCGAGGAGTGCCTGATTAATGATCCCTGGGTTT<br>TGCTTAATGCATCTTGGTTCAACTCCTTCCTCACACATGCACTGAAGTAG |
| 3 | Flu A 1 matrix protein (MP) gene (consensus sequence KC951136.1 of segment 7 from A/Swine/Pennsylvania/A01432652/2013 (H3N2)) | ATGAGTCTTCTAACCGAGGTCGAAACGTACGTTCTTTCTATCATACCGTCAGGCCCCCT<br>CAAAGCCGAGATCGCGCAGAGACTGGAAAGTGTCTTTGCAGGAAAGAACACAGATCTTG<br>AGGCTCTCATGGAATGGCTAAAGACAAGACCAATCTTGTCACCTTTGACTAAGGGAATT<br>TTAGGATTTGTGTTCACGCTCACCGTGCCCAGTGAGCGAGGACTGCAGCGTAGACGCTT<br>TGTCCAAAATGCCCTAAATGGGAATGGGGACCCAAACAACATGGATAGAGCAGTTAAAC<br>TATACAAGAAGCTCAAAAGAGAAATAACGTTCCATGGGGCCAAGGAGGTGTCACTAAGC<br>TATTCAACTGGTGCACTTGCCAGTTGCATGGGCCTCATATACAACAGGATGGGAACAGT<br>GACCACAGAAGCTGCTTTTGGTCTAGTGTGTGCCACTTGTGAACAGATTGCTGATTCAC<br>AGCATCGGTCTCACAGACAGATGGCTACTACCACCAATCCACTAATCAGGCATGAGAAC<br>AGAATGGTGCTGGCTAGCACTACGGCAAAGGCTATGGAACAGATGGCTGGATCGAGTGA<br>ACAGGCAGCGGAGGCCATGGAGGTTGCTAATCAGACTAGGCAGATGGTACATGCAATGA<br>GAACTATTGGGACTCATCCTAGCTCCAGTACTGGTCTGAAAGATGACCTTCTTGAAAAT<br>TTGCAGGCCTACCAGAAGCGAATGGGAGTGCAGATGCAGCGATTCAAGTGATCCTCTCG<br>CCATTGCAGCAAATATCATTGGGATCTTGCACCTGATATTGTGGATTACTGATCGTCTT<br>TTTTTCAAATGTATTTATCGTCGCTTTAAATACGGTTTGAAAAGAGGGCCTTCTACAGA<br>AGGAGTGCCTGAGTCCATGAGGGAAGAATATCAACAGGAACAGCAGAGTGCTGTGGATG<br>TTGACGATGGTCATTTTGTCAACATAGAGCTAGAGTAA |
| 4 | Flu A 2 1 matrix protein (MP) gene (consensus sequence, KF018056.1 Influenza A virus A/Taiwan/T02081/2013 (H7N9) segment 7) | CGTACGTTCTATCTATCATTCCATCAGGCCCCCTCAAAGCCGAGATCGCGCAGAGACTT<br>GAGGATGTTTTTGCAGGGAAGAACGCAGATCTCGAGGCTCTCATGGAGTGGATAAAGAC<br>AAGACCAATCCTGTCACCTCTGACTAAGGGGATTTTAGGGTTTGTGTTCACGCTCACCG<br>TGCCCAGTGAGCGAGGACTGCAGCGTAGACGGTTTGTCCAAAACGCCCTAAATGGGAAT<br>GGAGACCCAAACAACATGGACAAGGCAGTTAAATTATACAAGAAACTGAAGAGGGAAAT<br>GACATTCCATGGAGCAAAGGAAGTTGCACTCAGTTACTCAACTGGTGCGCTTGCCAGCT<br>GCATGGGTCTCATATACAACAGGATGGGGACAGTAACTGCAGAAGGGGCTCTTGGATTG<br>GTATGTGCCACTTGTGAGCAGATTGCTGACGCACAACATCGGTCCCACAGGCAGATGGC<br>AACTACTACCAACCCACTAATTAGGCATGAGAATAGAATGGTACTAGCCAGTACTACGG<br>CTAAGGCTATGGAGCAGATGGCTGGATCAAGTGAACAGGCAGCGGAAGCCATGGAAGTT<br>GCAAGCCAGGCTAGGCAAATGGTGCAGGCTATGAGAACAGTCGGGACTCACCCTAACTC<br>CAGTACAGGTCTAAAGGATGATCTTATTGAAAATTTGCAGGCTTACCAGAACCGGATGG<br>GAGTGCAACTGCAGCGGTTCAAGTGATCCTCTCGTTGTTGCAGCTAACATTATTGGGAT<br>ATTGCACTTGATATTGTGGATTCTTGATCGTCTTTTCTTCAAATGCATTTATCGTCGCT<br>TTAAATACGGTTTGAAAAGAGGGCCTTCTACGGAAGGAATGCCTGAGTCTATGAGGGAA<br>GAATATCGGCAGGAACAGCAGAATGCTGTGGATGTTGACGATGGTC |
| 5 | Flu A 3 haemagglutinin (HA) gene (consensus sequence, KC896763.1 Influenza A virus A/Nanjing/2913/2013 (H7N9) segment 4) | ATGAACACTCAAATCCTGGTATTCGCTCTGATTGCGATCATTCCAACAAATGCAGACAA<br>AATCTGCCTCGGACATCATGCCGTGTCAAACGGAACCAAAGTAAACACATTAACTGAAA<br>GAGGAGTGGAAGTCGTCAATGCAACTGAAACAGTGGAACGAACAAACATCCCCAGGATC<br>TGCTCAAAAGGGAAAATGACAGTTGACCTCGGTCAATGTGGACTCCTGGGGACAATCAC<br>TGGACCACCTCAATGTGACCAATTCCTAGAATTTTCAGCCGATTTAATTATTGAGAGGC<br>GAGAAGGAAGTGATGTCTGTTATCCTGGGAAATTCGTGAATGAGGAAGCTCTGAGGCAA<br>ATACTCAGAGAATCAGGCGGAATTGACAAGGAAGCAATGGGATTCACATACAGTGGAAT<br>AAGAACTAATGGAGCAACCAGTGCATGTAGGAGATCAGGATCTTCATTCTATGCAGAAA<br>TGAAATGGCTCCTGTCAAACACAGATAATGCTGCATTCCCGCAGATGACTAAGTCATAT<br>AAAAATACAAGAAAAAGCCCAGCTCTAATAGTATGGGGGATCCATCATTCCGTATCAAC<br>TGCAGAGCAAACCAAGCTATATGGGAGTGGAAACAAACTGGTGACAGTTGGGAGTTCTA<br>ATTATCAACAATCTTTTGTACCGAGTCCAGGAGCGAGACCACAAGTTAATGGTCTATCT<br>GGAAGAATTGACTTTCATTGGCTAATGCTAAATCCCAATGATACAGTCACTTTCAGTTT<br>CAATGGGGCTTTCATAGCTCCAGACCGTGCAAGCTTCCTGAGAGGAAAATCTATGGGAA<br>TCCAGAGTGGAGTACAGGTTGATGCCAATTGTGAAGGGGACTGCTATCATAGTGGAGGG<br>ACAATAATAAGTAACTTGCCATTTCAGAACATAGATAGCAGGGCAGTTGGAAAATGTCC<br>GAGATATGTTAAGCAAAGGAGTCTGCTGCTAGCAACAGGGATGAAGAATGTTCCTGAGA |

-continued

TABLE OF CERTAIN SEQUENCES

| SEQ ID NO | Description | Sequence |
|---|---|---|
| | | TTCCAAAGGGAAGAGGCCTATTTGGTGCTATAGCGGGTTTCATTGAAAATGGATGGGAA<br>GGCCTAATTGATGGTTGGTATGGTTTCAGACACCAGAATGCACAGGGAGAGGGAACTGC<br>TGCAGATTACAAAAGCACTCAATCGGCAATTGATCAAATAACAGGAAAATTAAACCGGC<br>TTATAGAAAAAACCAACCAACAATTTGAGTTGATAGACAATGAATTCAATGAGGTAGAG<br>AAGCAAATCGGTAATGTGATAAATTGGACCAGAGATTCTATAACAGAAGTGTGGTCATA<br>CAATGCTGAACTCTTGGTAGCAATGGAGAACCAGCATACAATTGATCTGGCTGATTCAG<br>AAATGGACAAACTGTACGAACGAGTGAAAAGACAGCTGAGAGAGAATGCTGAAGAAGAT<br>GGCACTGGTTGCTTTGAAATATTTCACAAGTGTGATGATGACTGTATGGCCAGTATTAG<br>AAATAACACCTATGATCACAGCAAATACAGGGAAGAGGCAATGCAAAATAGAATACAGA<br>TTGACCCAGTCAAACTAAGCAGCGGCTACAAAGATGTGATACTTTGGTTTAGCTTCGGG<br>GCATCATGTTTCATACTTCTAGCCATTGTAATGGGCCTTGTCTTCATATGTGTAAAGAA<br>TGGAAACATGCGGTGCACTATTTGTATATAA |
| 6 | Flu B matrix protein (MP) gene (consensus sequence, KC814126.1 Influenza B virus B/Utah/03/2011 segment 7 | ATGTCGCTGTTTGGAGACACAATTGCCTACCTGCTTTCATTGACAGAGGATGGAGAAGG<br>CAAAGCAGAACTAGCAGAAAAATTACACTGTTGGTTTGGTGGGAAAGAATTTGACCTAG<br>ACTCTGCCTTGGAATGGATAAAAAACAAAAGATGCTTAACTGATATACAAAAAGCACTA<br>ATTGGTGCCTCTATATGCTTTTTAAAACCCAAAGACCAGGAAAGAAAAAGAAGATTCAT<br>CACAGAGCCCTTATCAGGAATGGGAACAACAGCAACAAAAAAGAAAGGCCTGATTCTGG<br>CTGAGAGAAAAATGAGAAGATGTGTGAGCTTTCATGAAGCATTTGAAATAGCAGAAGGC<br>CATGAAAGCTCAGCGCTACTATACTGTCTCATGGTCATGTACCTGAATCCTGGAAATTA<br>TTCAATGCAAGTAAAACTAGGAACGCTCTGTGCTTTATGCGAGAAACAAGCATCACATT<br>CACACAGGGCTCATAGCAGAGCAGCGAGATCTTCAGTGCCTGGAGTGAGACGAGAAATG<br>CAGATGGTCTCAGCTATGAACACAGCAAAAACAATGAATGGAATGGGAAAAGGAGAAGA<br>CGTCCAAAAGCTGGCAGAAGAGTTGCAAAGCAACATTGGAGTGCTGAGATCTCTTGGAG<br>CAAGCCAAAAGAATGGGGAAGGGATTGCAAAGGATGTAATGGAAGTGCTAAAGCAGAGC<br>TCCATGGGAAATTCAGCTCTTGTGAAGAAATATCTATAATGCTCGAACCATTTCAGATT<br>CTTACAATTTGTTCTTTTATCTTATCAGCTCTCCATTTCATGGCTTGGACAATAGGGCA<br>TTTGAATCAAATAAAAAGAGGAATAAACATGAAAATACGAATAAAAGGTCCAAACAAAG<br>AGACAATAAACAGAGAGGTATCAATTTTGAGACACAGTTACCAAAAAGAAATCCAGGCC<br>AAAGAAACAATGAAGGAAGTACTCTCTGACAACATGGAGGTATTGAATGACCACATAAT<br>AATTGAGGGGCTTTCTGCCGAAGAGATAATAAAAATGGGTGAAACAGTTTTGGAGATAG<br>AAGAATTGCATTAAATTCAATTTTACTATATTTCTTACTATGCATTTAAGCAAATTGTA<br>ATCAATGTCAGCAAATAA |
| 7 | Flu B nonstructural (NS) gene (consensus sequence KC892145.1 Influenza B virus B/California/03/ 2012 segment 8 | ATGGCGAACAACAACATGACCACAACACAAATTGAGGTGGGTCCGGGAGCAACCAATGC<br>CACCATAAACTTTGAAGCAGGAATTCTGGAGTGCTATGAAAGGCTTTCATGGCAAAGAG<br>CCCTTGACTACCCCGGTCAAGACCGCCTAAACAGACTAAAGAGAAAATTAGAGTCAAGA<br>ATAAAGACTCACAACAAAAGTGAGCCTGAAAGTAAAAGGATGTCCCTTGAAGAGAGAAA<br>AGCAATTGGAGTAAAAATGATGAAAGTACTCCTATTTATGAATCCGTCTGCTGGAATTG<br>AAGGGTTTGAGCCATACTGTATGAACAGTTCCTCAAATAGCAACTGTACGAAATACAAT<br>TGGACCGATTACCCTTCAACACCAGAGAGGTGCCTTGATGACATAGAGGAAGAACCAGA<br>GGATGTTGATGGCCCAACTGAAATAGTATTAAGGGACATGAACAACAAAGATGCAAGGC<br>AAAAGATAAAGGAGGAAGTAAACACTCAGAAAGAAGGGAAGTTCCGTTTGACAATAAAA<br>AGGGATATGCGTAATGTATTGTCCTTGAGAGTGTTGGTAAATGGAACATTCCTCAAACA<br>CCCCAATGGATACAAGTCCTTATCAACTCTGCATAGATTGAATGCATATGACCAGAGTG<br>GAAGGCTTGTTGCTAAACTTGTTGCCACTGATGATCTTACAGTGGAGGATGAAGAAGAT<br>GGCCATCGGATCCTCAACTCACTCTTCGAGCGTCTTAATGAAGGACATTCAAAGCCAAT<br>TCGAGCAGCTGAAACTGCGGTGGGAGTCTTATCCCAATTTGGTCAAGAGCACCGATTAT<br>CACCAGAAGAGGGAGACAATTAGACTGGTCACGGAAGAACTTTATCTTTTAAGTAAAAG<br>AATTGATGATAACATACTATTCCACAAAACAGTGATAGCTAACAGCTCCATAATAGCTG<br>ACATGGTTGTATCATTATCATTATTAGAAACATTGTATGAAATGAAGGATGTGGTTGAA<br>GTGTACAGCAGGCAGTGCTTGTGAATTTAAAATAAAAATCCTGTTACTACT |
| 8 | Flu A 1 PB2 amplicon | AAACGGGACTCTAGCATACTTACTGACAGCCAGACAGCGACCAAAAGGATTCGGATGGC<br>CATCAATTA |
| 9 | Flu A 1 PA amplicon | ATCTTGGGGGGCTATATGAAGCAATCGAGGAGTGCCTGATTAATGATCCCTGGGTTTTG<br>CTTAATGCATCTTGGTTCAACTCCTTCCT |
| 10 | Flu A 1 MP amplicon | TTCTAACCGAGGTCGAAACGTACGTTCTTTCTATCATACCGTCAGGCCCCCTCAAAGCC<br>GAGATCGCGCAGAGACTGGAAAGTGTCTTTGCAGGAAAGAACACAGATCTTGAGGCTCT<br>CATGGAATGGCTAAAGACAAGACCAAT |
| 11 | Flu A 2 MP amplicon | CAAGACCAATCCTGTCACCTCTGACTAAGGGGATTTTAGGGTTTGTGTTCACGCTCACC<br>GTGCCCAGTGAGCGAGGACTGCAGCGTAGACG |
| 12 | Flu A 3 HA amplicon | GAAATGAAATGGCTCCTGTCAAACACAGATAATGCTGCATTCCCGCAGATGACTAAGTC<br>ATATAAAAATACAAGAAAAAGC |
| 13 | Flu B MP amplicon | TTTGGAGACACAATTGCCTACCTGCTTTCATTGACAGAGGATGGAGAAGGCAAAGCAGA<br>ACTAGCAGAAAAATTACACTGTTGGTTTGGTGGGAAAGAATTTGACCT |
| 14 | Flu B NS amplicon | GATGGCCATCGGATCCTCAACTCACTCTTCGAGCGTCTTAATGAAGGACATTCAAAGCC<br>AATTCGAGCAGCTGAAACTGCGGTGGGAGTCTTATCCCAATTTGGTCAAGAGC |

-continued

TABLE OF CERTAIN SEQUENCES

| SEQ ID NO | Description | Sequence |
|---|---|---|
| 15 | RSV A amplicon | TACACTCAACAAAGATCAACTTCTGTCATCCAGCAAATACACCATCCAACGGAGCACAGGAGATAGTATTGATACTCCTAATTATGATGTGCAGAAACACATCAACAAGTTATGTGGCATG |
| 16 | RSV B amplicon | CATTAAATAAGGATCAGCTGCTGTCATCCAGCAAATACACTATTCAACGTAGTACAGGAGATAATATTGACACTCCCAATTATGATGTGCAAAAACACCTAAACAAACTATGTGGTATGC |

What is claimed is:

1. A kit for detecting the presence of influenza in a sample from a human subject comprising (a) first primer pair for detecting an influenza A PA gene, wherein the first primer pair comprises a first and second primer, wherein the first primer comprises a sequence that is at least 90% identical to at least 15 contiguous nucleotides of SEQ ID NO: 20; and the second primer comprises a sequence that is at least 90% identical to at least 15 contiguous nucleotides of SEQ ID NO: 21;

(b) a second primer pair for detecting an influenza A PB2 gene, wherein the second primer pair comprises a third and fourth primer, wherein the third primer comprises a sequence that is at least 90% identical to at least 15 contiguous nucleotides of SEQ ID NO: 17, and the fourth primer comprises a sequence that is at least 90% identical to at least 15 contiguous nucleotides of SEQ ID NO: 18;

(c) a third primer pair for detecting an influenza A MP gene, wherein the third primer pair comprises a fifth and sixth primer, wherein the fifth primer comprises a sequence that is at least 90% identical to at least 15 contiguous nucleotides of SEQ ID NO: 23, and the sixth primer comprises a sequence that is at least 90% identical to at least 15 contiguous nucleotides of SEQ ID NO: 24;

(d) a fourth primer pair for detecting an avian influenza MP gene, wherein the fourth primer pair comprises a seventh and eighth primer, wherein
the seventh primer comprises a sequence that is at least 90% identical to at least 15 contiguous nucleotides of SEQ ID NO: 26, and the eighth primer comprises a sequence that is at least 90% identical to at least 15 contiguous nucleotides of SEQ ID NO: 27; and (e) at least one probe selected from an influenza A PA probe comprising a sequence that is at least 90% identical to at least 15 contiguous nucleotides of SEQ ID NO: 22, an influenza A PB2 probe comprising a sequence that is at least 90% identical or complementary to at least 15 contiguous nucleotides of SEQ ID NO: 19, an influenza A MP probe comprising a sequence that is at least 90% identical to at least 15 contiguous nucleotides of SEQ ID NO: 25, and an avian influenza MP probe comprising a sequence that is at least 90% identical to at least 15 contiguous nucleotides of SEQ ID NO: 28.

2. A composition comprising a primer pair comprising a first primer comprising a sequence that is at least 90% identical to at least 15 contiguous nucleotides of SEQ ID NO: 20; and a second primer comprising a sequence that is at least 90% identical to at least 15 contiguous nucleotides of SEQ ID NO: 21; and a probe comprising a sequence that is at least 90% identical or complementary to at least 15 contiguous nucleotides of SEQ ID NO: 22.

3. A composition comprising a primer pair comprising a first primer comprising a sequence that is at least 90% identical to at least 15 contiguous nucleotides of SEQ ID NO: 17; and a second primer comprising a sequence that is at least 90% identical to at least 15 contiguous nucleotides of SEQ ID NO: 18; and a probe comprising a sequence that is at least 90% identical or complementary to at least 15 contiguous nucleotides of SEQ ID NO: 19.

4. A composition comprising a primer pair comprising a first primer comprising a sequence that is at least 90% identical to at least 15 contiguous nucleotides of SEQ ID NO: 23; and a second primer comprising a sequence that is at least 90% identical to at least 15 contiguous nucleotides of SEQ ID NO: 24; and a probe comprising a sequence that is at least 90% identical to at least 15 contiguous nucleotides of SEQ ID NO: 25.

5. A composition comprising a primer pair comprising a first primer comprising a sequence that is at least 90% identical to at least 15 contiguous nucleotides of SEQ ID NO: 26; and a second primer comprising a sequence that is at least 90% identical to at least 15 contiguous nucleotides of SEQ ID NO: 27; and a probe comprising a sequence that is at least 90% identical to at least 15 contiguous nucleotides of SEQ ID NO: 28.

6. The kit of claim 1 further comprising a fifth primer pair for detecting an avian influenza HA gene, wherein the fifth primer pair comprises a ninth and tenth primer, wherein
(i) the ninth primer comprises a sequence that is at least 90% identical to at least 15 contiguous nucleotides of SEQ ID NO: 5, and the tenth primer comprises a sequence that is at least 90% complementary to at least 15 contiguous nucleotides of SEQ ID NO: 5; or (ii) the ninth primer comprises a sequence that is at least 90% identical to at least 15 contiguous nucleotides of SEQ ID NO: 29, and the tenth primer comprises a sequence that is at least 90% identical to at least 15 contiguous nucleotides of SEQ ID NO: 30.

7. The kit of claim 6 further comprising a sixth primer pair for detecting an influenza gene selected from an influenza B MP gene and an influenza B NS gene, wherein the sixth primer pair comprises an eleventh and twelfth primer, wherein:

(i) the eleventh primer comprises a sequence that is at least 90% identical to at least 15 contiguous nucleotides of SEQ ID NO: 6, and the twelfth primer comprises a sequence that is at least 90% complementary to at least 15 contiguous nucleotides of SEQ ID NO: 6;

(ii) the eleventh primer comprises a sequence that is at least 90% identical to at least 15 contiguous nucleotides of SEQ ID NO: 7, and the twelfth primer comprises a sequence that is at least 90% complementary to at least 15 contiguous nucleotides of SEQ ID NO: 7;

(iii) the eleventh primer comprises a sequence that is at least 90% identical to at least 15 contiguous nucleotides of SEQ ID NO: 32, and the twelfth primer comprises a sequence that is at least 90% identical to at least 15 contiguous nucleotides of SEQ ID NO: 33; or (iv) the eleventh primer comprises a sequence that is at least 90% identical to at least 15 contiguous nucleotides of SEQ ID NO: 35, and the twelfth primer comprises a sequence that is at least 90% identical to at least 15 contiguous nucleotides of SEQ ID NO: 36.

8. The kit of claim 7, further comprising a seventh primer pair for detecting RSV A or RSV B, wherein the seventh primer pair comprises a thirteenth and fourteenth primer, wherein:

a. the thirteenth primer comprises a sequence that is at least 90% identical to at least 15 contiguous nucleotides of SEQ ID NO: 38, and the fourteenth primer comprises a sequence that is at least 90% identical to at least 15 contiguous nucleotides of SEQ ID NO: 39; or b. the thirteenth primer comprises a sequence that is at least 90% identical to at least 15 contiguous nucleotides of SEQ ID NO: 41, and the fourteenth primer comprises a sequence that is at least 90% identical to at least 15 contiguous nucleotides of SEQ ID NO: 42.

9. The kit of claim 8, further comprising a primer pair for detecting an exogenous control and/or an endogenous control, wherein the exogenous control is a sample processing control, and wherein the endogenous control is a sample adequacy control.

10. The kit of claim 9, further comprising an exogenous control probe and/or endogenous control probe.

11. The kit of claim 8, wherein at least one primer or probe is detectably labeled.

* * * * *

SEQUENCE LISTING

<160> NUMBER OF SEQ ID NOS: 43

<210> SEQ ID NO 1
<211> LENGTH: 3151
<212> TYPE: DNA
<213> ORGANISM: Influenzavirus A

<400> SEQUENCE: 1

```
atggagagaa taaaagaact aagagatcta atgtcgcagt ctcgcactcg cgagatactc     60
actaagacca ctgtggacca tatggccata atcaaaaagt acacgtcagg aaggcaggag    120
aagaaccccg cactcagaat gaaatggatg atggcaatga aatacccaat tacagcagac    180
aggagaataa tggacatgat tccagagagg aatgaacaag gacaaaccct ctggagcaaa    240
acaaccgatg ctggatcgga ccgtgtgatg gtatcacccc tggccgtaac atggtggaat    300
aggaatggcc caacaacaag cacagttcac taccctaagg tatacaaaac ttatttcgaa    360
aaagtcgaaa ggttaaaaca tggtaccttt ggccctgtcc acttcagaaa tcaagttaaa    420
ataagaagga gggttgacac aaaccccggt catgcagatc tcagtgccaa ggaggcacag    480
gatgtgatca tggaagttgt tttcccaaac gaagtggggg caagaatact gacatcagag    540
tcacagctga caataacaaa agaaaagaaa gaagagctcc aggattgtaa aattgctccc    600
ttgatggtgg catacatgct agaaagagaa ttggttcgta agacgaggtt tcttccggtg    660
gctggtggaa caagcagtgt ttatattgaa gtgctgcact taactcaggg aacatgttgg    720
gaacaaatgt acactccagg aggagaagtg agaaatgatg atgttgacca aagtttgatt    780
atcgccgcta gaaacatagt aagaagagca gcagtgtcag cagacccatt agcatctctc    840
ttggaaatgt gccacagcac acaaattgga gatggagaga ataaaagaac taagagatct    900
aatgtcgcag tctcgcactc gcgagatact cactaagacc actgtggacc atatggccat    960
aatcaaaaag tacacgtcag gaaggcagga gaagaacccc gcactcagaa tgaaatggat   1020
gatggcaatg aaatacccaa ttacagcaga caggagaata atggacatga ttccagagag   1080
gaatgaacaa ggacaaaccc tctggagcaa aacaaccgat gctggatcgg accgtgtgat   1140
ggtatcaccc ctggccgtaa catggtggaa taggaatggc ccaacaacaa gcacagttca   1200
ctaccctaag gtatacaaaa cttatttcga aaaagtcgaa aggttaaaac atggtacctt   1260
tggccctgtc cacttcagaa atcaagttaa aataagaagg agggttgaca caaaccccgg   1320
tcatgcagat ctcagtgcca aggaggcaca ggatgtgatc atggaagttg ttttcccaaa   1380
cgaagtgggg gcaagaatac tgacatcaga gtcacagctg acaataacaa aagaaaagaa   1440
agaagagctc caggattgta aaattgctcc cttgatggtg gcatacatgc tagaaagaga   1500
```

-continued

```
attggttcgt aagacgaggt ttcttccggt ggctggtgga caagcagtg tttatattga      1560
agtgctgcac ttaactcagg gaacatgttg ggaacaaatg tacactccag gaggagaagt      1620
gagaaatgat gatgttgacc aaagtttgat tatcgccgct agaaacatag taagaagagc      1680
agcagtgtca gcagacccat tagcatctct cttggaaatg tgccacagca cacaaattgg      1740
aggaataagg atgatggaca tccttagaca gaacccaacg gaggaacaag ccgtagacat      1800
atgcaaggca gcaatggggc tgaggattag ctcctctttc agctttggtg ggttcacctt      1860
caaaaggaca agcggatcat ctgttaagaa agaagaagaa gtgctcacgg gcaacctcca      1920
aacactgaaa ataagagtac atgaaggata tgaggaattc acaatggtcg ggagaagagc      1980
aacagctatt ctcagaaaag caaccaggag attgatccag ttaatagtaa gtggaagaga      2040
cgatcaatca attgctgagg caataattgt ggccatggta ttttcacaag aggattgcat      2100
gatcaaagca gttaggggcg atctgaactt tgtcaatagg gcaaaccagc gactgaatcc      2160
catgcaccaa ctcttgaggc atttccaaaa ggatgcaaaa gtgcttttcc agaactgggg      2220
gattgaaccc atcgacagtg taatgggaat gatcggaata ttgcctgata tgaccccaag      2280
cacggaaatg tcactgagag gtataagagt cagcaaaatg ggagtagatg aatattccag      2340
tacgagaga gtggtagtga gcattgaccg attttgaga gttcgggatc aacgagggaa      2400
cgtactattg tcccccgaag aggtcagcga gacacaggga actgagaaat tgaccataac      2460
ttattcgtca tcaatgatgt gggagatcaa tggtcctgag tcagtgctgg tcaacactta      2520
tcaatggatc ataaggaact gggaaagctt gaaaattcaa tggtcacagg atcccacgat      2580
gttatacaac aaaatggaat tgaaccatt ccagtctctt gtccctaagg caaccagaag      2640
tcgttacagt ggattcgtga ggacactgtt ccagcaaatg cgggatgtgc ttggaacatt      2700
tgatactgtc caataataa agcttctccc ctttgctgca gctccaccgg aacagagtag      2760
gatgcagttc cctcgctga ctgtgaatgt aagaggatca gggctgagga tactggtaag      2820
aggcaattct ccagtgttca attacaataa agcaaccaaa aggcttacaa ttcttggaaa      2880
agatgcaggt gcattgactg aagatccaga tgaaggcaca gctggagtgg agtctgctgt      2940
cctgagggga ttcctcattt tgggtaaaga agacaagaga tatggcccag cattaagcat      3000
caatgaactg agcaatcttg caaaaggaga aaggctaat gtgctaattg gcaaggaga      3060
cgtggtgttg gtaatgaaac ggaaacggga ctctagcata cttactgaca gccagacagc      3120
gaccaaaagg attcggatgg ccatcaatta g                                     3151
```

<210> SEQ ID NO 2
<211> LENGTH: 2587
<212> TYPE: DNA
<213> ORGANISM: Influenzavirus A

<400> SEQUENCE: 2

```
atggaagact ttgtgcgaca atgcttcaat ccgatgatcg tcgagcttgc ggaaaaggca       60
atgaaagaat atggggaaga tccgaaaatc gaaactaaca gtttgctgc aatatgcaca      120
catttggaag tttgtttcat gtattcggat ttccatttca tcgacgaacg gggtgaatca      180
ataattgtag aatctggtga cccgaatgca ctattgaagc accgatttga gataattgaa      240
ggaagagacc gaatcatggc ctggacagtg gtgaacagta tatgtaacac aacagggta      300
gagaagccta aatttcttcc tgatttgtat gattacaaag aaaaccggtt cattgaaatt      360
ggagtaacac ggagggaagt ccacatatat tacctagaga aagccaacaa aataaaatct      420
gagaagacac acattcatgg aagactttgt gcgacaatgc ttcaatccga tgatcgtcga      480
```

```
gcttgcggaa aaggcaatga aagaatatgg ggaagatccg aaaatcgaaa ctaacaagtt    540
tgctgcaata tgcacacatt tggaagtttg tttcatgtat tcggatttcc atttcatcga    600
cgaacggggt gaatcaataa ttgtagaatc tggtgacccg aatgcactat tgaagcaccg    660
atttgagata attgaaggaa gagaccgaat catggcctgg acagtggtga acagtatatg    720
taacacaaca ggggtagaga agcctaaatt tcttcctgat ttgtatgatt acaaagaaaa    780
ccggttcatt gaaattggag taacacggag ggaagtccac atatattacc tagagaaagc    840
caacaaaata aaatctgaga agacacacat tcacatcttt tcattcactg agaggagat    900 ggccaccaaa gcagactaca cccttgacga agagagcagg gcaagaatca aaactaggct    960
tttcactata agacaagaaa tggccagtag gagtctatgg gattcctttc gtcaatccga   1020
aagaggcgaa gagacaattg aagaaaaatt tgagattaca ggaactatgc gcaagcttgc   1080
cgaccaaagt ctcccaccga acttctccag ccttgaaaac tttagagcct atgtagatgg   1140
attcgagccg aacggctgca ttgagggcaa gcttttccaa atgtcaaagg aagtgaacgc   1200
caaaattgaa ccattcttga ggacgacacc acgcccctc agattgcctg atgggcctct   1260
ttgccatcag cggtcaaagt tcctgctgat ggatgctctg aaattaagta ttgaagaccc   1320
gagtcacgag ggagagggaa taccactata tgatgcaatc aaatgcatga agacattctt   1380
tggctggaaa gagcctaaca tagtcaaacc acataagaaa ggcataaatc ccaattacct   1440
tatggcttgg aagcaggtgc taacagagct acaggacatt gaaaatgaag agaagatccc   1500
aaggacaaag aacatgaaga aacaagcca ttgaagtgg gcactcggtg aaaatatggc   1560
accagaaaaa gtagactttg atgactgcaa agatgttgga gaccttaaac agtatgacag   1620
tgatgagcca gagcccagat ctctagcaag ctgggtccaa aatgaattca ataaggcatg   1680
tgaattgact gattcaagct ggatagaact tgatgaaata ggagaagatg ttgccccgat   1740
tgaacatatc gcaagcatga ggaggaacta ttttacagca gaagtgtccc actgcagggc   1800
tactgaatac ataatgaagg gagtgtacat aaatacggcc ttgctcaatg catcctgtgc   1860
agccatggat gactttcagc tgatcccaat gataagcaaa tgtaggacca agaaggaag   1920 acggaaaaca aacctgtatg ggttcattat aaaaggaagg tctcatttga gaaatgatac   1980
tgatgtggtg aactttgtaa gtatggagtt ctcactcact gacccgagac tggagccaca   2040
caaatgggaa aaatactgtg ttcttgaaat aggagacatg ctcttgagga ctgcgatagg   2100
ccaagtgtcg aggcccatgt tcctatatgt gagaaccaat ggaacctcca agatcaagat   2160
gaaatgggga atggaaatga ggcgctgcct tcttcagtcc cttcagcaga ttgagagcat   2220
gattgaggcc gagtcttctg tcaaagagaa agacatgacc aaggaattct ttgaaaacaa   2280
atcagaaaca tggccaatcg agagtcacc cagaggagtg gaggaaggct ctattgggaa   2340
agtgtgcagg accttactgg caaaatctgt gttcaacagt ctatatgcgt ctccacaact   2400 tgagggggttt tcggctgaat cgagaaaatt gcttctcatt gttcaggcac ttagggacaa   2460
cctggaacct ggaaccttcg atcttggggg gctatatgaa gcaatcgagg agtgcctgat   2520
taatgatccc tgggttttgc ttaatgcatc ttggttcaac tccttcctca cacatgcact   2580
gaagtag                                                             2587
```

<210> SEQ ID NO 3
<211> LENGTH: 982
<212> TYPE: DNA
<213> ORGANISM: Artificial Sequence
<220> FEATURE:

<223> OTHER INFORMATION: Synthetic

<400> SEQUENCE: 3

```
atgagtcttc taaccgaggt cgaaacgtac gttctttcta tcataccgtc aggccccctc     60
aaagccgaga tcgcgcagag actggaaagt gtctttgcag gaaagaacac agatcttgag    120
gctctcatgg aatggctaaa gacaagacca atcttgtcac ctttgactaa gggaatttta    180
ggatttgtgt tcacgctcac cgtgcccagt gagcgaggac tgcagcgtag acgctttgtc    240
caaaatgccc taaatgggaa tggggaccca acaacatgg atagagcagt taaactatac    300
aagaagctca aaagagaaat aacgttccat ggggccaagg aggtgtcact aagctattca    360
actggtgcac ttgccagttg catgggcctc atatacaaca ggatgggaac agtgaccaca    420
gaagctgctt ttggtctagt gtgtgccact tgtgaacaga ttgctgattc acagcatcgg    480
tctcacagac agatggctac taccaccaat ccactaatca ggcatgagaa cagaatggtg    540
ctggctagca ctacggcaaa ggctatggaa cagatggctg gatcgagtga acaggcagcg    600
gaggccatgg aggttgctaa tcagactagg cagatggtac atgcaatgag aactattggg    660
actcatccta gctccagtac tggtctgaaa gatgaccttc ttgaaaattt gcaggcctac    720
cagaagcgaa tgggagtgca gatgcagcga ttcaagtgat cctctcgcca ttgcagcaaa    780
tatcattggg atcttgcacc tgatattgtg gattactgat cgtctttttt tcaaatgtat    840
ttatcgtcgc tttaaatacg gtttgaaaag agggccttct acagaaggag tgcctgagtc    900
catgagggaa gaatatcaac aggaacagca gagtgctgtg gatgttgacg atggtcattt    960
tgtcaacata gagctagagt aa                                             982
```

<210> SEQ ID NO 4
<211> LENGTH: 931
<212> TYPE: DNA
<213> ORGANISM: Artificial Sequence
<220> FEATURE:
<223> OTHER INFORMATION: Synthetic

<400> SEQUENCE: 4

```
cgtacgttct atctatcatt ccatcaggcc ccctcaaagc cgagatcgcg cagagacttg     60
aggatgtttt tgcagggaag aacgcagatc tcgaggctct catggagtgg ataaagacaa    120
gaccaatcct gtcacctctg actaagggga ttttagggtt tgtgttcacg ctcaccgtgc    180
ccagtgagcg aggactgcag cgtagacggt ttgtccaaaa cgccctaaat gggaatggag    240
acccaaacaa catggacaag gcagttaaat tatacaagaa actgaagagg gaaatgacat    300
tccatggagc aaaggaagtt gcactcagtt actcaactgg tgcgcttgcc agctgcatgg    360
gtctcatata caacaggatg ggacagtaa ctgcagaagg ggctcttgga ttggtatgtg    420
ccacttgtga gcagattgct gacgcacaac atcggtccca caggcagatg gcaactacta    480
ccaacccact aattaggcat gagaatagaa tggtactagc cagtactacg gctaaggcta    540
tggagcagat ggctggatca agtgaacagg cagcggaagc catggaagtt gcaagccagg    600
ctaggcaaat ggtgcaggct atgagaacag tcgggactca ccctaactcc agtacaggtc    660
taaaggatga tcttattgaa aatttgcagg cttaccagaa ccggatggga gtgcaactgc    720
agcggttcaa gtgatcctct cgttgttgca gctaacatta tttgggatatt gcacttgata    780
ttgtggattc ttgatcgtct tttcttcaaa tgcatttatc gtcgctttaa atacggtttg    840
aaaagagggc cttctacgga aggaatgcct gagtctatga gggaagaata tcggcaggaa    900
cagcagaatg ctgtggatgt tgacgatggt c                                  931
```

<210> SEQ ID NO 5
<211> LENGTH: 1683
<212> TYPE: DNA
<213> ORGANISM: Artificial Sequence
<220> FEATURE:
<223> OTHER INFORMATION: Synthetic

<400> SEQUENCE: 5

```
atgaacactc aaatcctggt attcgctctg attgcgatca ttccaacaaa tgcagacaaa        60
atctgcctcg acatcatgc cgtgtcaaac ggaaccaaag taaacacatt aactgaaaga       120
ggagtggaag tcgtcaatgc aactgaaaca gtggaacgaa caaacatccc caggatctgc       180
tcaaaaggga aaatgacagt tgacctcggt caatgtggac tcctggggac aatcactgga       240
ccacctcaat gtgaccaatt cctagaattt tcagccgatt taattattga gaggcgagaa       300
ggaagtgatg tctgttatcc tgggaaattc gtgaatgagg aagctctgag gcaaatactc       360
agagaatcag gcggaattga caggaagca atgggattca catacagtgg aataagaact       420
aatggagcaa ccagtgcatg taggagatca ggatcttcat tctatgcaga aatgaaatgg       480
ctcctgtcaa acacagataa tgctgcattc ccgcagatga ctaagtcata taaaaataca       540
agaaaagcc cagctctaat agtatggggg atccatcatt ccgtatcaac tgcagagcaa       600
accaagctat atgggagtgg aaacaaactg gtgacagttg ggagttctaa ttatcaacaa       660
tcttttgtac cgagtccagg agcgagacca caagttaatg gtctatctgg aagaattgac       720
tttcattggc taatgctaaa tcccaatgat acagtcactt tcagtttcaa tggggctttc       780
atagctccag accgtgcaag cttcctgaga ggaaaatcta tgggaatcca gagtggagta       840
caggttgatg ccaattgtga aggggactgc tatcatagtg gagggacaat aataagtaac       900
ttgccatttc agaacataga tagcagggca gttggaaaat gtccgagata tgttaagcaa       960
aggagtctgc tgctagcaac agggatgaag aatgttcctg agattccaaa gggaagaggc      1020
ctatttggtg ctatagcggg tttcattgaa aatggatggg aaggcctaat tgatggttgg      1080
tatggtttca acaccagaa tgcacaggga gagggaactg ctgcagatta caaaagcact      1140
caatcggcaa ttgatcaaat aacaggaaaa ttaaaccggc ttatagaaaa aaccaaccaa      1200
caatttgagt tgatagacaa tgaattcaat gaggtagaga agcaaatcgg taatgtgata      1260
aattggacca gagattctat aacagaagtg tggtcataca atgctgaact cttggtagca      1320
atggagaacc agcatacaat tgatctggct gattcagaaa tggacaaact gtacgaacga      1380
gtgaaaagac agctgagaga gaatgctgaa gaagatggca ctggttgctt tgaaatattt      1440
cacaagtgtg atgatgactg tatggccagt attagaaata acacctatga tcacagcaaa      1500
tacagggaag aggcaatgca aaatagaata cagattgacc cagtcaaact aagcagcggc      1560
tacaaagatg tgatactttg gtttagcttc ggggcatcat gtttcatact tctagccatt      1620
gtaatgggcc ttgtcttcat atgtgtaaag aatggaaaca tgcggtgcac tatttgtata      1680
taa                                                                    1683
```

<210> SEQ ID NO 6
<211> LENGTH: 1139
<212> TYPE: DNA
<213> ORGANISM: Artificial Sequence
<220> FEATURE:
<223> OTHER INFORMATION: Synthetic

<400> SEQUENCE: 6

```
atgtcgctgt tggagacac aattgcctac ctgctttcat tgacagagga tggagaaggc      60
aaagcagaac tagcagaaaa attacactgt tggtttggtg ggaaagaatt tgacctagac     120
tctgccttgg aatggataaa aaacaaaaga tgcttaactg atatacaaaa agcactaatt     180
ggtgcctcta tatgcttttt aaaacccaaa gaccaggaaa gaaaaagaag attcatcaca     240
gagcccttat caggaatggg aacaacagca acaaaaaaga aaggcctgat tctggctgag     300
agaaaaatga aagatgtgt gagctttcat gaagcatttg aaatagcaga aggccatgaa      360
agctcagcgc tactatactg tctcatggtc atgtacctga atcctggaaa ttattcaatg     420
caagtaaaac taggaacgct ctgtgcttta tgcgagaaac aagcatcaca ttcacacagg     480
gctcatagca gagcagcgag atcttcagtg cctggagtga cgagaaat gcagatggtc      540 tcagctatga acacagcaaa aacaatgaat ggaatgggaa aaggagaaga cgtccaaaag     600
ctggcagaag agttgcaaag caacattgga gtgctgagat ctcttggagc aagccaaaag     660
aatggggaag ggattgcaaa ggatgtaatg gaagtgctaa agcagagctc catgggaaat     720
tcagctcttg tgaagaaata tctataatgc tcgaaccatt tcagattctt acaatttgtt     780
cttttatctt atcagctctc catttcatgg cttgacaat agggcatttg aatcaaataa      840
aaagaggaat aaacatgaaa atacgaataa aaggtccaaa caaagagaca ataaacagag     900
aggtatcaat tttgagacac agttaccaaa aagaaatcca ggccaaagaa acaatgaagg     960
aagtactctc tgacaacatg gaggtattga atgaccacat aataattgag gggctttctg     1020
ccgaagagat aataaaaatg ggtgaaacag ttttggagat agaagaattg cattaaattc     1080
aattttacta tatttcttac tatgcattta agcaaattgt aatcaatgtc agcaaataa       1139
```

<210> SEQ ID NO 7
<211> LENGTH: 1054
<212> TYPE: DNA
<213> ORGANISM: Artificial Sequence
<220> FEATURE:
<223> OTHER INFORMATION: Synthetic

<400> SEQUENCE: 7

```
atggcgaaca caacatgac cacaacacaa attgaggtgg gtccgggagc aaccaatgcc     60
accataaact ttgaagcagg aattctggag tgctatgaaa ggctttcatg gcaaagagcc    120
cttgactacc ccggtcaaga ccgcctaaac agactaaaga gaaaattaga gtcaagaata    180
aagactcaca caaaagtga gcctgaaagt aaaaggatgt cccttgaaga gagaaaagca    240
attggagtaa aaatgatgaa agtactccta tttatgaatc cgtctgctgg aattgaaggg    300
tttgagccat actgtatgaa cagttcctca aatagcaact gtacgaaata caattggacc    360 gattacccctt caacaccaga gaggtgcctt gatgacatag aggaagaacc agaggatgtt    420
gatggcccaa ctgaaatagt attaagggac atgaacaaca agatgcaag gcaaaagata    480 aaggaggaag taaacactca gaaagaaggg aagttccgtt tgacaataaa aagggatatg    540
cgtaatgtat tgtccttgag agtgttggta atggaacat tcctcaaaca ccccaatgga    600
tacaagtcct tatcaactct gcatagattg aatgcatatg accagagtgg aaggcttgtt    660
gctaaacttg ttgccactga tgatcttaca gtggaggatg aagaagatgg ccatcggatc    720
ctcaactcac tcttcgagcg tcttaatgaa ggacattcaa agccaattcg agcagctgaa    780
actgcggtgg gagtcttatc ccaatttggt caagagcacc gattatcacc agaagaggga    840
gacaattaga ctggtcacgg aagaacttta tcttttaagt aaaagaattg atgataacat    900
actattccac aaaacagtga tagctaacag ctccataata gctgacatgg ttgtatcatt    960
```

```
atcattatta gaaacattgt atgaaatgaa ggatgtggtt gaagtgtaca gcaggcagtg    1020
cttgtgaatt taaaataaaa atcctgttac tact                                1054
```

<210> SEQ ID NO 8
<211> LENGTH: 68
<212> TYPE: DNA
<213> ORGANISM: Artificial Sequence
<220> FEATURE:
<223> OTHER INFORMATION: Synthetic

<400> SEQUENCE: 8

```
aaacgggact ctagcatact tactgacagc cagacagcga ccaaaaggat tcggatggcc    60
atcaatta                                                             68
```

<210> SEQ ID NO 9
<211> LENGTH: 88
<212> TYPE: DNA
<213> ORGANISM: Artificial Sequence
<220> FEATURE:
<223> OTHER INFORMATION: Synthetic

<400> SEQUENCE: 9

```
atcttggggg gctatatgaa gcaatcgagg agtgcctgat taatgatccc tgggttttgc    60
ttaatgcatc ttggttcaac tccttcct                                       88
```

<210> SEQ ID NO 10
<211> LENGTH: 145
<212> TYPE: DNA
<213> ORGANISM: Artificial Sequence
<220> FEATURE:
<223> OTHER INFORMATION: Synthetic

<400> SEQUENCE: 10

```
ttctaaccga ggtcgaaacg tacgttcttt ctatcatacc gtcaggcccc ctcaaagccg    60
agatcgcgca gagactggaa agtgtctttg caggaaagaa cacagatctt gaggctctca    120
tggaatggct aaagacaaga ccaat                                          145
```

<210> SEQ ID NO 11
<211> LENGTH: 91
<212> TYPE: DNA
<213> ORGANISM: Artificial Sequence
<220> FEATURE:
<223> OTHER INFORMATION: Synthetic

<400> SEQUENCE: 11

```
caagaccaat cctgtcacct ctgactaagg ggatttttagg gtttgtgttc acgctcaccg    60
tgcccagtga gcgaggactg cagcgtagac g                                   91
```

<210> SEQ ID NO 12
<211> LENGTH: 81
<212> TYPE: DNA
<213> ORGANISM: Artificial Sequence
<220> FEATURE:
<223> OTHER INFORMATION: Synthetic

<400> SEQUENCE: 12

```
gaaatgaaat ggctcctgtc aaacacagat aatgctgcat tcccgcagat gactaagtca    60
tataaaaata caagaaaaag c                                              81
```

<210> SEQ ID NO 13

```
<211> LENGTH: 107
<212> TYPE: DNA
<213> ORGANISM: Artificial Sequence
<220> FEATURE:
<223> OTHER INFORMATION: Synthetic

<400> SEQUENCE: 13
tttggagaca caattgccta cctgctttca ttgacagagg atggagaagg caaagcagaa      60
ctagcagaaa aattacactg ttggtttggt gggaaagaat ttgacct                  107

<210> SEQ ID NO 14
<211> LENGTH: 112
<212> TYPE: DNA
<213> ORGANISM: Artificial Sequence
<220> FEATURE:
<223> OTHER INFORMATION: Synthetic

<400> SEQUENCE: 14
gatggccatc ggatcctcaa ctcactcttc gagcgtctta atgaaggaca ttcaaagcca      60
attcgagcag ctgaaactgc ggtgggagtc ttatcccaat ttggtcaaga gc             112

<210> SEQ ID NO 15
<211> LENGTH: 121
<212> TYPE: DNA
<213> ORGANISM: Artificial Sequence
<220> FEATURE:
<223> OTHER INFORMATION: Synthetic

<400> SEQUENCE: 15
tacactcaac aaagatcaac ttctgtcatc cagcaaatac accatccaac ggagcacagg      60
agatagtatt gatactccta attatgatgt gcagaaacac atcaacaagt tatgtggcat    120
g                                                                    121

<210> SEQ ID NO 16
<211> LENGTH: 120
<212> TYPE: DNA
<213> ORGANISM: Artificial Sequence
<220> FEATURE:
<223> OTHER INFORMATION: Synthetic

<400> SEQUENCE: 16
cattaaataa ggatcagctg ctgtcatcca gcaaatacac tattcaacgt agtacaggag      60
ataatattga cactcccaat tatgatgtgc aaaaacacct aaacaaacta tgtggtatgc    120

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
aaacgggact ctagcatact                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
taattgatgg ccatccgaat                                                 20
```

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
agccagacag cgaccaaaag                                          20

<210> SEQ ID NO 20
<211> LENGTH: 25
<212> TYPE: DNA
<213> ORGANISM: Artificial Sequence
<220> FEATURE:
<223> OTHER INFORMATION: Synthetic

<400> SEQUENCE: 20
atcttggggg gctatatgaa gcaat                                    25

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
aggaaggagt tgaaccaaga                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
aatgatccct gggttttgct                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ttctaaccga ggtcgaaacg                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
attggtcttg tctttagcca                                          20

<210> SEQ ID NO 25
<211> LENGTH: 20
<212> TYPE: DNA
<213> ORGANISM: Artificial Sequence
<220> FEATURE:

<223> OTHER INFORMATION: Synthetic

<400> SEQUENCE: 25
tcaggccccc tcaaagccga                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
caagaccaat cctgtcacct                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
cgtctacgct gcagtcctcg                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
acgctcaccg tgcccagtga                                                   20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gaaatgaaat ggctcctgtc                                                   20

<210> SEQ ID NO 30
<211> LENGTH: 25
<212> TYPE: DNA
<213> ORGANISM: Artificial Sequence
<220> FEATURE:
<223> OTHER INFORMATION: Synthetic

<400> SEQUENCE: 30 ggcttttct tgtattttta tatga                                              25

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
ctgcattccc gcagatgac                                                    19

```
<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ttggagacac gattgcctac                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
aggtcaaatt ctttcccacc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
atggagaagg caaagcagaa                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gatggccatc ggatcctcaa                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gctcttgacc aaaattgggat                                              20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
aaagccaatt cgagcagctg                                               20

<210> SEQ ID NO 38
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 38
tacactcaac aaagatcaac ttctgtc                                            27

<210> SEQ ID NO 39
<211> LENGTH: 25
<212> TYPE: DNA
<213> ORGANISM: Artificial Sequence
<220> FEATURE:
<223> OTHER INFORMATION: Synthetic

<400> SEQUENCE: 39
catgccacat aacttattga tgtgt                                              25

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
caccatccaa cggagcacag gaga                                               24

<210> SEQ ID NO 41
<211> LENGTH: 25
<212> TYPE: DNA
<213> ORGANISM: Artificial Sequence
<220> FEATURE:
<223> OTHER INFORMATION: Synthetic

<400> SEQUENCE: 41
cattaaataa ggatcagctg ctgtc                                              25

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
gcataccaca tagtttgttt aggtgtt                                            27

<210> SEQ ID NO 43
<211> LENGTH: 29
<212> TYPE: DNA
<213> ORGANISM: Artificial Sequence
<220> FEATURE:
<223> OTHER INFORMATION: Synthetic

<400> SEQUENCE: 43
taatattgac actcccaatt atgatgtgc                                          29
```